(12) United States Patent
Oura et al.

(10) Patent No.: US 7,445,921 B2
(45) Date of Patent: Nov. 4, 2008

(54) TRANSGLYCOSYLATION METHOD AND PROTEIN HAVING TRANSGLYCOSYLATION ACTIVITY

(75) Inventors: Fusako Oura, Tokyo (JP); Kiyotaka Fujita, Kagoshima (JP); Noriko Nagamine, Kyoto (JP); Kenji Yamamoto, Shiga (JP); Masanori Yamaguchi, Aomori (JP); Hayato Ozawa, Kyoto (JP); Takane Katayama, Ishikawa (JP); Hidehiko Kumagai, Ishikawa (JP); Shunichi Suzuki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 36 days.

(21) Appl. No.: 11/233,174

(22) Filed: Sep. 23, 2005

(65) Prior Publication Data
US 2006/0223140 A1    Oct. 5, 2006

Related U.S. Application Data

(63) Continuation-in-part of application No. 11/089,508, filed on Mar. 25, 2005, now abandoned.

(30) Foreign Application Priority Data

| Sep. 24, 2004 | (JP) | ............................ 2004-277714 |
| Mar. 22, 2005 | (JP) | ............................ 2005-082340 |
| Sep. 20, 2005 | (JP) | ............................ 2005-272770 |

(51) Int. Cl.
*C12N 9/10* (2006.01)
*C12N 15/00* (2006.01)
*C12P 19/28* (2006.01)
*C12P 21/06* (2006.01)
*C12P 19/10* (2006.01)
*C11N 1/20* (2006.01)

(52) U.S. Cl. .................. 435/193; 435/85; 435/101; 435/252.3; 435/320.1

(58) Field of Classification Search ............... None
See application file for complete search history.

(56) References Cited

U.S. PATENT DOCUMENTS 6,740,509 B2 * 5/2004 Karakasa et al. ............... 435/74

FOREIGN PATENT DOCUMENTS

| EP | 1 227 152 A1 * | 7/2002 |
| WO | 01/42215 | 6/2001 |
| WO | 01-42225 | 6/2001 |

OTHER PUBLICATIONS

Bardales et al., Transglycosylation and transfer reaction activities of Endo-alpha-N-acetyl-D-galctosaminidase from Diplococcus (Streptococcus) pneumoniae. J.Biol.Chem., 1989, vol. 33 (25): 19893-19897.*

Ashida et al., Characterization of Endo-alpha-N-acetylgalactosaminidase from *Bacillus* sp., and synthesis of Neo-oligosaccharides using its transglycosylation activity. Arch. Biochem Biophysics., 2000, vol. 373 (2): 394-400.*

Schell et al., The genome sequence of Bifidobacterium longum reflects its adaptation to the human gastrointestinal tract. Proc. Nat. Acad. Sci., 2002, vol. 99 (22): 14422-14427.*

Oura et a., Molecular cloning and characterization of endo-aplha-N-acetylgalactosaminidase from Bifidobacterium longum. Abstract 466, Joint Meeting of the Society for Glycobiology and Japanese Society of Carbohydrate Research, Nov. 17-20, 2004, Honolulu, HI, USA.*

Whisstock et al., Prediction of protein function from protein sequence and structure. Q Rev Biophysics., 2003, vol. 36 (3): 307-340.*

Guo et al., Protein tolerance to random amino acid change. PNAS., 2004, vol. 101: 9205-9210. Published online Jun. 14, 2004.[.*

T. Katayama, et al., "Novel Bifidobacterial Glycosidases Acting on Sugar Chains of Mucin Glycoproteins", Journal of Bioscience and Bioengineering, vol. 99, No. 5, 2005, pp. 457-465, XP-004997036.

K. Fujita, et al., "Identification and Molecular Cloning of a Novel Glycoside Hydrolase Family of Core 1 Type O-Glycan-Specific Endo-Alpha-Acetylgalactosaminidase From Bifidobacterium Longum", The Journal of Biological Chemistry, vol. 280, No. 45, Nov. 11, 2005, pp. 37415-37422, XP-002383896.

Dostal, V., et al., "Determination of Acids and Their Strenth in Isobutyl Methyl Ketone," Colleciton of Czechoslovak Chemical Communications, vol. 47, No. 4, 1982, pp. 1203-1215, XP002405365.

Certificate by the Chairperson of Japan Society for Bioscience, Biotechnology and Agrochemistry, including documents such as a abstract of the presentation of Mar. 30, 2004 by Oura et al, and partial translations thereof.

Certificate by the Chairperson of Japanese Society of Carbohydrate Research, including documents such as a abstract of the presentation of May 29, 2004 by Oura et al., and partial translations thereof.

* cited by examiner

*Primary Examiner*—Rebecca E. Prouty
*Assistant Examiner*—Ganapathirama Raghu
(74) *Attorney, Agent, or Firm*—Oblon, Spivak, McClelland, Maier & Neustadt, P.C.

(57) ABSTRACT

The present invention provides a transglycosylation method and a protein catalyzing a transglycosylation reaction. A reaction of transferring a galactosylβ1→3N-acetylgalactosaminyl group from a sugar donor containing a sugar chain having a galactosylβ1→3N-acetylgalactosaminyl group bound thereto at the α-position, to a sugar chain acceptor, is carried out in the presence of a protein having an endo-α-N-acetylgalactosaminidase activity and a transglycosylation activity.

19 Claims, 10 Drawing Sheets

US 7,445,921 B2

TRANSGLYCOSYLATION METHOD AND PROTEIN HAVING TRANSGLYCOSYLATION ACTIVITY

CROSS-REFERENCE TO RELATED APPLICATIONS

This application is a continuation-in-part of application U.S. Ser. No. 11/089,508 (now abandoned) filed on Mar. 25, 2005, which claims the benefit of priority based on the Japanese Patent Application No.2004-277714 filed on Sep. 24, 2004, the entire disclosures of which are incorporated herein by reference.

BACKGROUND OF THE INVENTION

1. Field of the Invention

The present invention relates to a transglycosylation method, a glycosidase having transglycosylation activity and applications thereof.

2. Description of the Related Art

Endo-α-N-acetylgalactosaminidase (hereinafter, "Endo-α" or "Endo-α-GalNAc-ase") is an enzyme which recognizes a core 1 structure of an O-linked sugar chain in glycoprotein, that is, a structure having a galactosylβ1→3N-acetylgalactosamine (hereinafter, "Galβ1-3GalNAc") disaccharide bound at the α-position to serine or threonine, and which releases the disaccharide unit by hydrolysis. The O-linked sugar chain is also called a mucin-type sugar chain and is contained in a large amount in mucin with which the surfaces of animal digestive tracts and organs are covered.

It has been reported that Endo-α producing bacteria are found in a culture of, for example, *Diplococcus pneumoniae* and bacteria belonging to the genus *Clostridium* (for example, Bhavanandan, V. P. et al., Biochem. Biophys. Res. Commum., 70, 738-745 (1976)). It has also been reported that in some Endo-α studied up to now, there is a transglycosylation activity of transferring and adding a disaccharide to an entering suitable acceptor in place of a water molecule upon hydrolysis (For example, Bardales, R. M. and Bhavanandan, V. P., J. Biol. Chem., 264, 19893-19897 (1989)). Among microorganisms known as the Endo-α-producing bacteria, there are microorganisms whose total genome sequence has been clarified.

The presence of the Endo-α-producing microorganism is known, but there is no report on the cloning of a gene for an enzyme having the Endo-α activity. That is, the amino acid sequence of the Endo-α is not revealed, and which gene is a gene encoding the Endo-α has not been specified.

SUMMARY OF THE INVENTION

Sugar chain are very important in the living body or the like, and in study on sugar chains, production of desired sugar chains, and production of glycoprotein, enzymes capable of transferring and adding various kinds of sugar chains have been desired. Under such circumstances, the object of the present invention is to provide a novel enzyme capable of transferring and adding a sugar chain and a method of transferring a sugar chain, that is, a method of transglycosylation.

The Endo-α is generally a hydrolase, and the present inventors have found an enzyme having extremely high transglycosylation activity from the Endo-α enzymes. Further, they have succeeded in specifying its gene to complete the present invention. The present invention also provides a transglycosylation method and a protein catalyzing a transglycosylation reaction, to be described below.

1. A method for transglycosylation, comprising a reaction of transferring a galactosylβ1→3N-acetylgalactosaminyl group from a sugar donor containing a sugar chain having a galactosylβ1→3N-acetylgalactosaminyl group bound thereto at the α-position, to a sugar chain acceptor, in the presence of a protein having an endo-α-N-acetylgalactosaminidase activity and a transglycosylation activity.

2. The method for transglycosylation according to item 1, wherein the protein is derived from a microorganism belonging to the genus *Bifidobacterium*.

3. The method for transglycosylation according to item 1, wherein the protein is selected from the group of (A) and (B):
(A) a protein having an amino acid sequence described in SEQ ID NO:2, and
(B) a protein having an endo-α-N-acetylgalactosaminidase activity and a transglycosylation activity, and having the amino acid sequence that includes one or several amino acids mutation in the amino acid sequence described in SEQ ID NO: 2, the mutation being selected from the group consisting of substitution, deletion, insertion, addition, and inversion.

4. The method for transglycosylation according to item 1, comprising:
cultivating in a medium a transformed cell into which a polynucleotide encoding the protein having an endoα-N-acetylgalactosaminidase activity and a transglycosylation activity was introduced, and accumulating the protein in the medium and/or the transformed cell thereby supplying the protein,
wherein the protein is selected from the group consisting of:
(A) a protein having an amino acid sequence described in SEQ ID NO:2, and
(B) a protein having an endo-α-N-acetylgalactosaminidase activity and a transglycosylation activity, and having the amino acid sequence that includes one or several amino acids mutation in the amino acid sequence described in SEQ ID NO: 2, the mutation being selected from the group consisting of substitution, deletion, insertion, addition, and inversion.

5. The method for transglycosylation according to any one of items 1 to 4, wherein the sugar chain acceptor is selected from the group consisting of a monosaccharide, an oligosaccharide, an alcohol (1-alkanol), an amino acid and a polypeptide.

6. A method of modifying a food,
wherein the food before modification contains a sugar chain acceptor selected from the group consisting of a monosaccharide, an oligosaccharide, an alcohol (1-alkanol), an amino acid and a polypeptide,
the method comprising a reaction of transferring a galactosylβ1→3N-acetylgalactosaminyl group from a sugar donor containing a sugar chain having a galactosylβ1→3N-acetylgalactosaminyl group bound thereto at the α-position, to the sugar chain acceptor, in the presence of a protein having an endo-α-N-acetylgalactosaminidase activity and a transglycosylation activity.

7. A method of modifying a drug,
wherein the drug before modification contains a sugar chain acceptor selected from the group consisting of a monosaccharide, an oligosaccharide, an alcohol (1-alkanol), an amino acid and a polypeptide,
the method comprising a reaction of transferring a galactosylβ1→3N-acetylgalactosaminyl group from a sugar donor containing a sugar chain having a galactosylβ1→3N-acetylgalactosaminyl group bound thereto at the α-position, to the sugar chain acceptor, in the presence of a protein having an endo-α-N-acetylgalactosaminidase activity and a transglycosylation activity.

8. A protein derived from a microorganism belonging to the genus *Bifidobacterium* and having an endo-α-N-acetylgalactosaminidase activity and a transglycosylation activity.

9. A protein selected from the group consisting of (A) and (B):
   (A) a protein having an amino acid sequence described in SEQ ID NO:2, and
   (B) a protein having an endo-α-N-acetylgalactosaminidase activity and a transglycosylation activity, and having the amino acid sequence that includes one or several amino acids mutation in the amino acid sequence described in SEQ ID NO: 2, the mutation being selected from the group consisting of substitution, deletion, insertion, addition, and inversion.

10. A polynucleotide encoding a protein selected from the group consisting of (A) and (B):
    (A) a protein having an amino acid sequence shown in SEQ ID NO:2, and
    (B) a protein having an endo-α-N-acetylgalactosaminidase activity and a transglycosylation activity, and having the amino acid sequence that includes one or several amino acids mutation in the amino acid sequence described in SEQ ID NO: 2, the mutation being selected from the group consisting of substitution, deletion, insertion, addition, and inversion.

11. A polynucleotide selected from the group consisting of (a) and (b):
    (a) a polynucleotide consisting of a nucleotide sequence shown in SEQ ID NO:1, and
    (b) a polynucleotide which hybridizes under stringent conditions with a polynucleotide consisting of a nucleotide sequence complementary to a nucleotide sequence shown in SEQ ID NO:1, and which encodes a protein having an endo-α-N-acetylgalactosaminidase activity and a transglycosylation activity.

12. A recombinant polynucleotide containing the polynucleotide according to item 10.

13. A recombinant polynucleotide containing the polynucleotide according to item 11.

14. A transformed cell containing the recombinant polynucleotide according to item 12.

15. A transformed cell containing the recombinant polynucleotide according to item 13.

16. A method for producing a protein, comprising:
    culturing the transformed cell according to item 14 in a medium and accumulating a protein having an endo-α-N-acetylgalactosaminidase activity and a transglycosylation activity in the medium and/or the transformed cell.

17. A method for producing a protein, comprising:
    culturing the transformed cell according to item 15 in a medium and accumulating a protein having an endo-α-N-acetylgalactosaminidase activity and a transglycosylation activity in the medium and/or the transformed cell.

18. A method for producing a compound selected from the group consisting of a sugar chain, a sugar alcohol and a glycoprotein, the method comprising the step of transferring a galactosylβ1→3N-acetylgalactosaminyl group from a sugar donor containing a sugar chain having a galactosylβ1→3N-acetylgalactosaminyl group bound thereto at the α-position, to a sugar chain acceptor, in the presence of a protein having an endo-α-N-acetylgalactosaminidase activity and a transglycosylation activity.

19. The method according to item 18, wherein the protein is derived from a microorganism belonging to the genus *Bifidobacterium*.

20. The method according to item 18, wherein the protein is selected from the group of (A) and (B):
    (A) a protein having an amino acid sequence described in SEQ ID NO:2, and
    (B) a protein having an endo-α-N-acetylgalactosaminidase activity and a transglycosylation activity, and having the amino acid sequence that includes one or several amino acids mutation in the amino acid sequence described in SEQ ID NO: 2, the mutation being selected from the group consisting of substitution, deletion,. insertion, addition, and inversion.

21. The method according to item 18, wherein said step of transferring comprises:
    cultivating in a medium a transformed cell into which a polynucleotide encoding the protein having an endo-α-N-acetylgalactosaminidase activity and a transglycosylation activity was introduced, and accumulating the protein in the medium and/or the transformed cell thereby supplying the protein.

22. The method according to item 18, wherein said step of transferring comprises:
    cultivating in a medium a transformed cell into which a polynucleotide encoding the protein having an endo-α-N-acetylgalactosaminidase activity and a transglycosylation activity was introduced, and accumulating the protein in the medium and/or the transformed cell thereby supplying the protein, wherein said protein is derived from a microorganism belonging to the genus *Bifidobacterium*.

23. The method according to item 18, wherein said step of transferring comprises:
    cultivating in a medium a transformed cell into which a polynucleotide encoding the protein having an endo-α-N-acetylgalactosaminidase activity and a transglycosylation activity was introduced, and accumulating the protein in the medium and/or the transformed cell thereby supplying the protein,
    wherein the protein is selected from the group consisting of:
    (A) a protein having an amino acid sequence described in SEQ ID NO:2, and
    (B) a protein having an endo-α-N-acetylgalactosaminidase activity and a transglycosylation activity, and having the amino acid sequence that includes one or several amino acids mutation in the amino acid sequence described in SEQ ID NO: 2, the mutation being selected from the group consisting of substitution, deletion, insertion, addition, and inversion.

24. The method according to any one of items 18 to 23, wherein the sugar chain acceptor is selected from the group consisting of a monosaccharide, an oligosaccharide, an alcohol (1-alkanol), an amino acid and a polypeptide.

According to the present invention, there are provided a new transglycosylation method and a protein catalyzing a transglycosylation reaction. The present invention may be utilized for industry related to the sugar chain engineering such as production for glycoprotein.

BRIEF DESCRIPTION OF THE DRAWINGS

FIG. 4 shows the results of measurement of transglycosylation activity into 1-alkanol.

DETAILED DESCRIPTIONS

Hereinafter, the present invention is described in more detail with reference to exemplary embodiments. For carrying out biochemical or genetic engineering techniques in the present invention, reference is made to various experimental manuals such as Molecular Cloning: A LABORATORY MANUAL, 3rd edition, Cold Spring Harbor Laboratory Press, Cold Spring Harbor, N.Y. (2001); "Shin Idenshi Kogaku Handbook (New Genetic Engineering Handbook)", by Masami MURAMATSU, et al, Yodosha, Experimental Medicine, extra issue, 3rd edition, 1999; "Tanpakushitsu Jikken No Susumekata (How to Advance Protein Experiment)", by Masato OKADA and Kaori MIYAZAKI, Yodosha, 1st edition, 1998; and "Tanpakushitsu Jikken Note (Protein Experimental Note)" by Masato OKADA and Kaori MIYAZAKI, Yodosha, 2nd edition, 1999.

In the transglycosylation method of the present invention, a protein having endo-α-N-acetylgalactosaminidase activity and transglycosylation activity is used as a catalyst to transfer a sugar chain from a sugar chain donor to a sugar chain acceptor. The sugar chain is transferred from the sugar chain donor and fed to a transfer reaction system, and the sugar chain acceptor accepts the sugar chain supplied by the sugar chain donor. The sugar chain donor contains a galactosyl β1→3N-acetylgalactosaminyl α-group. Galactosyl β1→3N-acetylgalactosamine is a disaccharide having galactose and N-acetylgalactosamine bound via β (1→3). In this specification, galactosyl β1→3N-acetylgalactosamine is also referred to hereinafter as Galβ1-3GalNAc, and the galactosyl β1→3N-acetylgalactosaminyl α-group is also referred to hereinafter as Galβ1-3GalNAcα-group.

Figure 1:
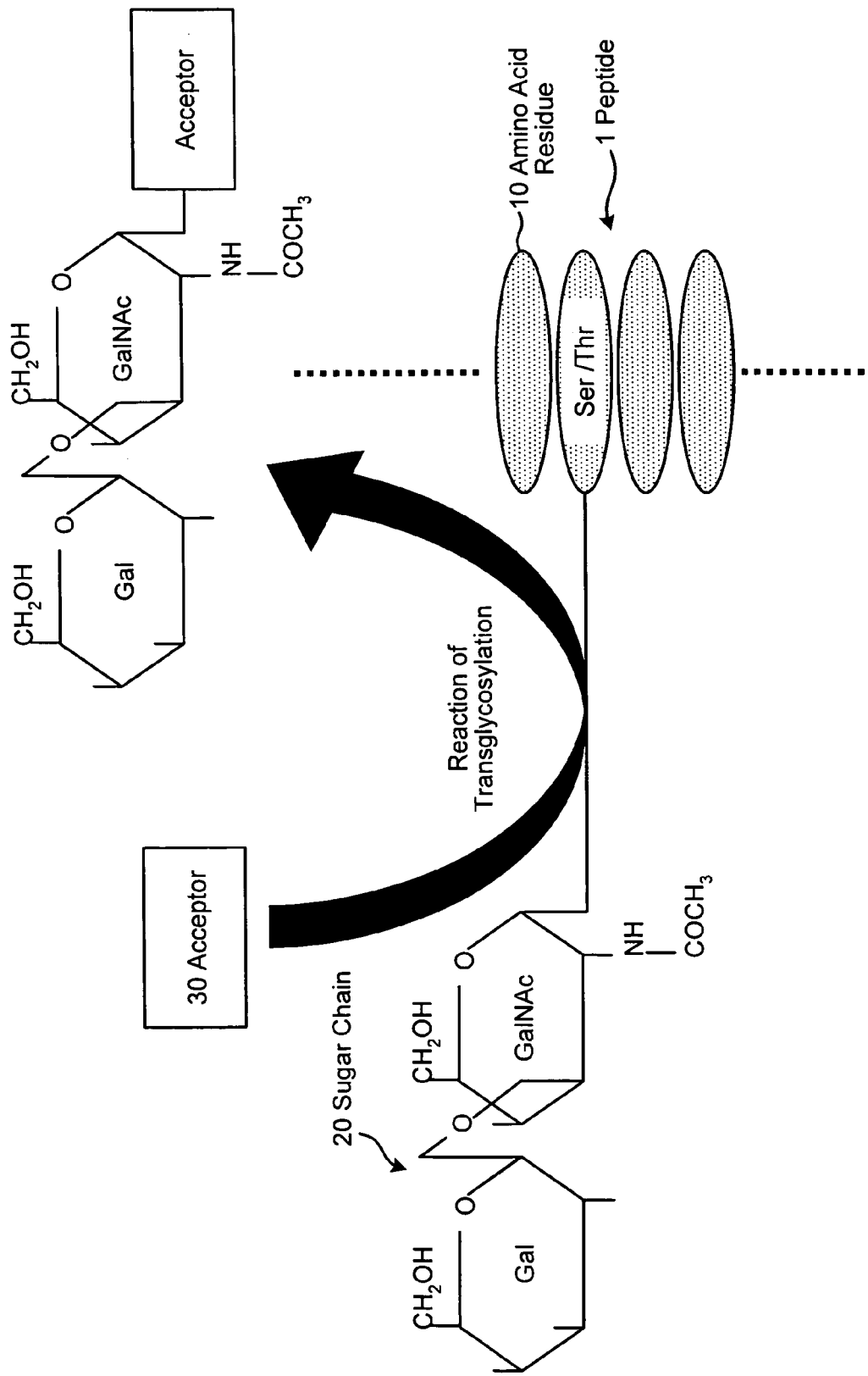
FIG. 1 is a schematic diagram of the transglycosylation reaction.

The protein used in the method for transglycosylation of the present invention has at least two activities, that is, endo-α-N-acetylgalactosaminidase activity and transglycosylation activity. Endo-α-N-acetylgalactosaminidase is an enzyme which recognizes a core 1 structure of an O-linked sugar chain in glycoprotein, that is, a structure having a Galβ1-3GalNAc disaccharide bound at the α-position to serine or threonine, and which has at least an activity of catalyzing a reaction of releasing the disaccharide unit by hydrolysis. The O-linked sugar chain is also called a mucin-type sugar chain and is contained in a large amount in mucin with which the surfaces of animal digestive tracts and organs are covered. The protein used in the present invention also has transglycosylation activity. As shonw in FIG. 1, the protein catalyzing the transglycosylation reaction in the transglycosylation method of the present invention can recognize at least a structure wherein a sugar chain moiety 20 of Galβ1-3GalNAc group in a glycoprotein (peptide 1) is bound at the α-position to serine or threonine, and which has an activity of transferring the Galβ1-3GalNAc group to an acceptor 30. The transglycosylation activity of the protein used in the present invention is high. The protein exhibiting a transglycosylation degree (%) of at least 2%, preferably 5% or more, more preferably 10% or more, still more preferably 15% or more, as determined by a method shown later in the Examples, is used.

The terms "in the presence of the protein" means that the reaction system is placed under conditions where the transglycosylation reaction can be carried out by the catalytic action of this protein. The protein may be supplied for example by adding a microorganism and/or the enzyme to the reaction system. That is, the microorganism and/or the enzyme may be allowed to be present in the reaction system in any form, provided that the microorganism and/or the enzyme effects the reaction of transferring galactosyl β1→3N-acetylgalactosaminyl group from a galactosyl β1→3N-acetylgalactosaminyl α-group-containing sugar chain donor to a sugar chain acceptor. Either of the microorganism or enzyme may be used, or both of them may be present.

The "microorganism and/or the enzyme" may be in the following form. The specific form may include a culture of the microorganisms, microbial cells separated from the culture, and a treated microbial cell product. The culture of the microorganisms is a material obtained by cultivating the microorganisms, and refers more specifically to a mixture of the microbial cells, a culture used in cultivating the microorganisms, and substances formed by the microorganism. The microbial cells may be used as a washed microorganisms after washing the cells. The treated microbial cell product may include materials obtained by disrupting, lyzing or freeze-drying the bacterium, as well as a crudely purified enzyme recovered by treating the microorganism etc. or a purified enzyme obtained by further purification. As the enzyme subjected to purification treatment, it is possible to use a enzyme such as partially purified enzyme obtained by various purification methods or an immobilized enzyme having such enzyme immobilized by a covalent bonding method, an adsorption method, an inclusion method or the like. Some of the used microorganisms are lyzed during cultivation, and in this case, a supernatant of the culture may also be utilized as a material containing the protein having transglycosylation activity.

The conditions in the reaction system using the microorganism and/or the enzyme may be suitably regulated depending on the condition such as specific type of microorganism, enzyme and starting material used. The amount of the microorganism and/or enzyme used may be an amount (effective amount) to exhibit the desired effect. This effective amount can be easily determined in a preliminary experiment which can be carried out easily by those skilled in the art; for example, when the enzyme is used, about 0.01 to 100 units (U) is preferable, and when the washed microorganisms are used, about 0.1 to 500 g/L is preferable. The reaction is carried out at a temperature in the range where the enzyme used is active; that is, the reaction temperature is preferably in the range of 10 to 70° C., more preferably 20 to 65° C., still more preferably 25 to 60° C. The pH value of the enzyme reaction solution is regulated usually in the range of 2 to 12, preferably 4 to 10, more preferably 5 to 6.

The protein catalyzing the reaction described above may be obtained from a microorganism belonging to the genus *Bifidobacterium*. More specific example may include preferably *Bifidobacterium longum*, more preferably *Bifidobacterium longum* JCM1217. The stains given JCM numbers have been deposited with Japan Collection of Microorganisms, Riken Bioresource Center, (Hirosawa 2-1, Wako City, Saitama Prefecture, 351-0198, Japan), and may be obtained according to a predetermined procedure.

More specific examples of the protein catalyzing the transglycosylation reaction may include the following protein (A) and (B):

(A) a protein having an amino acid sequence of SEQ ID NO:2, or
(B) a protein having an endo-α-N-acetylgalactosaminidase activity and a transglycosylation activity, and having the amino acid sequence that includes one or several amino acids mutation in the amino acid sequence of SEQ ID NO: 2, the mutation being selected from the group consisting of substitution, deletion, insertion, addition, and inversion.

The present inventors newly isolated a protein having the amino acid sequence of SEQ ID NO:2 from *Bifidobacterium longum* JCM1217, and specified the amino acid sequence of the protein catalyzing the above reaction.

In the production method of the present invention, a protein which is substantially the same as the protein shown in (A) above may also be used. Specifically, the protein shown in (B) is provided. Herein, the term "several" refers to the number of amino acids within a range, which have less effect on the three-dimensional structure of the protein composed of amino-acid residues and the activity of the protein. It may be depending on the location and the types of amino-acid residues in the three-dimensional structure of the protein, and the range is specifically 2 to 50, preferably 2 to 30, and several preferably 2 to 10. Note that it is desirable that among those of protein groups (B), the protein having the amino acid sequence containing mutation of one or several amino acid residues selected from the group of consisting of substitution, deletion, insertion, addition, and inversion, retain approximately 50% or more, more preferably 80% or more, and further preferably 90% or more of enzyme activity of the protein containing no mutation under the conditions, 50° C. and pH8.

The mutation in amino acids as shown in the aforementioned (B) may be induced by modifying the nucleotide sequence so that the amino acids at the corresponding sites of the enzyme gene may be substituted, deleted, inserted, added, and/or inverted using, for example, the site-specific mutation method. Alternatively, the polynucleotide having modified nucleotide sequence may be obtained by the conventionally known the mutation process. The mutation process may include a technique involving a step for in vitro inducing the mutation in the DNA encoding the amino acids of the (A) under the treatment of hydroxylamine and a technique involving a step for introducing the mutation in a bacterium belonging to the genus *Escherichia* containing the DNA encoding the amino acids of the (A) by UV irradiation, or under the treatment with N-methyl-N'-nitro-N-nitrosoguanidine (NTG) or any of mutating agents generally used for mutation engineering, such as nitrous acid.

Mutations such as substitution, deletion, insertion, addition and inversion in amino acids, accompanying the modification to the nucleotide sequence, may include naturally occurring mutations such as differences due to microbial species or microbial strain. By expressing such mutated DNA in a suitable cell and examining the activity of the present enzyme in the expression product, a DNA encoding substantially the same protein as the protein of SEQ ID NO:2 is obtained.

The polynucleotide encoding the protein used in the transglycosylation method of the present invention includes a polynucleotide encoding the amino acid sequence shown in SEQ ID NO:2. By codon degeneracy, there can be a plurality of nucleotide sequences encoding one amino acid sequence. That is, the polynucleotide of the present invention includes polynucleotides having nucleotide sequences encoding the following proteins:

(A) a protein having an amino acid sequence of SEQ ID NO:2, and
(B) a protein having an endo-α-N-acetylgalactosaminidase activity and a transglycosylation activity, and having the amino acid sequence that includes one or several amino acids mutation in the amino acid sequence of SEQ ID NO: 2, the mutation being selected from the group consisting of substitution, deletion, insertion, addition, and inversion.

The nucleotide sequence encoding the amino acid sequence of SEQ ID NO:2 is exemplified by the nucleotide sequence of SEQ ID NO:1. Further, as the polynucleotide which is substantially the same as the DNA having the nucleotide sequence of SEQ ID NO:1, there may be mentioned a polynucleotide substantially the same as the polynucleotide having the nucleotide sequence shown in SEQ ID NO:1 and obtained by isolating a polynucleotide which hybridizes under stringent conditions with a polynucleotide consisting of, or with a probe prepared from, a nucleotide sequence complementary to the nucleotide sequence shown in SEQ ID NO:1 and which encodes a protein having an endo-α-N-acetylgalactosaminidase activity and a transglycosylation activity, from a polynucleotide encoding the protein having the amino acid sequence shown in SEQ ID NO:2 or from a cell retaining the polynucleotide.

Specific examples of the polynucleotide of the present invention preferably include the following polynucleotides (a) and (b):

(a) a polynucleotide having a nucleotide sequence shown in SEQ ID NO:1 in the Sequence Listing, and
(b) a polynucleotide which hybridizes under stringent conditions with a polynucleotide consisting of a nucleotide sequence complementary to the nucleotide sequence of SEQ ID NO:1, and which encodes a protein having an endo-α-N-acetylgalactosaminidase activity and a transglycosylation activity.

The probe may be prepared in an ordinary method for example on the basis of the nucleotide sequence shown in SEQ ID NO:1. The method of probing, which the desired polynucleotide is isolated by screening a polynucleotide hybridizing with the probe, may also be carried out in an ordinary method. For example, the DNA probe may be prepared by amplifying the nucleotide sequence cloned in a plasmid or a phage vector, cleaving with a restriction enzyme a nucleotide sequence intended to be used as the probe, and extracting it. The site to be cleaved off may be regulated depending on the desired DNA.

As used herein, the "stringent conditions" refers to those conditions under which a specific hybrid is formed whereas an unspecific hybrid is not formed. These conditions are hardly expressed explicitly numerically, but by way of example, there may be mentioned those conditions under which DNA molecules having higher homology e.g. preferably 50% or more, more preferably 80% or more, still more preferably 90% or more, further more preferably 95% or more homology, hybridize with each other while DNA molecules having lower homology do not hybridize with each other, or those conditions under which hybridization occurs under usual washing conditions in Southern hybridization, that is, at a salt concentration corresponding to 1×SSC and 0.1% SDS at 60° C., preferably 0.1×SSC and 0.1% SDS at 60° C. Among the genes hybridizing under such conditions, there are genes having a stop codon in their sequence or encoding enzymes whose activity is lost due to a mutation in active center, and such genes can be easily removed by ligating each of them into a commercial expression vector, expressing it in a suitable host, and measuring the enzyme activity of each expression product by a method described later in the Examples.

As described above, a polynucleotide having the nucleotide sequence encoding the protein (B), and the polynucleotide (b), desirably keep about at least half of the enzyme activity of a protein having the amino acid sequence of SEQ ID NO:1, more preferably 80% or more, still more preferably 90% or more of the transglycosylation activity.

The DNA having the nucleotide sequence in SEQ ID NO:1 may be obtained from chromosomal DNA of *Bifidobacterium longum* JCM1217 or from a DNA library by PCR (polymerase chain reaction; see White, T. J. et al. in Trends Genet. 5, 185 (1989)) or by hybridization. The primers used in PCR may be designed based on an internal amino acid sequence determined on the basis of, for example, the purified protein having a peptide synthesizing activity. As PCR primers, those having sequences corresponding to the 5'-non-translating region and 3'-non-translating region respectively may be used to amplify a full-length coding region of the present protein.

The primers may be synthesized in a usual manner according to, for example, the phosphoamidite method (see Tetrahedron Letters (1981), 22, 1859) in a DNA synthesizer model 380B manufactured by Applied Biosystems. The PCR reaction may be carried out using, for example, Gene Amp PCR system 9600 (supplied from PERKIN ELMER) and TaKaRa La PCR in vitro Cloning Kit (supplied from TAKARA BIO INC.) by a method prescribed by a supplier such as each manufacturer.

Furthermore, for homologues of the protein having transglycosylation activity derived from *Bifidobacterium longum* JCM1217, nucleotide sequences for the protein in Example (8-4) below were specified by the present inventors.

The sugar chain donor used in the transglycosylation method of the present invention may be a compound having a Galβ1-3GalNAc group as a sugar chain, and examples may include mucin, a protein having a Galβ1-3GalNAc group as a sugar chain, more specifically a protein having a structure where a disaccharide Galβ1-3GalNAc is bound at the α-position to serine or threonine, as well as Galβ1-3GalNAc group-containing p-nitrophenol (referred to hereinafter as Galβ1-3GalNAc α1-pNP; p-Nitrophenol is referred to as pNP).

The sugar chain acceptor used in the transglycosylation method of the present invention includes, for example, monosaccharides, oligosaccharides, alcohols (1-alkanol), amino acids and polypeptides, preferably saccharides such as monosaccharides and oligosaccharides, more preferably glucose, galactose, mannose, and arabinose.

In one preferable embodiment of the transglycosylation method of the present invention, a transformant expressing the protein is prepared and used in the transglycosylation method. That is, transformed cells into which a polynucleotide encoding the protein (A) or (B) described above, or the polynucleotide (a) or (b) described above, was introduced are cultivated in a medium to accumulate a protein having an endo-α-N-acetylgalactosaminidase activity and a transglycosylation activity in the medium and/or the transformed cells thereby supplying the protein to the reaction system for transglycosylation.

As the host for expressing the protein specified by the polynucleotide having the nucleotide of SEQ ID NO:1, it is possible to use various procaryotic cells including bacteria of the genus *Escherichia*, such as *Escherichia coli*, those of the genus *Empedobacter*, those of the genus *Sphingobacterium*, those of the genus *Flavobacterium*, and *Bacillus subtilis*, as well as various eucaryotic cells including *Saccharomyces cerevisiae, Pichia stipitis*, and *Aspergillus oryzae*.

A recombinant DNA used in introducing the DNA having the nucleotide sequence in SEQ ID NO:1 into a host can be prepared by inserting the DNA into a vector compatible with the host in such a form that the protein encoded by the DNA can be expressed. When a promoter inherent in the gene encoding the above protein derived from *Bifidobacterium longum* acts in the intended host cell, the promoter may be used for expressing the protein. If necessary, another promoter working in the host cell may be ligated to the DNA of SEQ ID NO:1 and expressed under its control.

The transformation method of introducing a recombinant such as an expression vector into a host cell may include the D. M. Morrison method (Methods in Enzymology 68, 326 (1979)), a method that involves treating a recipient microbial cell with calcium chloride to increase the permeability of DNA (Mandel, M. and Higa, A., J. Mol. Biol., 53, 159 (1970)).

The transglycosylation method of the present invention is used preferably in modifying foods, pharmaceutical preparations and various physiologically active substances. In a preferable embodiment of the method of modifying a food or pharmaceutical preparation, a sugar chain is transferred and added to a part or the whole of a component incorporated into the food or pharmaceutical preparation, to produce a modified food or pharmaceutical preparation containing the component having the sugar chain added thereto. The component to which the sugar chain is to be added is a sugar chain acceptor. Preferable examples of the sugar chain acceptor and donor include those described above.

In accordance with the method for transglycosylation of the present invention, a desirable compound including a sugar chain, a sugar alcohol and a glycoprotein (including a sugar-amino acid compound and a sugar-polypeptide compound) may be produced.

EXAMPLES

Hereinafter, the present invention is described in more detail with reference to the following Examples, but the present invention is not limited thereto.

(1) Analysis of Sugar Chain by TLC (Thin Layer Chromatography)

TLC was performed by using Silica gel 60 (MERCK) as the plate with a mixture of developing solvents of chloroform/methanol/water (3/3/1) and a coloration reagent with the composition shown in Table 1.

TABLE 1

| Acetone | 10 ml |
| Aniline | 100 μl |
| Diphenylamine | 0.1 g |
| Phosphoric acid | 1 ml |

(2) Analysis of a Reaction Product by HPLC (High Performance Liquid Chromatography)

A reaction mixture was subjected to HPLC (supplied from Hitachi D-7420 UV-VIS Detector, D-7100 Pump, D-7500 Integrator) to analyze the reaction product. Analysis was performed under the following conditions according to a manual attached to the apparatus. A normal-phase column was used with Solvent A/Solvent B (25/75) as the solvent.

| Column; | TSK-gel amide-80 |
|---|---|
| Solvent A; | 100% $H_2O$ |
| Solvent B; | 100% $CH_3CN$ |
| Column temp; | 40° C. |
| Flow rate; | 1 mL/min |
| Wavelength; | 214 nm |

(3) Determination of Enzyme Activity

(3-1) Determination of Hydrolysis Activity

The enzymatic reaction was performed using Galβ1-3GalNAcα1-pNP was used as the substrate, and liberated pNP (p-nitrophenol) was quantified colorimetrically under alkali conditions. Specifically, a sample was reacted at 37° C. for a predetermined time, and $Na_2CO_3$ was added to terminate the reaction, followed by measurement of the absorbance at 400 nm. The composition of the reaction solution is shown below (Table 2). When another substrate was used to examine substrate specificity, it was used at the same concentration as that of Galβ1-3GalNAcα1-pNP below.

TABLE 2

| 10 mM Galβ1-3GalNAcα1-pNP | 0.5 µl |
|---|---|
| 1M acetate buffer (pH 5.0) | 1.0 µl |
| Water | 16 µl |
| Enzyme | 2.5 µl |
| + | |
| $Na_2CO_3$ | 30 µl |

Figure 2:
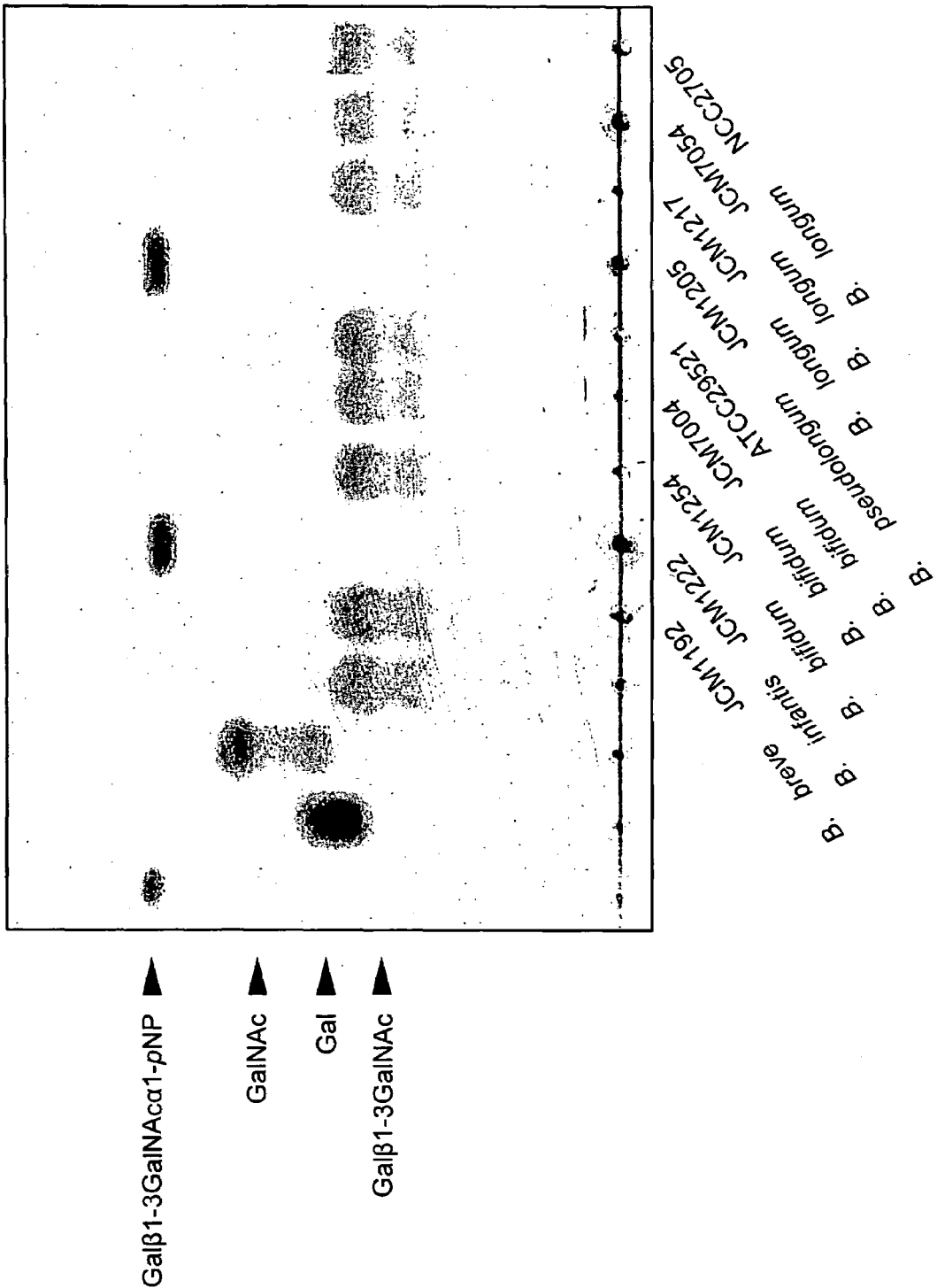
FIG. 2 shows the results of measurement of hydrolysis activity.

One unit was defined as the amount of the enzyme necessary to release 1 µmol pNP at 37° C. per minute, and the activity was acquired according to the following equation (I):

$$\text{Units/ml} = A/(18.3\ TV) \quad (I),$$

wherein
A=absorbance (nm)
T=reaction time (min)
V=amount of the enzyme in the total volume including the termination solution
18.3=millimolar absorptivity coefficient of pNP at pH 10 or more Various bifidobacteria were examined by using galactosyl β1→3N-acetylgalactosaminyl α1-p-nitrophenol (Galβ1-3GalNAc α1-pNP) as the substrate, to determine whether they had the activity of the present enzyme or not. The bifidobacteria were cultivated by stationary culture in GAM bouillon (supplied from Nissui Pharmaceutical) at 37° C. for 24 hours under anaerobic conditions. When the reaction solution was subjected to TLC, the activity of the present enzyme in decomposing the substrate not into monosaccharide units but into disaccharide units was recognized in many strains, as shown in FIG. 2. In FIG. 2, the 4th lane (Galβ1-3GalNAc) from the left is a control of disaccharide obtained by cutting the same substrate with an enzyme derived from a bacterium of the genus *Bacillus* known as an endo-α-N-acetylgalactosaminidase-producing bacterium.

With respect to this reaction product and GalNAc, it appears that there are two separated spots, but this is estimated due to a difference in anomer. The present inventors separately confirmed that one spot appeared when a developing solvent and coloration reagent different from those described above were used.

(3-2) Determination of Transglycosylation Activity

The present enzyme derived from *Bifidobacterium longum* JCM1217 was examined for its transglycosylation activity in the following manner. In the reaction system for determining the transglycosylation activity, the pNP substrate was used as the sugar chain donor in every case. The reaction was performed using the sugar chain donor (final concentration, 2 mM), the acceptor (final concentration, 1 M) and the enzyme (recombinant endo-α-GalNAc-ase, final concentration, 61 units/L) in a 10 mM acetate buffer, pH 5.0. After the reaction was conducted at 37° C. for 20 minutes, the reaction mixture was boiled for 3 minutes to inactivate the enzyme, then passed through a filter at 4° C. and subjected to HPLC. The degree of transglycosylation was acquired by the following equation (II):

$$\text{Degree of transglycosylation (\%)} = (\text{Area of transglycosylation product peak}/(\text{Area of hydrolysis product peak} + \text{Area of transglycosylation product peak})) \times 100 \quad (II)$$

Figure 3:
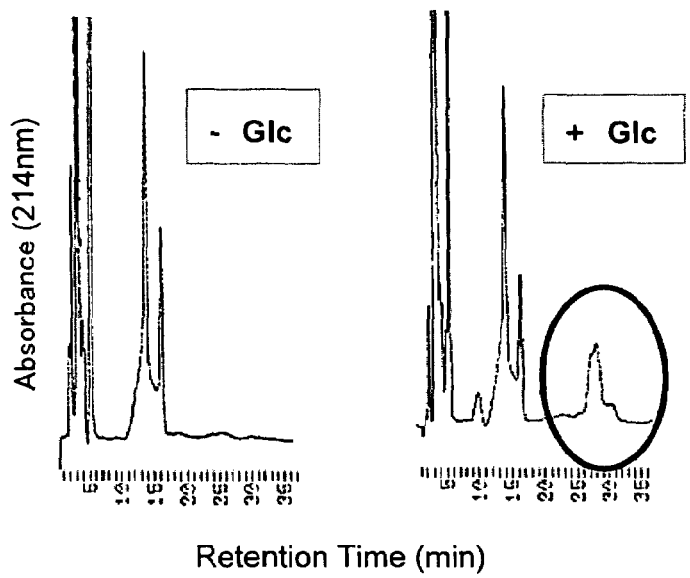
FIG. 3 shows the results of measurement of transglycosylation activity.

The reaction was carried out by using glucose as the acceptor and Galβ1-3GalNAcα1-pNP as the sugar chain donor, and the reaction solution was subjected to HPLC. The results are shown in FIG. 3. The left chromatograph (−Glc) is the glucose-free control, and the right chromatograph (+Glc) is the reaction solution. In the right chromatograph (+Glc), a new peak shown as the enclosed region was detected, and thus this region was isolated and analyzed by MALDI-TOF-MS (matrix assisted laser desorption ionization (MALDI); time of flight (TOF); mass spectrometry (MS)).

As a result, a peak indicating a trisaccharide having Glc added to Gal-GalNAc released from the sugar chain donor was obtained, thus revealing that the isolated enzyme had transglycosylation activity. The same HPLC analysis revealed that the sugar chain was also transferred to galactose, mannose and arabinose. The degree of transglycosylation to each acceptor under the predetermined reaction conditions is also shown (Table 3). The degree of transglycosylation to galactose, particularly to mannose, was lower than to glucose. It is estimated that a hydroxyl group at the 2- or 4-position is involved in the transglycosylation reaction.

TABLE 3

| Sugar chain acceptor | Degree of transglycosylation (%) |
|---|---|
| Glucose | 19.7 |
| Galactose | 8.3 |
| Mannose | 2.5 |
| Arabinose | 18.0 |
| Maltose | 14.4 |

(4) Method of Cultivating *E. coli*

As the medium used, a liquid medium LB broth (supplied from DIFCO) was used, and when an agar medium was used, the medium was prepared by adding agar at a final concentration of 2% to the above liquid medium. When ampicilin was used, it was added to a final concentration of 150 µm/ml.

(5) Construction of Expression Plasmid

On the basis of the nucleotide sequence of ORF encoding protein BL0464 of unknown functions, which was estimated as Endo-α-GalNAc-ase in *Bifidobacterium longum* NCC2705, primers capable of amplifying it by PCR were designed (Table 4). A restriction enzyme site was integrated in the primer to facilitate cloning. Using *Bifidobacterium longum* JCM1217 genome as a template, PCR was conducted using TaKaRa Ex Taq™ DNA Polymerase (supplied from TAKARA BIO INC.) in a reaction solution having the following composition and under the following conditions.

Composition of the reaction solution: template DNA, 0.01 to 0.1 µg; 2.5 units TaKaRa Ex Taq™ DNA Polymerase; 10 µL 10× Ex Taq™ buffer (supplied from TAKARA BIO INC.); 0.2 mM dNTP mixture (supplied from TAKARA BIO INC.); and 1 µM primers.

Reaction conditions: 94° C., 30 seconds→(94° C., 30 seconds→60° C., 30 seconds→72° C., 6 minutes)×30 cycles→72° C., 6 minutes.

TABLE 4

| | | |
|---|---|---|
| BL0464 forward primer (NcoI-endo-α-GalNAc-ase) | 5'-TTAACCTCCATGGGCAGCGGGGGAGG-3' | SEQ ID NO; 13 |
| BL0464 reverse primer (Endo-α-GalNAc-ase-His$_6$-tag-NotI) | 5'-AACCTGCGGCCGCCAGTTGCTCGCGATTGC-3' | SEQ ID NO; 14 |

The resulting PCR amplification product (about 6 kbp) was subjected to TA cloning, and then cleaved with restriction enzymes Nco I (supplied from Toyobo) and Not I (supplied from Toyobo) simultaneously, and the resulting fragment (about 6 kb) was inserted between Nco I/Not I sites in *E. coli* expression vector pET-23d(+) (supplied from Novagen). Ligation was carried out using Ligation High (supplied from TAKARA BIO INC.).

(6) Transformation of *E. coli*

Transformation of *E. coli* was conducted by adding the ligation reaction solution (about 20 µL) to competent cells (100 to 200 µL) then giving heat shock to the cells at 42° C. for 45 seconds, adding 800 to 900 µL SOC medium to the cells and cultivating the cells at 37° C. for 1 hour. The resultant culture was suitably diluted and applied onto an antibiotic-containing LB agar plate, and whether transformation occurred or not was confirmed by subjecting the growing *E. coli* to colony PCR, or by plasmid extraction and subsequent treatment with restriction enzymes. In extraction of the plasmid, Wizard plus SV Minipreps (supplied from Promega) was used. The *E. coli* competent cells were prepared by the Inoue method and stored at −80° C.

(7) Expression and Purification of Recombinant Endo-α-GalNAc-ase

*E. coli* BL21 (DE3)/pET-23d-Endo-α-GalNAc-ase was subjected to shake culture in LB-ampicilin medium at 37° C. until the OD600 of the culture reached 0.4, and then IPTG was added at a final concentration of 0.4 mM, and shake culture was continued for 3 hours, whereby the desired Endo-α-GalNAc-ase was expressed in a large amount. The bacterial cells were collected and used to prepare a cell-free extract fraction with Bug Buster reagent (supplied from Novagen), and its activity was confirmed.

For purification, the cell-free extract fraction was added to a nickel column HiTrap™ Chelating HP (supplied from Amersham) previously equilibrated with a buffer (2 mM Tris-HCl buffer (pH 8.0), 0.5 M NaCl) containing 5 mM imidazole, and an excess of protein in the column was washed away with the same buffer containing 5 mM imidazole, and subsequently the column was connected to FPLC. In FPLC, a buffer containing 20 mM imidazole, in an amount of 10 cv (column volume), was passed through the column and then the desired Endo-α-GalNAc-ase was eluted with a buffer containing 5 cv 1 M imidazole. The eluted fractions were dialyzed against a 10 mM KPB buffer, pH 7.0, and the desired Endo-α-GalNAc-ase was identified by activity measurement and SDS-PAGE.

(8) Analysis of DNA Sequence

Gene manipulation was carried out mainly in accordance with the method of Sambrook et al. The analysis of DNA sequence was carried out according to the method of Sanger et al. by using BigDye terminator v3.0 cycle sequencing ready reaction kit and ABI prism™ 310 NT genetic analyzer (Applied Biosystems).

The full-length nucleotide sequence of ORF encoding the Endo-α-GalNAc-ase in the genome of *Bifidobacterium longum* JCM1217 was determined.

(8-1) Sequence of the Gene Fragment Integrated in the Vector

For sequencing of the whole region of the desired gene fragment integrated in the vector, a primer binding region in the vector was utilized, and using T7 promoter primer and M13 reverse primer, sequences at both ends of the gene fragment were decoded. On the basis of the revealed sequences, primers directing towards the inside of the gene fragment were designed to advance decoding. By repeating this procedure, the nucleotide sequence of the whole region of the gene fragment integrated in the vector was determined. Given the gene fragment integrated in the vector, PCR amplification was initiated from the primer sequence, and thus the N-terminal region and C-terminal region of full-length ORF encoding Endo-α-GalNAc-ase derived from *Bifidobacterium longum* JCM1217 could not be completely determined.

(8-2) Sequence of C-terminal Region

To utilize homology among *Bifidobacterium longum* species, a primer (BL0464-C152 reverse primer: 5'-TGCGATTCATCGCCTAGCAG-3' (SEQ ID NO:15)) corresponding to the slightly outside of the C-terminus to the inside of ORF was designed on the basis of information on a nucleotide sequence of *Bifidobacterium longum* NCC2705. This primer, and the primer in Endo-α-GalNAc-ase gene fragment integrated in the vector, were used for PCR with *Bifidobacterium longum* JCM1217 genome as the template thereby to amplify the gene fragment containing the C-terminal region, which was then subjected to TA cloning using T easy vector. By sequencing, the nucleotide sequence of the complete C-terminal region in ORF encoding Endo-α-GalNAc-ase derived from *Bifidobacterium longum* JCM1217 was determined.

(8-3) Sequence of N-terminal Region

Because the outside of the N-terminus was composed of a repeat region, a suitable primer could not be designed, so that by using Southern blotting, a group of N-terminal region-containing gene fragments was obtained by restriction enzyme treatment from the genome of *Bifidobacterium longum* JCM1217. A vector having such fragment ligated therein was transformed into a competent cell. From the growing *E. coli*, positive clones were selected by colony PCR. By sequencing, the nucleotide sequence of the complete N-terminal region in ORF encoding Endo-α-GalNAc-ase derived from *Bifidobacterium longum* JCM1217 was determined.

(8-4)

On the basis of the information on the nucleotide sequence or amino acid sequence of the protein specified in *Bifidobacterium longum* JCM1217, homologue sequences were specified in the following microbial strains. Each microbial strain and the sequence number of its nucleotide sequence are shown. Each sequence can be searched from a database such as DDBJ (DNA Data Bank of Japan) by using each accession number etc.

*Streptococcus pneumoniae* R6 (Accession No. AE008413); SEQ ID NO:3
*Bifidobacterium longum* NCC2705 (Accession No. AE014666); SEQ ID NO:5
*Clostridium perfringens* str.13 (Accession No. AP003187); SEQ ID NO:7
*Streptomyces coelicolor* A3 (2) (Accession No. AL939127); SEQ ID NO:9
*Enterococcus faecalis* V583 (Accession No. AE016952); SEQ ID NO:11

(9) Transglycosylation Into 1-alkanol

Figure 4A:
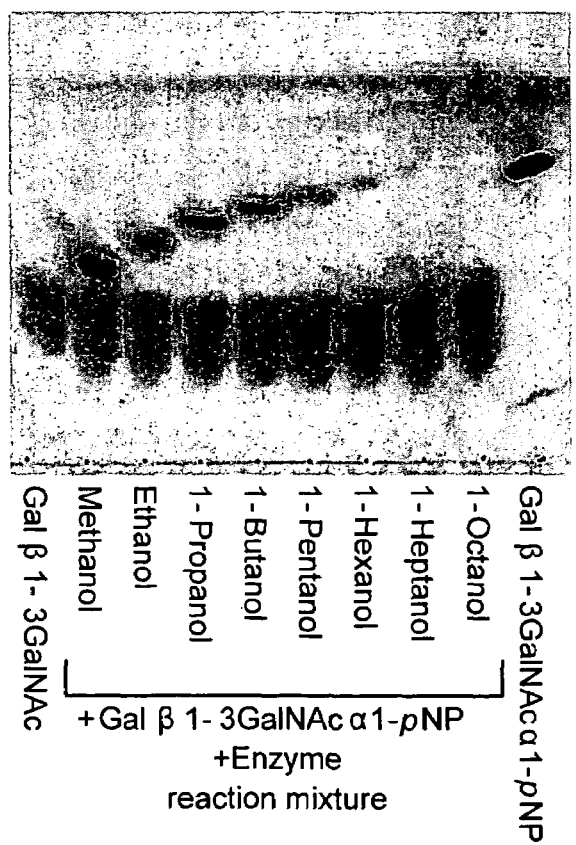
In FIG. 4A, the transglycosylation experiment described in Example (3-2) was performed with various kinds of 1-alkanol as the acceptor. The reaction system for measurement of transglycosylation activity was carried out by using the sugar chain donor Galβ1-3GalNAcα1-pNP, the acceptor 1-alkanol and the purified enzyme (recombinant endo-α-GalNAc-ase). After the reaction, the reaction solution was spotted on a TLC plate, developed with a mixture of solvent of chloroform/methanol/water, and colored with naphthoresorcinol in sulfuric acid.

The transglycosylation experiment described in Example (3-2) was performed with various kinds of 1-alkanol as the acceptor. The reaction system for measurement of transglycosylation activity was carried out by using the sugar chain donor Galβ1-3GalNAcα1-pNP at a final concentration of 2 mM, the acceptor 1-alkanol at a final concentration of 15% (v/v) and the purified enzyme (recombinant endo-α-GalNAc-ase) at a final concentration of 6.8 units/L in a 50 mM potassium phosphate buffer, pH 7.0. After the reaction at 37° C. for 60 minutes, 3 μl of the reaction solution was spotted on a TLC plate, developed with a mixture of solvent of chloroform/methanol/water (7/6.2/2), and colored with naphthoresorcinol in sulfuric acid (0.2% (w/v) naphthoresorcinol in sulfuric acid:ethanol (5:95 (v/v)). The results are shown in FIG. 4A. As shown in the drawing, when 1-alkanol was added as the acceptor, new spots were detected in addition to Galβ1-3GalNAc as a hydrolysis product of the sugar chain donor, and these spots were detected at different mobility depending on the type of 1-alkanol. Therefore it was considered that the spots was due to the substance of Galβ1-3GalNAc transferred to each alkanol.

Figure 4B:
In FIG. 4B, using methanol as the sugar chain acceptor, the reaction with Galβ1-3GalNAc and the reaction with Galβ1-3GalNAcα1-pNP were conducted respectively in order to confirm whether the formation of these substances by the enzyme reaction was due to the transglycosylation reaction or due to the reverse reaction of hydrolysis reaction.

Using methanol as the sugar chain acceptor, the reaction with Galβ1-3GalNAc and the reaction with Galβ1-3GalNAcα1-pNP were then carried out respectively in order to confirm whether the formation of these substances by the enzyme reaction was due to the transglycosylation reaction or due to the reverse reaction of hydrolysis reaction. The reaction conditions were the same as described above except that Galβ1-3GalNAc and Galβ1-3GalNAcα1-pNP were used at a final concentration of 1.2 mM respectively. The results are shown in FIG. 4B. As shown in the drawing, the spot formed in FIG. 4A was not formed in the reaction of Galβ1-3GalNAc with methanol, but formed in the reaction of Galβ1-3GalNAcα1-pNP with methanol, thus revealing that the products were formed not by the reverse reaction of hydrolysis reaction but by the transglycosylation reaction.

(10) Transglycosylation Into Polypeptide

The transglycosylation activity by endo-α-N-acetylgalactosaminidase (endo-α-GalNAc-ase) when using various polypeptides as the sugar chain acceptor was examined.

(10-1) Enzymatic Reaction

First, an enzymatic reaction of recombinant endo-α-GalNAc-ase purified in (7) was performed with Galβ1-3GalNAcα1-pNP as the sugar chain donor and peptide-T (see SEQ ID: 16), PAMP-12 (an amino acid sequence shown in SEQ ID: 17 with an amino group attached at C-end of the sequence) and bradykinin (see SEQ ID: 18) as the sugar chain acceptor.

That is, 10 μl of Galβ1-3GalNAcα1-pNP, 6 μl solution of each polypeptide as the acceptor and 1.5 μl of NaP (sodium phosphate) buffer (500 mM, pH 6) were mixed. The sugar chain donor, Galβ1-3GalNAcα1-pNP was used at a concentration of 10 mM, and for the peptide solution, each of 50 mM peptide-T, 50 mM bradykinin, and 10 mM PAMP-12 was used. A solution obtained by mixing was warmed up to 37° C., subsequently 2.5 μl of endo-α-GalNAc-ase (1.55 unit/ml) was added thereto, which was then incubated in a water bath at 37° C. for one hour. Subsequently, the enzyme was inactivated by boiling for 3 to 5 minutes.

(10-2) Analysis and Fractionation by HPLC

Each reaction solution obtained in the aforementioned enzymatic reaction was applied to an HPLC analysis, and reaction products were analyzed and fractionated. For both the analysis and fractionation, Pump L-7100, UV-VIS Detector L-7240 and Integrator D-7500 suppled from Hitachi were used an HPLC apparatus system, and COSMOSIL 5C$_{18}$-AR-II column (nakalai tesque): 10×250 mm was used as a column. An elution was performed under a condition of a temperature at 40° C. using 0 to 25% acetonitrile (0.1% trifluoroacetic acid) as a solvent. UV (wavelength 214 nm) spectra were detected.

Figure 5A:
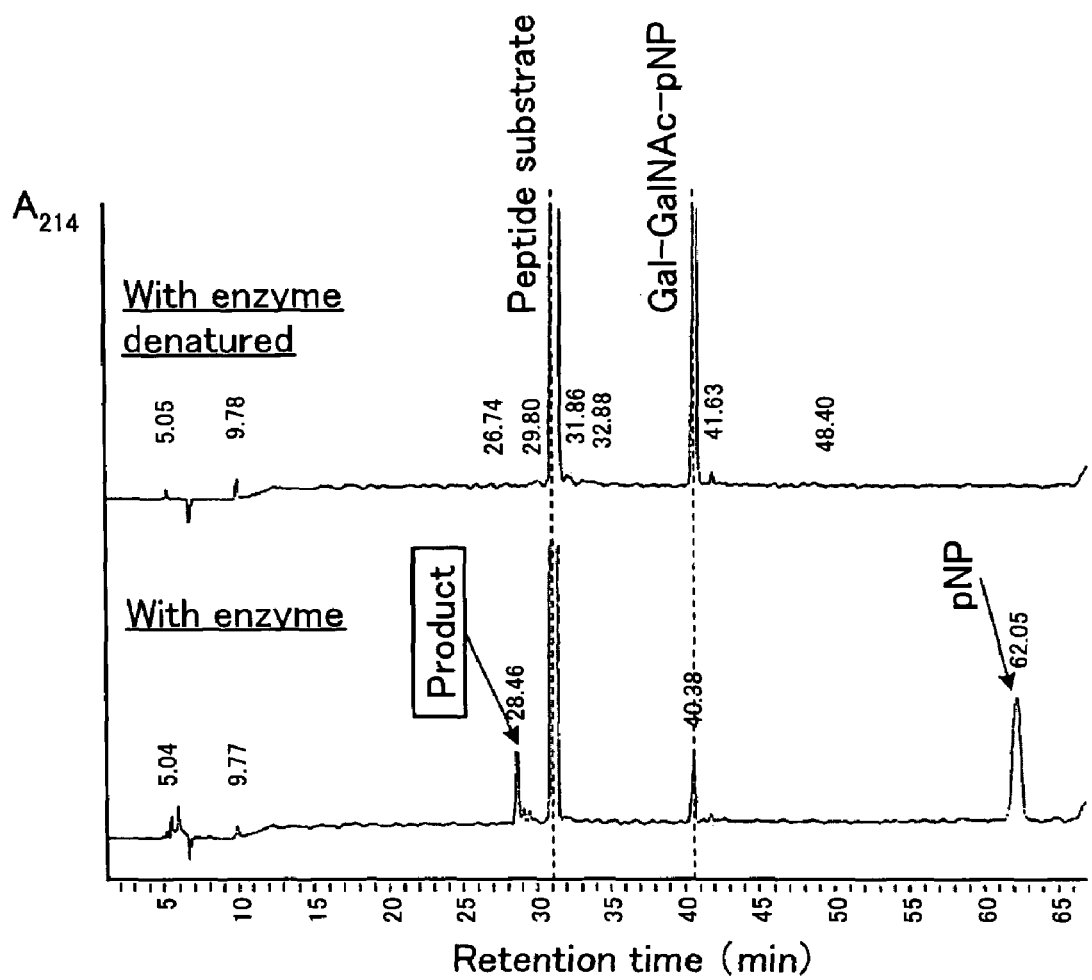
FIG. 5 shows the results of transglycosylation activities on peptide-T, PAMP-12 and bradykinin measured by HPLC. Detected results of each reaction solution for peptide-T, PAMP-12 and bradykinin are shown in FIGS. 5A, 5B and 5C, respectively.
Figure 5B:
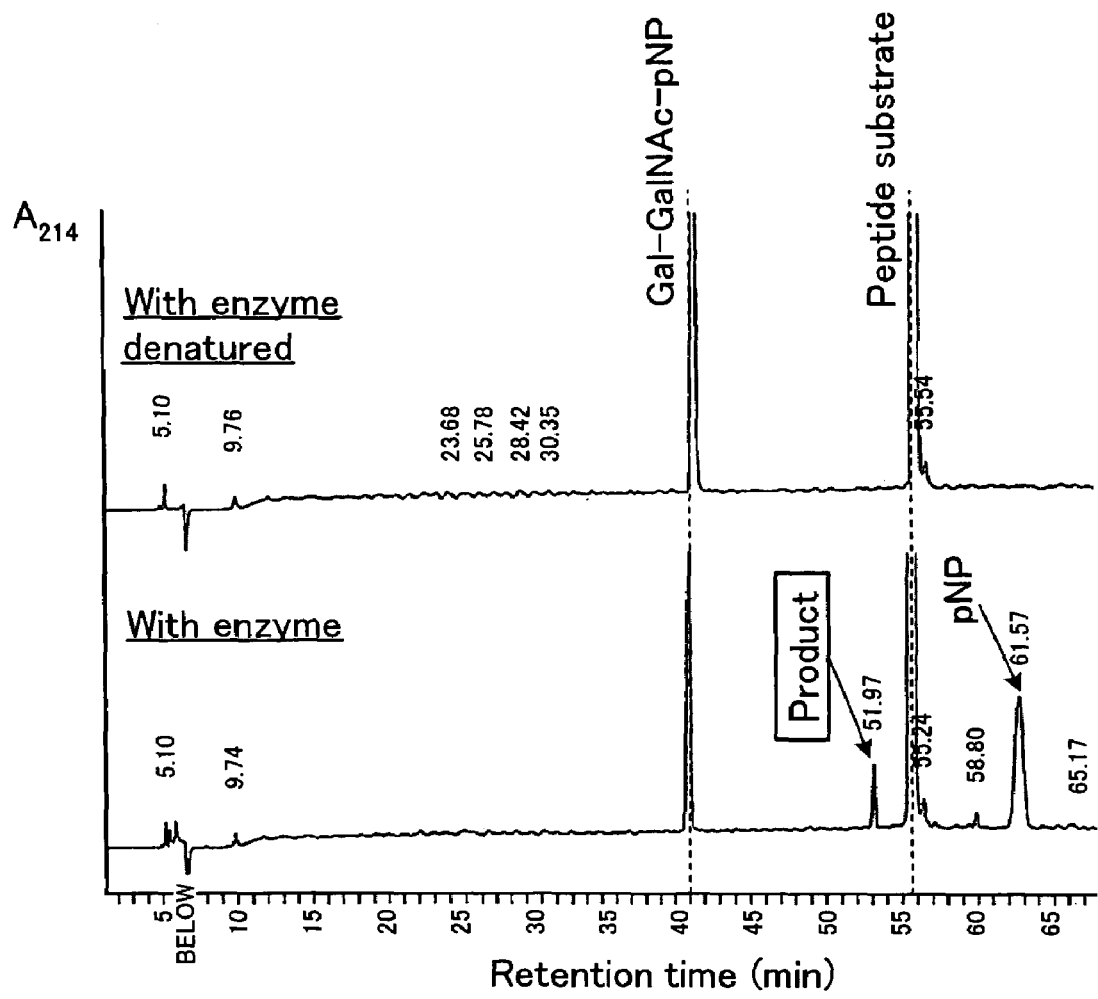
Figure 5C:
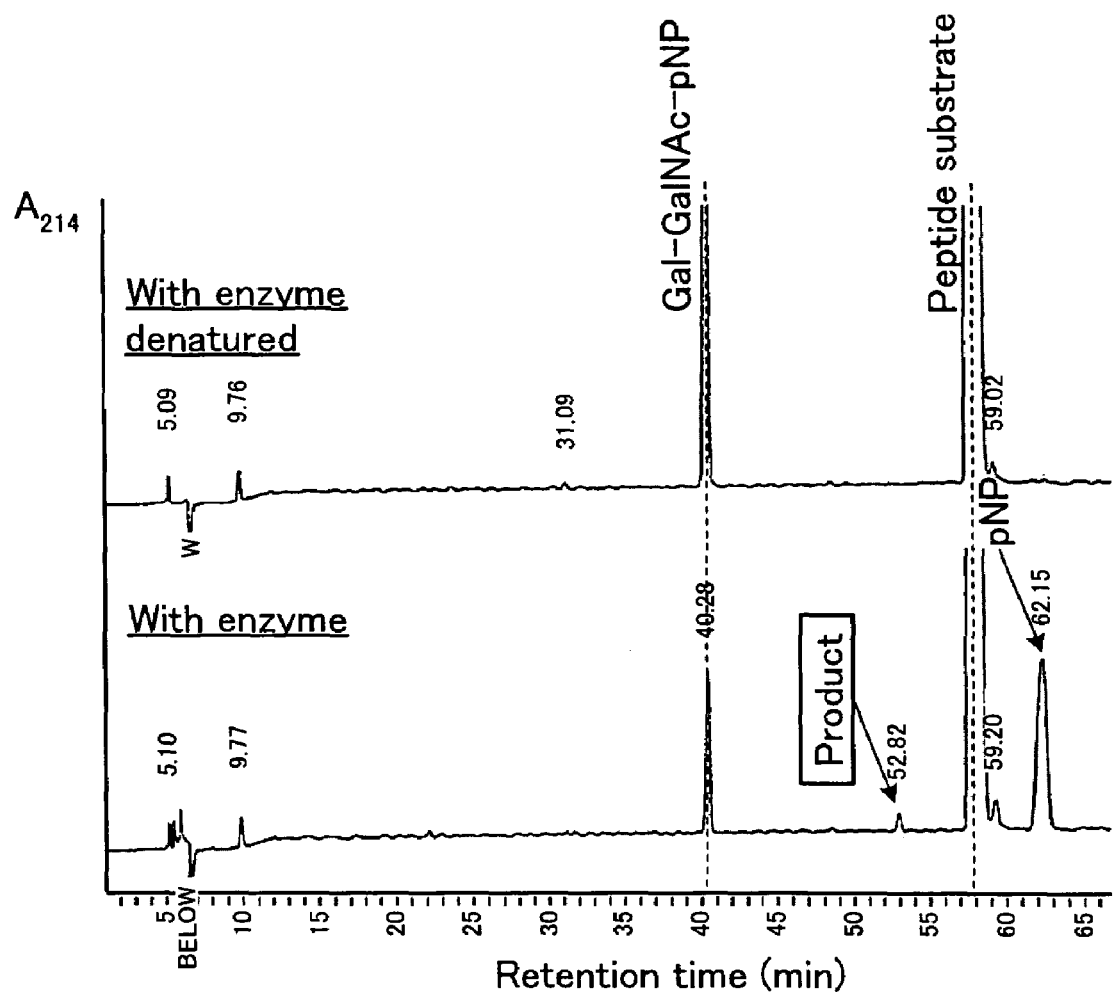

Detected results of each reaction solution for peptide-T, PAMP-12 and bradykinin are shown in FIGS. 5A, 5B and 5C, respectively. Lower chromatogram in each of FIGS. 5A, 5B and 5C shows the result of the experiment with the enzyme for each reaction solution obtained in the enzymatic reaction as described above. Upper chromatogram shows the result of the control with the denatured enzyme for each reaction solution obtained from the enzymatic reaction performed by adding the inactivated enzyme obtained by boiling the enzyme 5 minutes before the reaction, in place of the active enzyme.

As is evident from FIGS. 5A, 5B and 5C, it was demonstrated that the sugar chain was transferred to each peptide because peaks of transglycosylation products ("product" portion in each Figure) were observed. Thus, these peak portions (fractions) were fractionated and applied to the following analysis.

(10-3) Analysis by Mass Spectrometry (MS)

The fractions fractionated by the aforementioned HPLC were analyzed by MALDI-TOF-MS. BRUKER Daltons Autofex-G MALDI-TOF mass spectrometer was used as an MALDI-TOF-MS apparatus.

Figure 6A:
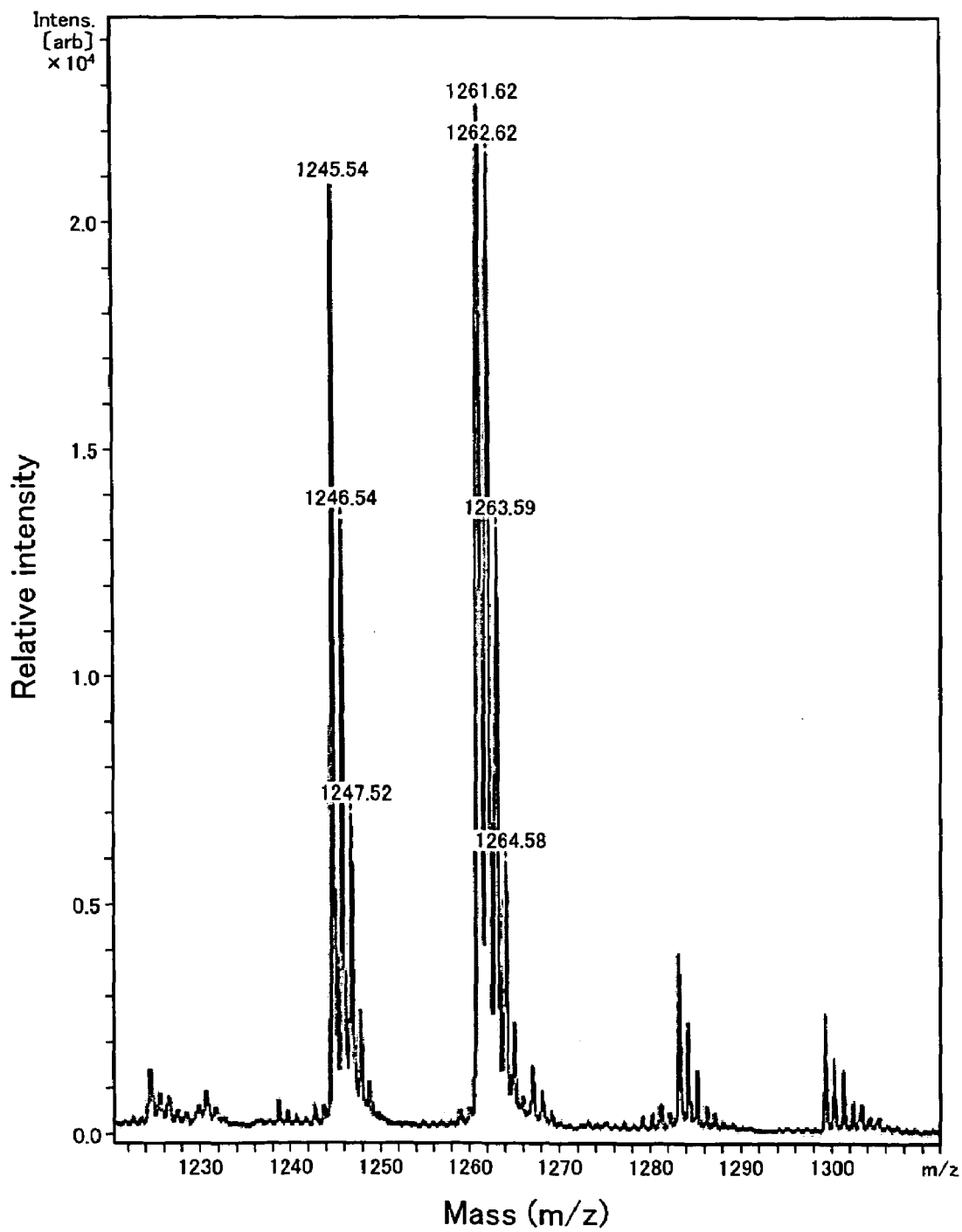
FIG. 6 shows a result of a transglycosylation activity on peptide-T, PAMP-12 and bradykinin measured by MALDI-TOF-MS. Detection results for MS spectra of the fractions fractionated from the reaction solutions of peptide-T, PAMP-12 and bradykinin are shown in FIGS. 6A, 6B and 6C, respectively.
Figure 6B:
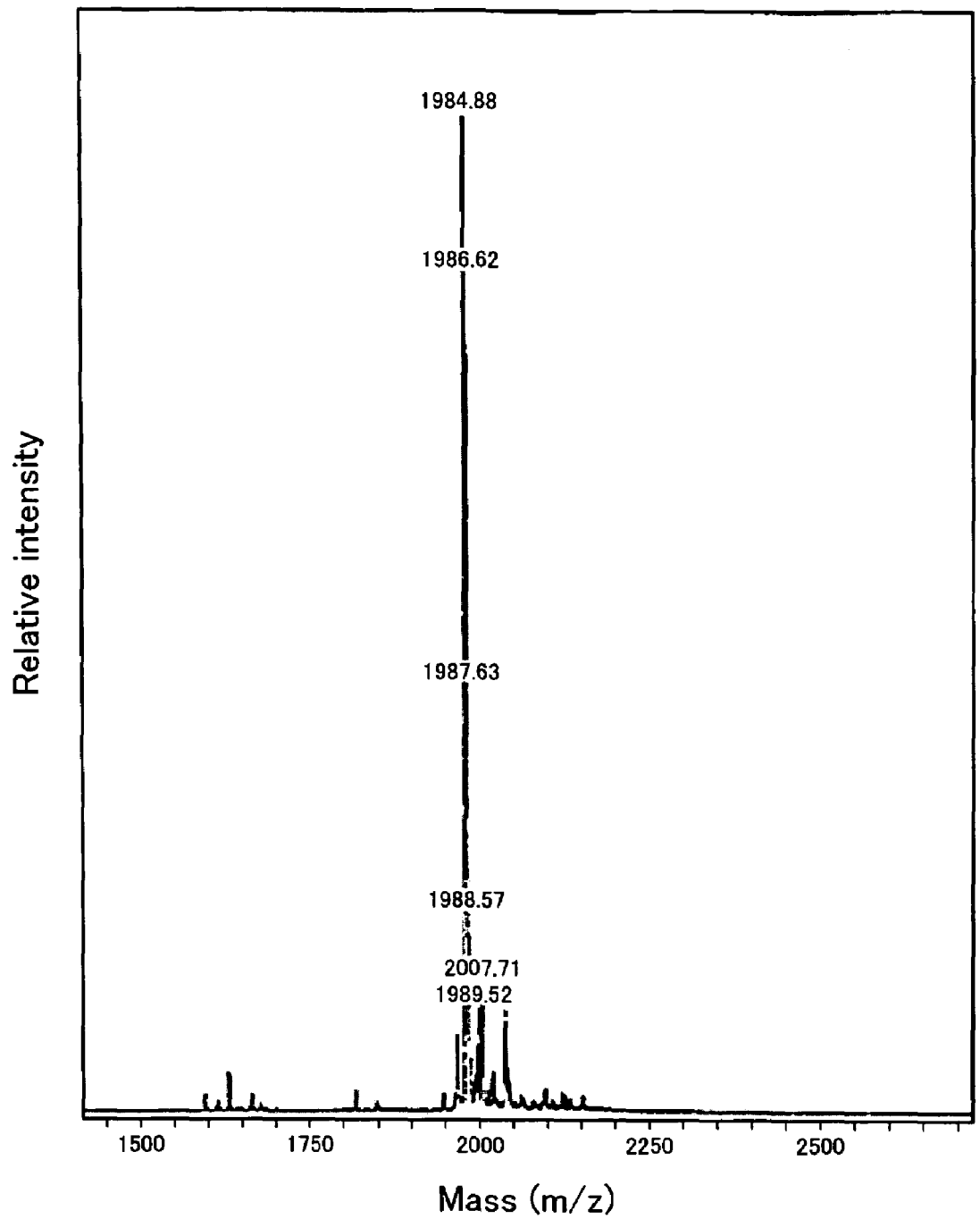
Figure 6C:
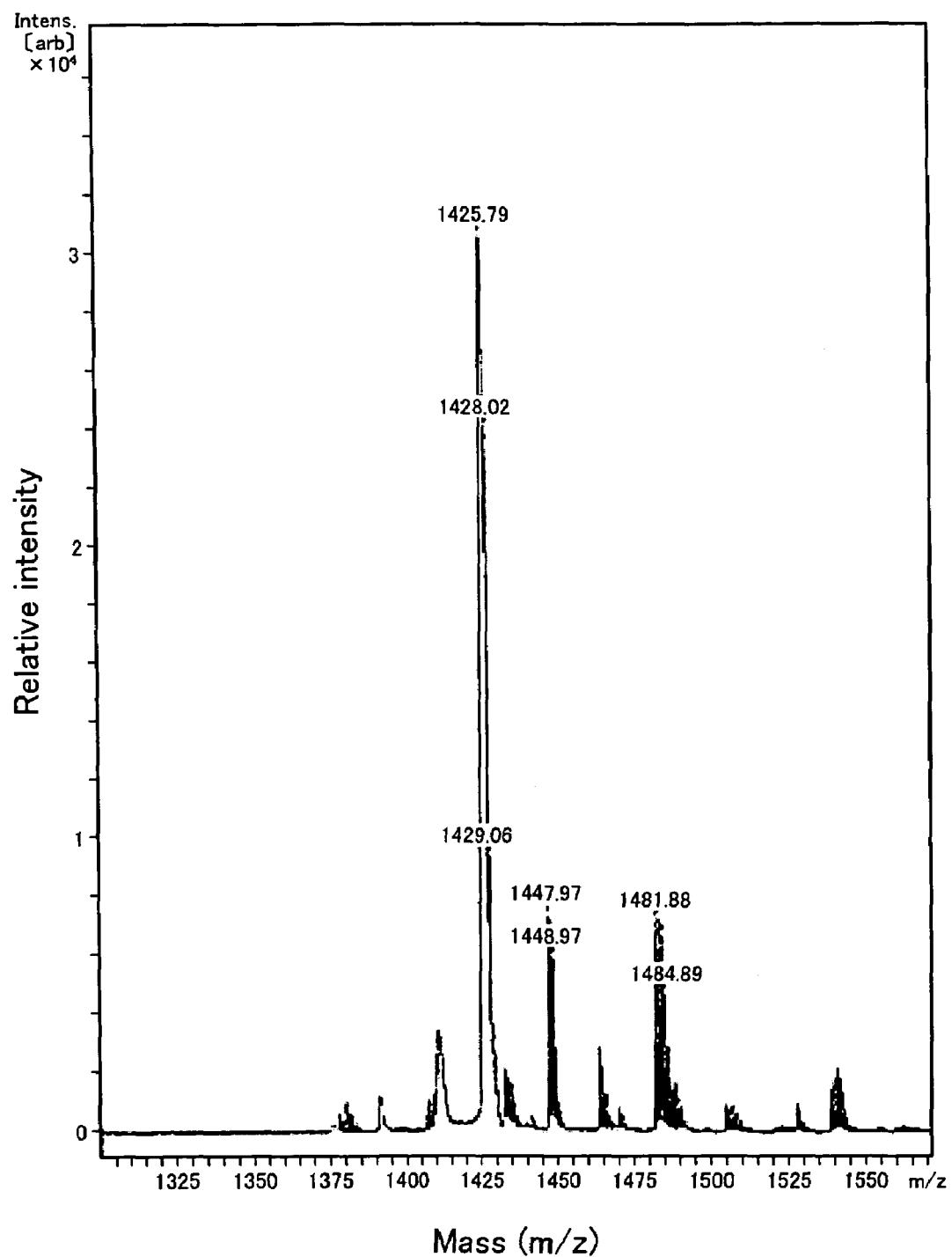

Detection results for MS spectra of the fractions fractionated from the reaction solutions of peptide-T, PAMP-12 and bradykinin are shown in FIGS. 6A, 6B and 6C, respectively. As is evident from FIGS. 6A, 6B and 6C, the peaks corresponding to those in which disaccharide (Gal-GalNAc) had been transferred were obtained for all of the peptides. Each peak was as follows: Peptide-T: 1245.54 (M+Na)$^+$, 1261.62 (M+K)$^+$; PAMP-12: 1984.68 (M+H)$^+$; Bradykinin: 1425.79 (M+H)$^+$.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims along with their full scope of equivalents.

What is claimed is:

1. A method for transglycosylation, comprising a reaction of transferring a galactosylβ1→3N-acetylgalactosaminyl group from a sugar donor containing a sugar chain having a galactosylβ1→3N-acetylgalactosaminyl group bound in the configuration of an α anomer, to a sugar chain acceptor, in the presence of a protein having endo-α-N-acetylgalactosaminidase activity and transglycosylation activity, wherein said protein is selected from the group consisting of:

(A) a protein having the amino acid sequence of SEQ ID NO:2, and (B) a protein having the amino acid sequence of SEQ ID NO: 2 including a total of one to thirty amino acids mutations in said amino acid sequence of SEQ ID NO: 2, the mutations being one or more selected from the group consisting of substitution, deletion, insertion, and addition, and wherein the protein exhibits endo-α-N-acetylgalactosaminidase activity and transglycosylation activity at a residual activity of at least 80% as compared to the protein having the amino acid sequence of SEQ ID NO: 2 at 50° C. and pH 8.

2. The method for transglycosylation according to claim 1, wherein the protein is obtained from a microorganism belonging to the genus *Bifidobacterium*.

3. The method for transglycosylation according to claim 1, wherein the protein is the protein having the amino acid sequence of SEQ ID NO:2.

4. The method for transglycosylation according to claim 1, comprising:
cultivating a transformed cell with a polynucleotide encoding the protein having endo-α-N-acetylgalactosaminidase activity and transglycosylation activity in a suitable medium for the expression of said protein and collecting said protein,
wherein the protein is selected from the group consisting of:
(A) a protein having the amino acid sequence of SEQ ID NO:2, and
(B) a protein having the amino acid sequence of SEQ ID NO: 2 including a total of one to thirty amino acids mutations in said amino acid sequence of SEQ ID NO: 2, the mutations being one or more selected from the group consisting of substitution, deletion, insertion, and addition, and wherein the protein exhibits endo-α-N-acetylgalactosaminidase activity and transglycosylation activity at a residual activity of at least 80% as compared to the protein having the amino acid sequence of SEQ ID NO: 2 at 50° C. and pH 8.

5. The method for transglycosylation according to claim 1, wherein the sugar chain acceptor is selected from the group consisting of a monosaccharide, an oligosaccharide, an alcohol, an amino acid and a polypeptide.

6. A method for producing a compound selected from the group consisting of a sugar chain, a sugar alcohol and a glycoprotein, said method comprising transferring a galactosylβ1→3N-acetylgalactosaminyl group from a sugar donor containing a sugar chain having a galactosylβ1→3N-acetylgalactosaminyl group bound in the configuration of an α anomer, to a sugar chain acceptor, in the presence of a protein having endo-α-N-acetylgalactosaminidase activity and transglycosylation activity, wherein said protein is selected from the group consisting of:
(A) a protein having the amino acid sequence of SEQ ID NO:2, and
(B) a protein having the amino acid sequence of SEQ ID NO: 2 including a total of one to thirty amino acids mutations in said amino acid sequence of SEQ ID NO: 2, the mutations being one or more selected from the group consisting of substitution, deletion, insertion, and addition, and wherein the protein exhibits endo-α-N-acetylgalactosaminidase activity and transglycosylation activity at a residual activity of at least 80% as compared to the protein having the amino acid sequence of SEQ ID NO: 2 at 50° C. and pH 8.

7. The method according to claim 6, wherein the protein is obtained from a microorganism belonging to the genus *Bifidobacterium*.

8. The method according to claim 6, wherein the protein is the protein having the amino acid sequence of SEQ ID NO:2.

9. The method according to claim 6, wherein said transferring further comprising:
cultivating a transformed cell with a polynucleotide encoding the protein having endo-α-N-acetylgalactosaminidase activity and transglycosylation activity in a suitable medium for the expression of said protein and collecting said protein.

10. The method according to claim 6, wherein said transferring further comprising:
cultivating a transformed cell with a polynucleotide encoding the protein having endo-α-N-acetylgalactosaminidase activity and transglycosylation in a suitable medium for the expression of said protein and collecting said protein, wherein said protein is obtained from a microorganism belonging to the genus *Bifidobacterium*.

11. The method according to claim 6, wherein the sugar chain acceptor is selected from the group consisting of a monosaccharide, an oligosaccharide, an alcohol, an amino acid and a polypeptide.

12. The method according to claim 1, wherein the protein is the protein having the amino acid sequence of SEQ ID NO: 2 including a total of one to thirty amino acids mutations in said amino acid sequence of SEQ ID NO: 2, the mutations being one or more selected from the group consisting of substitution, deletion, insertion, and addition, and wherein the protein exhibits endo-α-N-acetylgalactosaminidase activity and transglycosylation activity at a residual activity of at least 80% as compared to the protein having the amino acid sequence of SEQ ID NO: 2 at 50° C. and pH 8.

13. The method according to claim 1, wherein the protein is the protein having the amino acid sequence of SEQ ID NO: 2 including a total of one to ten amino acids mutations in said amino acid sequence of SEQ ID NO: 2, the mutations being one or more selected from the group consisting of substitution, deletion, insertion, and addition, and wherein the protein exhibits endo-α-N-acetylgalactosaminidase activity and transglycosylation activity at a residual activity of at least 80% as compared to the protein having the amino acid sequence of SEQ ID NO: 2 at 50° C. and pH 8.

14. The method according to claim 1, wherein the sugar chain acceptor is selected from the group consisting of a monosaccharide, an oligosaccharide, and an alcohol.

15. The method according to claim 1, wherein sugar chain acceptor is an alcohol and said alcohol is a 1-alkanol.

16. The method according to claim 6, wherein the sugar chain acceptor is selected from the group consisting of a monosaccharide, an oligosaccharide, and an alcohol.

17. The method according to claim 6, wherein sugar chain acceptor is an alcohol and said alcohol is a 1-alkanol.

18. The method according to claim 6, wherein the protein is the protein having the amino acid sequence of SEQ ID NO: 2 including a total of one to thirty amino acids mutations in said amino acid sequence of SEQ ID NO: 2, the mutations being one or more selected from the group consisting of substitution, deletion, insertion, and addition, and wherein the protein exhibits endo-α-N-acetylgalactosaminidase activity and transglycosylation activity at a residual activity of at least 80% as compared to the protein having the amino acid sequence of SEQ ID NO: 2 at 50° C. and pH 8.

19. The method according to claim 6, wherein the protein is the protein having the amino acid sequence of SEQ ID NO: 2 including a total of one to ten amino acids mutations in said amino acid sequence of SEQ ID NO: 2, the mutations being one or more selected from the group consisting of substitution, deletion, insertion, and addition, and wherein the protein exhibits endo-α-N-acetylgalactosaminidase activity and transglycosylation activity at a residual activity of at least 80% as compared to the protein having the amino acid sequence of SEQ ID NO: 2 at 50° C. and pH 8.

* * * * *

SEQUENCE LISTING

<160> NUMBER OF SEQ ID NOS: 18

<210> SEQ ID NO 1
<211> LENGTH: 5901
<212> TYPE: DNA
<213> ORGANISM: Bifidobacterium lomgum JCM1217
<220> FEATURE:
<221> NAME/KEY: CDS
<222> LOCATION: (1)..(5901)

<400> SEQUENCE: 1

```
atg aaa aag aag aag act ata tcg gct gcg ctg gca aca gcg tta gcc      48
Met Lys Lys Lys Lys Thr Ile Ser Ala Ala Leu Ala Thr Ala Leu Ala
1               5                   10                  15 tta acc tgc atg ggc agc ggg gga ggt act gcg ttc gca gtg ccc ctg      96
Leu Thr Cys Met Gly Ser Gly Gly Gly Thr Ala Phe Ala Val Pro Leu
            20                  25                  30 tct gat gct gac ttg cag act ttg gca agt cag att cag caa atc aac     144
Ser Asp Ala Asp Leu Gln Thr Leu Ala Ser Gln Ile Gln Gln Ile Asn
        35                  40                  45 gat act tct gat tct gca act gct tcc gag act cct tcc gca caa gcc     192
Asp Thr Ser Asp Ser Ala Thr Ala Ser Glu Thr Pro Ser Ala Gln Ala
    50                  55                  60 gat gcg gtt gaa ggc tgg act att gat tcc aac atc gct cag ggc ggc     240
Asp Ala Val Glu Gly Trp Thr Ile Asp Ser Asn Ile Ala Gln Gly Gly
65                  70                  75                  80 gaa atc ctg gag atg gca aac ggt tgg ctg cac ctc aag tcc act gcc     288
Glu Ile Leu Glu Met Ala Asn Gly Trp Leu His Leu Lys Ser Thr Ala
                85                  90                  95 tct aac ggt aat gcg gca gcg aac ccc agc tcc agc aac aac tgg ccg     336
Ser Asn Gly Asn Ala Ala Ala Asn Pro Ser Ser Ser Asn Asn Trp Pro
            100                 105                 110 gca gcc gta tgg ggc aca gat tac gac ttc tcc aag gcc ggc tcc     384
Ala Val Ala Val Trp Gly Thr Asp Tyr Asp Phe Ser Lys Ala Gly Ser
        115                 120                 125 ttc cac gcc acc atc aaa tcc ccg cag gaa ggc tcc gcc aac cgc ttc     432
Phe His Ala Thr Ile Lys Ser Pro Gln Glu Gly Ser Ala Asn Arg Phe
    130                 135                 140 ggc ttc tac ctg ggc tac aac gac ccg ggc agc ggc ctg ttc atc ggc     480
Gly Phe Tyr Leu Gly Tyr Asn Asp Pro Gly Ser Gly Leu Phe Ile Gly
145                 150                 155                 160 tac gat tcg ggc ggc tgg ttc tgg cag acc tac acc ggt ggc ggt agc     528
Tyr Asp Ser Gly Gly Trp Phe Trp Gln Thr Tyr Thr Gly Gly Gly Ser
                165                 170                 175 ggc agc tgg tac agc ggt gct cgt atc gct gct ccg agc gcc aac gaa     576
Gly Ser Trp Tyr Ser Gly Ala Arg Ile Ala Ala Pro Ser Ala Asn Glu
            180                 185                 190 gag cac gac att cgg gtc tcc tgg acc gac gcc aag gtc gcc aca ctg     624
Glu His Asp Ile Arg Val Ser Trp Thr Asp Ala Lys Val Ala Thr Leu
        195                 200                 205 acc gtg gat ggc cag aag gca ttc gat gtc gat tac tcc gca atg acg     672
Thr Val Asp Gly Gln Lys Ala Phe Asp Val Asp Tyr Ser Ala Met Thr
    210                 215                 220 aac ctc tcc aac aag ctt gcc atc aag gcc ggc tcc tgg aag gag ctg     720
Asn Leu Ser Asn Lys Leu Ala Ile Lys Ala Gly Ser Trp Lys Glu Leu
225                 230                 235                 240 aac gag gtc acc gac gtg tac atc aag gac ttc ccg gag gtt gtc gaa     768
Asn Glu Val Thr Asp Val Tyr Ile Lys Asp Phe Pro Glu Val Val Glu
                245                 250                 255
```

-continued

| | | |
|---|---|---|
| gcc gcc aag cac gcg gtt tcc ggc aag gtt gtg gac gct gga ggc gct<br>Ala Ala Lys His Ala Val Ser Gly Lys Val Val Asp Ala Gly Gly Ala<br>260 265 270 | | 816 |
| gcc att gaa ggc gca aca gtg cgt ttg gat aag acc aag gtg aag acc<br>Ala Ile Glu Gly Ala Thr Val Arg Leu Asp Lys Thr Lys Val Lys Thr<br>275 280 285 | | 864 |
| ggt gca gat ggc acc ttc tcc ttc gcc gac att gaa gaa ggc gaa cac<br>Gly Ala Asp Gly Thr Phe Ser Phe Ala Asp Ile Glu Glu Gly Glu His<br>290 295 300 | | 912 |
| acg ctt tcg att gcc aag gaa ggc tat gag gac gtc tcc cag cag gtg<br>Thr Leu Ser Ile Ala Lys Glu Gly Tyr Glu Asp Val Ser Gln Gln Val<br>305 310 315 320 | | 960 |
| acg gtc tcc ggc gcg gat ctt gcc atc gat ccc atc acc ctg aac aaa<br>Thr Val Ser Gly Ala Asp Leu Ala Ile Asp Pro Ile Thr Leu Asn Lys<br>325 330 335 | | 1008 |
| acc gtt cag gtc gcc tcc gaa acg ctg aag acc aag aag atg gaa gtt<br>Thr Val Gln Val Ala Ser Glu Thr Leu Lys Thr Lys Lys Met Glu Val<br>340 345 350 | | 1056 |
| cag att aag aag aac ttc ccc tct gtg ctg cag tac acg atg acc gac<br>Gln Ile Lys Lys Asn Phe Pro Ser Val Leu Gln Tyr Thr Met Thr Asp<br>355 360 365 | | 1104 |
| ggc aag gtg atg tac ggc cag tcc aag gat gtg cgc acc gtc gaa atc<br>Gly Lys Val Met Tyr Gly Gln Ser Lys Asp Val Arg Thr Val Glu Ile<br>370 375 380 | | 1152 |
| aac ggc acc aac atc gaa ctg ggc gat gac gac gtg acc ttc aag aag<br>Asn Gly Thr Asn Ile Glu Leu Gly Asp Asp Asp Val Thr Phe Lys Lys<br>385 390 395 400 | | 1200 |
| gtt tcc gac acc gag gcc acc tac acg ctg aag gtc aag gat gag gcc<br>Val Ser Asp Thr Glu Ala Thr Tyr Thr Leu Lys Val Lys Asp Glu Ala<br>405 410 415 | | 1248 |
| aag aag att gac gcg gtg atc acc gtt cag atc acg gtc aag gcc aac<br>Lys Lys Ile Asp Ala Val Ile Thr Val Gln Ile Thr Val Lys Ala Asn<br>420 425 430 | | 1296 |
| cag ctg cac ctc aac gtc acc aag atc aag aac aac ctg tcc gaa ggc<br>Gln Leu His Leu Asn Val Thr Lys Ile Lys Asn Asn Leu Ser Glu Gly<br>435 440 445 | | 1344 |
| att cct gag ggc aac ggt gtg gag gag aac gcc atc cag acg ctg tcc<br>Ile Pro Glu Gly Asn Gly Val Glu Glu Asn Ala Ile Gln Thr Leu Ser<br>450 455 460 | | 1392 |
| ttc ccg aac cag agt ctc gtt tcc gtg cgt tcc agc cag gaa aat gcc<br>Phe Pro Asn Gln Ser Leu Val Ser Val Arg Ser Ser Gln Glu Asn Ala<br>465 470 475 480 | | 1440 |
| caa ttc act ggt gct cgt atg tct tcc aac acg cag aag cct ggc gat<br>Gln Phe Thr Gly Ala Arg Met Ser Ser Asn Thr Gln Lys Pro Gly Asp<br>485 490 495 | | 1488 |
| acc aac ttc gca gtg acc gaa gat act aac gtc acc gat agc gac tac<br>Thr Asn Phe Ala Val Thr Glu Asp Thr Asn Val Thr Asp Ser Asp Tyr<br>500 505 510 | | 1536 |
| acc tac ggc ttc atc tcc ggt gct ggc ctg agt gcc ggc ctg tgg agc<br>Thr Tyr Gly Phe Ile Ser Gly Ala Gly Leu Ser Ala Gly Leu Trp Ser<br>515 520 525 | | 1584 |
| aac tcc gag cac gat ggc acc tat gtg gcg gct cct gtg cgc ggc ggc<br>Asn Ser Glu His Asp Gly Thr Tyr Val Ala Ala Pro Val Arg Gly Gly<br>530 535 540 | | 1632 |
| agc cag aac acg cgt gtc tac gcc acc acc cag cag act ggt gac gcc<br>Ser Gln Asn Thr Arg Val Tyr Ala Thr Thr Gln Gln Thr Gly Asp Ala<br>545 550 555 560 | | 1680 |
| acc tcc ctg ggc ctg gcc agc gct ccg tgg tac tac cac cgc acg gtc<br>Thr Ser Leu Gly Leu Ala Ser Ala Pro Trp Tyr Tyr His Arg Thr Val<br>565 570 575 | | 1728 |

-continued

| | |
|---|---|
| acc gat tcc aag ggc aag aag tac acc gtg gcc gaa acc gct ctg ccg<br>Thr Asp Ser Lys Gly Lys Lys Tyr Thr Val Ala Glu Thr Ala Leu Pro<br>580                           585                     590 | 1776 |
| cag atg gcc gtg gcc atc gcc ggc gac gag aac gaa gac ggt gcc gtc<br>Gln Met Ala Val Ala Ile Ala Gly Asp Glu Asn Glu Asp Gly Ala Val<br>      595                      600                    605 | 1824 |
| aac tgg cag gat ggc gca atc gcc tac cgc gac atc atg aac aac ccg<br>Asn Trp Gln Asp Gly Ala Ile Ala Tyr Arg Asp Ile Met Asn Asn Pro<br>610                         615                     620 | 1872 |
| tac aag tcc gag gaa gtt ccc gaa ctg gtg gca tgg cgt atc gcc atg<br>Tyr Lys Ser Glu Glu Val Pro Glu Leu Val Ala Trp Arg Ile Ala Met<br>625                       630                    635                  640 | 1920 |
| aac ttc ggc tcc cag gcg cag aac ccg ttc ctc acc acg ctt gac aac<br>Asn Phe Gly Ser Gln Ala Gln Asn Pro Phe Leu Thr Thr Leu Asp Asn<br>                    645                    650                    655 | 1968 |
| gtc aag aag gtg gcc ttg aac acc gac ggc ctc ggc cag tcc gtg ctg<br>Val Lys Lys Val Ala Leu Asn Thr Asp Gly Leu Gly Gln Ser Val Leu<br>      660                      665                    670 | 2016 |
| ctc aag ggc tac ggc aat gaa ggc cac gac tcc ggc cac ccg gac tac<br>Leu Lys Gly Tyr Gly Asn Glu Gly His Asp Ser Gly His Pro Asp Tyr<br>675                       680                     685 | 2064 |
| ggc gat atc ggc cag cgt ctc ggc ggc gcc gac gac atg aac acc atg<br>Gly Asp Ile Gly Gln Arg Leu Gly Gly Ala Asp Asp Met Asn Thr Met<br>690                       695                    700 | 2112 |
| atg gaa gag ggc tcc aag tat ggc gct cgc ttc ggt gtg cac gtc aac<br>Met Glu Glu Gly Ser Lys Tyr Gly Ala Arg Phe Gly Val His Val Asn<br>705                       710                    715                  720 | 2160 |
| gcc tcc gaa atg tat ccg gaa gcc aag gcc ttc agc gag gac atg gtg<br>Ala Ser Glu Met Tyr Pro Glu Ala Lys Ala Phe Ser Glu Asp Met Val<br>                    725                    730                    735 | 2208 |
| cgc cgc aac tct gca ggc ggc ctg agc tac ggc tgg aac tgg ctt gat<br>Arg Arg Asn Ser Ala Gly Gly Leu Ser Tyr Gly Trp Asn Trp Leu Asp<br>          740                    745                    750 | 2256 |
| cag ggt gtc ggc atc gac ggc atc tac gat ctg gca tcc ggt tct cgt<br>Gln Gly Val Gly Ile Asp Gly Ile Tyr Asp Leu Ala Ser Gly Ser Arg<br>               755                    760                    765 | 2304 |
| gta agc cgt ttc gct gac ctc agc aag gaa gtc ggc gac aac atg gac<br>Val Ser Arg Phe Ala Asp Leu Ser Lys Glu Val Gly Asp Asn Met Asp<br>770                       775                    780 | 2352 |
| ttc atc tac ctc gat gtg tgg ggc aac ctg act tct tcc ggt tcg gaa<br>Phe Ile Tyr Leu Asp Val Trp Gly Asn Leu Thr Ser Ser Gly Ser Glu<br>785                       790                    795                  800 | 2400 |
| gat tct tgg gaa acc cgc aag atg agc aag atg atc aac gac aac ggc<br>Asp Ser Trp Glu Thr Arg Lys Met Ser Lys Met Ile Asn Asp Asn Gly<br>                    805                    810                    815 | 2448 |
| tgg cgt atg acc acc gaa tgg ggt tcc ggc aac gag tac gac tcc acc<br>Trp Arg Met Thr Thr Glu Trp Gly Ser Gly Asn Glu Tyr Asp Ser Thr<br>              820                    825                    830 | 2496 |
| ttc cag cac tgg gca gct gat ctg acc tac ggc ggc tac acc tcc aag<br>Phe Gln His Trp Ala Ala Asp Leu Thr Tyr Gly Gly Tyr Thr Ser Lys<br>835                       840                    845 | 2544 |
| ggc gag aac tcc gaa gtg atg cgc ttc ctg cgc aac cac cag aag gac<br>Gly Glu Asn Ser Glu Val Met Arg Phe Leu Arg Asn His Gln Lys Asp<br>850                       855                    860 | 2592 |
| agc tgg gtt ggc gac tac ccg caa tac ggc ggc gct gcc aac gcc ccg<br>Ser Trp Val Gly Asp Tyr Pro Gln Tyr Gly Gly Ala Ala Asn Ala Pro<br>865                       870                    875                  880 | 2640 |
| ctg ctc ggc ggc tac aac atg aag gac ttc gaa ggc tgg cag ggc cgc<br>Leu Leu Gly Gly Tyr Asn Met Lys Asp Phe Glu Gly Trp Gln Gly Arg | 2688 |

-continued

| | | | |
|---|---|---|---|
| | 885 | 890 | 895 |

| | | |
|---|---|---|
| aac gac tat gcc gcc tac atc aag aac ctg tac acc cat gat gtg tcc<br>Asn Asp Tyr Ala Ala Tyr Ile Lys Asn Leu Tyr Thr His Asp Val Ser<br>            900                    905                910 | 2736 |
| act aag ttc atc cag cac ttc aag gtg acc cgc tgg gtc aac aac ccg<br>Thr Lys Phe Ile Gln His Phe Lys Val Thr Arg Trp Val Asn Asn Pro<br>            915                    920                925 | 2784 |
| ctg ctg acc gcc gac aat ggc aat gcc gct gcc gtg tcc gac ccg aac<br>Leu Leu Thr Ala Asp Asn Gly Asn Ala Ala Ala Val Ser Asp Pro Asn<br>    930                  935                  940 | 2832 |
| acg aac aac ggc aac gag cag att acc ctg aag gat tcc aac ggc aac<br>Thr Asn Asn Gly Asn Glu Gln Ile Thr Leu Lys Asp Ser Asn Gly Asn<br>945                  950                  955                960 | 2880 |
| gtt gta gta gtc tcc cgt ggt tcc aac gac acc tct agc gca gcc tac<br>Val Val Val Val Ser Arg Gly Ser Asn Asp Thr Ser Ser Ala Ala Tyr<br>            965                    970                975 | 2928 |
| cgc cag cgc acc atc acc ttc aac ggc gtg aag gtc gca tcc ggt gtg<br>Arg Gln Arg Thr Ile Thr Phe Asn Gly Val Lys Val Ala Ser Gly Val<br>            980                    985                990 | 2976 |
| gtc tcc gca ggc gat ggc agc gcc act ggc gac gag tcc tac ctg ctg<br>Val Ser Ala Gly Asp Gly Ser Ala Thr Gly Asp Glu Ser Tyr Leu Leu<br>    995                  1000               1005 | 3024 |
| ccg tgg atg tgg gat tcc ttc acc ggc aag ctg gtc aag gat tcc<br>Pro Trp Met Trp Asp Ser Phe Thr Gly Lys Leu Val Lys Asp Ser<br>    1010               1015            1020 | 3069 |
| gag cag aag ctc tac cac tgg aac acc aag ggc ggc acc acc acc<br>Glu Gln Lys Leu Tyr His Trp Asn Thr Lys Gly Gly Thr Thr Thr<br>    1025               1030            1035 | 3114 |
| tgg acg ctg ccg gac agc tgg aag aac ctc tcc agc gta aag gtg<br>Trp Thr Leu Pro Asp Ser Trp Lys Asn Leu Ser Ser Val Lys Val<br>    1040               1045            1050 | 3159 |
| tac cag ctc acc gat cag ggc aag acc aac gag cag acc gtt gcc<br>Tyr Gln Leu Thr Asp Gln Gly Lys Thr Asn Glu Gln Thr Val Ala<br>    1055               1060            1065 | 3204 |
| gtc tcc ggc ggc aag gtg acg ctt acc gct gat gcc gaa acc ccg<br>Val Ser Gly Gly Lys Val Thr Leu Thr Ala Asp Ala Glu Thr Pro<br>    1070               1075            1080 | 3249 |
| tac gtg gtg tac aag ggc gaa gcc aag cag atc cag gtc aac tgg<br>Tyr Val Val Tyr Lys Gly Glu Ala Lys Gln Ile Gln Val Asn Trp<br>    1085               1090            1095 | 3294 |
| agc gaa ggc atg cat gtg gta gac gcc ggc ttc aac ggc ggc tcc<br>Ser Glu Gly Met His Val Val Asp Ala Gly Phe Asn Gly Gly Ser<br>    1100               1105            1110 | 3339 |
| aac acc ctc acc gac aac tgg acc gtc agc ggc tcc ggc aag gcc<br>Asn Thr Leu Thr Asp Asn Trp Thr Val Ser Gly Ser Gly Lys Ala<br>    1115               1120            1125 | 3384 |
| gaa gtt gaa ggc gac aac aac gcc atg ctg cgc ctg acc ggc aag<br>Glu Val Glu Gly Asp Asn Asn Ala Met Leu Arg Leu Thr Gly Lys<br>    1130               1135            1140 | 3429 |
| gtc gat gtc tcc cag cgt ctg acc gat ctc aag gct ggc cag aag<br>Val Asp Val Ser Gln Arg Leu Thr Asp Leu Lys Ala Gly Gln Lys<br>    1145               1150            1155 | 3474 |
| tac gcg ctg tat gtt ggc gtc gac aac cgc tcc acc ggc gat gca<br>Tyr Ala Leu Tyr Val Gly Val Asp Asn Arg Ser Thr Gly Asp Ala<br>    1160               1165            1170 | 3519 |
| tcc gtc acc gta acc agc ggc ggc aag gtg ctg gcc acc aac tcc<br>Ser Val Thr Val Thr Ser Gly Gly Lys Val Leu Ala Thr Asn Ser<br>    1175               1180            1185 | 3564 |
| acc ggc aag tcc atc gcc aag aac tac atc aag gca tac ggc cac | 3609 |

```
            Thr Gly Lys Ser Ile Ala Lys Asn Tyr Ile Lys Ala Tyr Gly His
                1190            1195            1200 aac acg aac agc aat acg gaa aat ggc tcc agc tac ttc cag aac            3654
Asn Thr Asn Ser Asn Thr Glu Asn Gly Ser Ser Tyr Phe Gln Asn
    1205            1210            1215 atg tac gtg ttc ttc acc gcg cct gag aac ggc gat gcc acg gta            3699
Met Tyr Val Phe Phe Thr Ala Pro Glu Asn Gly Asp Ala Thr Val
    1220            1225            1230 acc ctg tct cac aag agc acc gac gga gca cac acc tac ttc gac            3744
Thr Leu Ser His Lys Ser Thr Asp Gly Ala His Thr Tyr Phe Asp
    1235            1240            1245 gat gtg cgc atc gtg gag aac cag tac tcc ggc atc acc tat gag            3789
Asp Val Arg Ile Val Glu Asn Gln Tyr Ser Gly Ile Thr Tyr Glu
    1250            1255            1260 aag gac ggc acg ctg aag tcc ctc acc aac gga ttc gaa aac aac            3834
Lys Asp Gly Thr Leu Lys Ser Leu Thr Asn Gly Phe Glu Asn Asn
    1265            1270            1275 gcc cag ggc atc tgg ccg ttc gtg gtc tcc ggt tcc gaa ggc gtt            3879
Ala Gln Gly Ile Trp Pro Phe Val Val Ser Gly Ser Glu Gly Val
    1280            1285            1290 gag gac aac cgc atc cac ctc tcc gag ctg cat gct ccg ttc acg            3924
Glu Asp Asn Arg Ile His Leu Ser Glu Leu His Ala Pro Phe Thr
    1295            1300            1305 cgg gcc ggt tgg gat gtc aag aag atg gac gat gtg ctc gat ggc            3969
Arg Ala Gly Trp Asp Val Lys Lys Met Asp Asp Val Leu Asp Gly
    1310            1315            1320 act tgg tct gtg aag gtt aac ggc ctg acc cag aag ggc acg ctg            4014
Thr Trp Ser Val Lys Val Asn Gly Leu Thr Gln Lys Gly Thr Leu
    1325            1330            1335 gtc tac cag acg atc ccg cag aac gtg aag ttc gag gcg ggt gcc            4059
Val Tyr Gln Thr Ile Pro Gln Asn Val Lys Phe Glu Ala Gly Ala
    1340            1345            1350 aag tac aag gtg agc ttc gac tac cag tcc ggt tcc gat gac atc            4104
Lys Tyr Lys Val Ser Phe Asp Tyr Gln Ser Gly Ser Asp Asp Ile
    1355            1360            1365 tac gcc atc gct gtg ggc cag ggt gaa tac tct gcc ggc agc gtg            4149
Tyr Ala Ile Ala Val Gly Gln Gly Glu Tyr Ser Ala Gly Ser Val
    1370            1375            1380 aag ctg acc aac ctg aag aag gct ctg ggt gag acc ggc aag gcc            4194
Lys Leu Thr Asn Leu Lys Lys Ala Leu Gly Glu Thr Gly Lys Ala
    1385            1390            1395 gag ttc gag ctg acc ggt ggc gtc aac ggc gat tcc tgg ttc ggt            4239
Glu Phe Glu Leu Thr Gly Gly Val Asn Gly Asp Ser Trp Phe Gly
    1400            1405            1410 att tac tcg acc gca acc gca cct gat ctg cag ggt tcc acc ggc            4284
Ile Tyr Ser Thr Ala Thr Ala Pro Asp Leu Gln Gly Ser Thr Gly
    1415            1420            1425 aat gca cag gac ttc ggc gga tac aag gac ttc gtg ctc gac aac            4329
Asn Ala Gln Asp Phe Gly Gly Tyr Lys Asp Phe Val Leu Asp Asn
    1430            1435            1440 ctg aag atc gag cgc atc gag tcc cag acc cgc acc aag gcc gaa            4374
Leu Lys Ile Glu Arg Ile Glu Ser Gln Thr Arg Thr Lys Ala Glu
    1445            1450            1455 gcg cag gac aag gtc aag gaa atc cgc ggc aag tac gat tcc aag            4419
Ala Gln Asp Lys Val Lys Glu Ile Arg Gly Lys Tyr Asp Ser Lys
    1460            1465            1470 cgt gct gag ctc tcc gat gcc gca tgg cag cag tat cag gac acc            4464
Arg Ala Glu Leu Ser Asp Ala Ala Trp Gln Gln Tyr Gln Asp Thr
    1475            1480            1485
```

| | | | | | | | | | | | | |
|---|---|---|---|---|---|---|---|---|---|---|---|---|
| ttg | gtc | aag | gct | cgc | gtg | ctc | atc | aac | aag | aat | ggc | gca acc gct |
| Leu | Val | Lys | Ala | Arg | Val | Leu | Ile | Asn | Lys | Asn | Gly | Ala Thr Ala |
| | 1490 | | | | 1495 | | | | 1500 | | | |

```
ttg gtc aag gct cgc gtg ctc atc aac aag aat ggc gca acc gct     4509
Leu Val Lys Ala Arg Val Leu Ile Asn Lys Asn Gly Ala Thr Ala
    1490            1495            1500 gag gac ttc acc aag gca tac gac att ctc gtg gcc ctc gac gag     4554
Glu Asp Phe Thr Lys Ala Tyr Asp Ile Leu Val Ala Leu Asp Glu
    1505            1510            1515 tac atg aag acc gct ccc ggc aac gag agc agc gac aag tac gac     4599
Tyr Met Lys Thr Ala Pro Gly Asn Glu Ser Ser Asp Lys Tyr Asp
    1520            1525            1530 gtg gca gct gac ggc tcc gat gag ctg ggt ggc tac acc gtg gcc     4644
Val Ala Ala Asp Gly Ser Asp Glu Leu Gly Gly Tyr Thr Val Ala
    1535            1540            1545 acg ggc agc gaa gag cct acc gca ggc ctg ccg agc gaa ggc ccg     4689
Thr Gly Ser Glu Glu Pro Thr Ala Gly Leu Pro Ser Glu Gly Pro
    1550            1555            1560 gcc gat ctg gca cag gat ggc aac gac agc acc cac tgg cac acc     4734
Ala Asp Leu Ala Gln Asp Gly Asn Asp Ser Thr His Trp His Thr
    1565            1570            1575 agc tgg agc gag aac gca gtc ggc aac ggc acc gca tgg tat cag     4779
Ser Trp Ser Glu Asn Ala Val Gly Asn Gly Thr Ala Trp Tyr Gln
    1580            1585            1590 ttc aac ctc aac gaa ccg acc acc atc aac ggc ctg cgc tac ctg     4824
Phe Asn Leu Asn Glu Pro Thr Thr Ile Asn Gly Leu Arg Tyr Leu
    1595            1600            1605 ccg cgc tcc gga ggt atg aac gcc aac ggc aag atc aag ggc tac     4869
Pro Arg Ser Gly Gly Met Asn Ala Asn Gly Lys Ile Lys Gly Tyr
    1610            1615            1620 aag atc acg ctc act ctg gcg gat ggc acc acc aag gat gtc gtc     4914
Lys Ile Thr Leu Thr Leu Ala Asp Gly Thr Thr Lys Asp Val Val
    1625            1630            1635 acc gat gct gag ttc tcc acc acc acc atg tgg cag aag gcc agc     4959
Thr Asp Ala Glu Phe Ser Thr Thr Thr Met Trp Gln Lys Ala Ser
    1640            1645            1650 ttc gac gcc gtc gag aat gtg acc gcc gta cgc tcg acc gtc ctg     5004
Phe Asp Ala Val Glu Asn Val Thr Ala Val Arg Ser Thr Val Leu
    1655            1660            1665 tct tcc gca ggc cag agc gac tcc cag gcc aac aag ttc gca tcc     5049
Ser Ser Ala Gly Gln Ser Asp Ser Gln Ala Asn Lys Phe Ala Ser
    1670            1675            1680 gct gcc gaa ctg cgt ttg acc acg gac cgc gag gtt gag gaa gag     5094
Ala Ala Glu Leu Arg Leu Thr Thr Asp Arg Glu Val Glu Glu Glu
    1685            1690            1695 act gtc gct ccg gac aag acc gac ctc aac gac acc atc gcc aag     5139
Thr Val Ala Pro Asp Lys Thr Asp Leu Asn Asp Thr Ile Ala Lys
    1700            1705            1710 gct aac ggt ctt aag gaa tcc gac tac acg gct gaa agc tgg act     5184
Ala Asn Gly Leu Lys Glu Ser Asp Tyr Thr Ala Glu Ser Trp Thr
    1715            1720            1725 gct ctg gtc aag gcc cgc gaa gct gca cag gcc gtg gcg gat aac     5229
Ala Leu Val Lys Ala Arg Glu Ala Ala Gln Ala Val Ala Asp Asn
    1730            1735            1740 gat aag gcc acc gct tac gat gtg gct ctg gcg ctg acg aac ctc     5274
Asp Lys Ala Thr Ala Tyr Asp Val Ala Leu Ala Leu Thr Asn Leu
    1745            1750            1755 gaa tcc gct atc gct ggt ctc gag aag acc ggt gag gag cct ggc     5319
Glu Ser Ala Ile Ala Gly Leu Glu Lys Thr Gly Glu Glu Pro Gly
    1760            1765            1770 cca ggc ccg gtt gag gtg aac aag acc gac ctg cag act gca gtg     5364
Pro Gly Pro Val Glu Val Asn Lys Thr Asp Leu Gln Thr Ala Val
    1775            1780            1785
```

```
aac aag gca agc aag ctc gag aag gcc gat tac acg acc aac tcg      5409
Asn Lys Ala Ser Lys Leu Glu Lys Ala Asp Tyr Thr Thr Asn Ser
    1790            1795                1800 tgg gaa gct ttc gcc gag gca ctg aag gct gca cag cag gtg ctc      5454
Trp Glu Ala Phe Ala Glu Ala Leu Lys Ala Ala Gln Gln Val Leu
1805            1810                1815 gac aac aag aac gcc acc cag cag gat gtg gat acc gca ctg agc      5499
Asp Asn Lys Asn Ala Thr Gln Gln Asp Val Asp Thr Ala Leu Ser
    1820            1825                1830 gct ctt cag gac gcc atc tcc aag ctg gaa gct gcc acc gag ccg      5544
Ala Leu Gln Asp Ala Ile Ser Lys Leu Glu Ala Ala Thr Glu Pro
1835            1840                1845 aag ccg aat ccg gaa ccg ggc gtg gtg gac aag gct gct ctg aac      5589
Lys Pro Asn Pro Glu Pro Gly Val Val Asp Lys Ala Ala Leu Asn
    1850            1855                1860 gcg acc atc aac aag gcc gcc gcc atc aac ctg ggt ctc tac acc      5634
Ala Thr Ile Asn Lys Ala Ala Ala Ile Asn Leu Gly Leu Tyr Thr
1865            1870                1875 gac gac tcc gcc aac gct ctg cgc gcc gcg ctg aag aag gcc cgt      5679
Asp Asp Ser Ala Asn Ala Leu Arg Ala Ala Leu Lys Lys Ala Arg
    1880            1885                1890 gag gtc tcc gac aac agc aac gcc acg cag aag cag gtc gac gca      5724
Glu Val Ser Asp Asn Ser Asn Ala Thr Gln Lys Gln Val Asp Ala
1895            1900                1905 gct cgt gaa gcc ctg gag aag gca att gcc gct ctg gtg aag cgt      5769
Ala Arg Glu Ala Leu Glu Lys Ala Ile Ala Ala Leu Val Lys Arg
    1910            1915                1920 ccc gct gcc aag ggt gat ggc aac gtt gtt tcc aac acg ggc tcc      5814
Pro Ala Ala Lys Gly Asp Gly Asn Val Val Ser Asn Thr Gly Ser
1925            1930                1935 gat gtc gcc acg atc gct ctg gct gga ctg ctg ctg gca ggt gct      5859
Asp Val Ala Thr Ile Ala Leu Ala Gly Leu Leu Leu Ala Gly Ala
    1940            1945                1950 ggc gcc gcc atc gcc tac cgt cgc aat cgc gag caa ctg tga          5901
Gly Ala Ala Ile Ala Tyr Arg Arg Asn Arg Glu Gln Leu
1955            1960                1965

<210> SEQ ID NO 2
<211> LENGTH: 1966
<212> TYPE: PRT
<213> ORGANISM: Bifidobacterium lomgum JCM1217

<400> SEQUENCE: 2

Met Lys Lys Lys Lys Thr Ile Ser Ala Ala Leu Ala Thr Ala Leu Ala
1               5                   10                  15

Leu Thr Cys Met Gly Ser Gly Gly Gly Thr Ala Phe Ala Val Pro Leu
            20                  25                  30

Ser Asp Ala Asp Leu Gln Thr Leu Ala Ser Gln Ile Gln Gln Ile Asn
        35                  40                  45

Asp Thr Ser Asp Ser Ala Thr Ala Ser Glu Thr Pro Ser Ala Gln Ala
    50                  55                  60

Asp Ala Val Glu Gly Trp Thr Ile Asp Ser Asn Ile Ala Gln Gly Gly
65                  70                  75                  80

Glu Ile Leu Glu Met Ala Asn Gly Trp Leu His Leu Lys Ser Thr Ala
                85                  90                  95

Ser Asn Gly Asn Ala Ala Ala Asn Pro Ser Ser Ser Asn Asn Trp Pro
            100                 105                 110

Ala Val Ala Val Trp Gly Thr Asp Tyr Asp Phe Ser Lys Ala Gly Ser
```

```
                  115                 120                 125
Phe His Ala Thr Ile Lys Ser Pro Gln Glu Gly Ser Ala Asn Arg Phe
        130                 135                 140

Gly Phe Tyr Leu Gly Tyr Asn Asp Pro Gly Ser Gly Leu Phe Ile Gly
145                 150                 155                 160

Tyr Asp Ser Gly Gly Trp Phe Trp Gln Thr Tyr Thr Gly Gly Gly Ser
                165                 170                 175

Gly Ser Trp Tyr Ser Gly Ala Arg Ile Ala Ala Pro Ser Ala Asn Glu
            180                 185                 190

Glu His Asp Ile Arg Val Ser Trp Thr Asp Ala Lys Val Ala Thr Leu
        195                 200                 205

Thr Val Asp Gly Gln Lys Ala Phe Asp Val Asp Tyr Ser Ala Met Thr
    210                 215                 220

Asn Leu Ser Asn Lys Leu Ala Ile Lys Ala Gly Ser Trp Lys Glu Leu
225                 230                 235                 240

Asn Glu Val Thr Asp Val Tyr Ile Lys Asp Phe Pro Glu Val Val Glu
                245                 250                 255

Ala Ala Lys His Ala Val Ser Gly Lys Val Val Asp Ala Gly Gly Ala
            260                 265                 270

Ala Ile Glu Gly Ala Thr Val Arg Leu Asp Lys Thr Lys Val Lys Thr
        275                 280                 285

Gly Ala Asp Gly Thr Phe Ser Phe Ala Asp Ile Glu Glu Gly Glu His
    290                 295                 300

Thr Leu Ser Ile Ala Lys Glu Gly Tyr Glu Asp Val Ser Gln Gln Val
305                 310                 315                 320

Thr Val Ser Gly Ala Asp Leu Ala Ile Asp Pro Ile Thr Leu Asn Lys
                325                 330                 335

Thr Val Gln Val Ala Ser Glu Thr Leu Lys Thr Lys Met Glu Val
            340                 345                 350

Gln Ile Lys Lys Asn Phe Pro Ser Val Leu Gln Tyr Thr Met Thr Asp
        355                 360                 365

Gly Lys Val Met Tyr Gly Gln Ser Lys Asp Val Arg Thr Val Glu Ile
    370                 375                 380

Asn Gly Thr Asn Ile Glu Leu Gly Asp Asp Val Thr Phe Lys Lys
385                 390                 395                 400

Val Ser Asp Thr Glu Ala Thr Tyr Thr Leu Lys Val Lys Asp Glu Ala
                405                 410                 415

Lys Lys Ile Asp Ala Val Ile Thr Val Gln Ile Thr Val Lys Ala Asn
            420                 425                 430

Gln Leu His Leu Asn Val Thr Lys Ile Lys Asn Asn Leu Ser Glu Gly
        435                 440                 445

Ile Pro Glu Gly Asn Gly Val Glu Glu Asn Ala Ile Gln Thr Leu Ser
    450                 455                 460

Phe Pro Asn Gln Ser Leu Val Ser Val Arg Ser Ser Gln Glu Asn Ala
465                 470                 475                 480

Gln Phe Thr Gly Ala Arg Met Ser Ser Asn Thr Gln Lys Pro Gly Asp
                485                 490                 495

Thr Asn Phe Ala Val Thr Glu Asp Thr Asn Val Thr Asp Ser Asp Tyr
            500                 505                 510

Thr Tyr Gly Phe Ile Ser Gly Ala Gly Leu Ser Ala Gly Leu Trp Ser
        515                 520                 525

Asn Ser Glu His Asp Gly Thr Tyr Val Ala Ala Pro Val Arg Gly Gly
    530                 535                 540
```

```
Ser Gln Asn Thr Arg Val Tyr Ala Thr Thr Gln Gln Thr Gly Asp Ala
545                 550                 555                 560

Thr Ser Leu Gly Leu Ala Ser Ala Pro Trp Tyr Tyr His Arg Thr Val
                565                 570                 575

Thr Asp Ser Lys Gly Lys Lys Tyr Thr Val Ala Glu Thr Ala Leu Pro
            580                 585                 590

Gln Met Ala Val Ala Ile Ala Gly Asp Glu Asn Glu Asp Gly Ala Val
            595                 600                 605

Asn Trp Gln Asp Gly Ala Ile Ala Tyr Arg Asp Ile Met Asn Asn Pro
610                 615                 620

Tyr Lys Ser Glu Glu Val Pro Glu Leu Val Ala Trp Arg Ile Ala Met
625                 630                 635                 640

Asn Phe Gly Ser Gln Ala Gln Asn Pro Phe Leu Thr Thr Leu Asp Asn
                645                 650                 655

Val Lys Lys Val Ala Leu Asn Thr Asp Gly Leu Gly Gln Ser Val Leu
                660                 665                 670

Leu Lys Gly Tyr Gly Asn Glu Gly His Asp Ser Gly His Pro Asp Tyr
            675                 680                 685

Gly Asp Ile Gly Gln Arg Leu Gly Ala Asp Asp Met Asn Thr Met
690                 695                 700

Met Glu Glu Gly Ser Lys Tyr Gly Ala Arg Phe Gly Val His Val Asn
705                 710                 715                 720

Ala Ser Glu Met Tyr Pro Glu Ala Lys Ala Phe Ser Glu Asp Met Val
                725                 730                 735

Arg Arg Asn Ser Ala Gly Gly Leu Ser Tyr Gly Trp Asn Trp Leu Asp
                740                 745                 750

Gln Gly Val Gly Ile Asp Gly Ile Tyr Asp Leu Ala Ser Gly Ser Arg
            755                 760                 765

Val Ser Arg Phe Ala Asp Leu Ser Lys Glu Val Gly Asp Asn Met Asp
770                 775                 780

Phe Ile Tyr Leu Asp Val Trp Gly Asn Leu Thr Ser Ser Gly Ser Glu
785                 790                 795                 800

Asp Ser Trp Glu Thr Arg Lys Met Ser Lys Met Ile Asn Asp Asn Gly
                805                 810                 815

Trp Arg Met Thr Thr Glu Trp Gly Ser Gly Asn Glu Tyr Asp Ser Thr
                820                 825                 830

Phe Gln His Trp Ala Ala Asp Leu Thr Tyr Gly Gly Tyr Thr Ser Lys
            835                 840                 845

Gly Glu Asn Ser Glu Val Met Arg Phe Leu Arg Asn His Gln Lys Asp
850                 855                 860

Ser Trp Val Gly Asp Tyr Pro Gln Tyr Gly Gly Ala Ala Asn Ala Pro
865                 870                 875                 880

Leu Leu Gly Gly Tyr Asn Met Lys Asp Phe Glu Gly Trp Gln Gly Arg
                885                 890                 895

Asn Asp Tyr Ala Ala Tyr Ile Lys Asn Leu Tyr Thr His Asp Val Ser
                900                 905                 910

Thr Lys Phe Ile Gln His Phe Lys Val Thr Arg Trp Val Asn Asn Pro
            915                 920                 925

Leu Leu Thr Ala Asp Asn Gly Asn Ala Ala Ala Val Ser Asp Pro Asn
            930                 935                 940

Thr Asn Asn Gly Asn Glu Gln Ile Thr Leu Lys Asp Ser Asn Gly Asn
945                 950                 955                 960
```

-continued

Val Val Val Val Ser Arg Gly Ser Asn Asp Thr Ser Ala Ala Tyr
            965                 970                 975

Arg Gln Arg Thr Ile Thr Phe Asn Gly Val Lys Val Ala Ser Gly Val
            980                 985                 990

Val Ser Ala Gly Asp Gly Ser Ala Thr Gly Asp Glu Ser Tyr Leu Leu
            995                 1000                1005

Pro Trp Met Trp Asp Ser Phe Thr Gly Lys Leu Val Lys Asp Ser
    1010                1015                1020

Glu Gln Lys Leu Tyr His Trp Asn Thr Lys Gly Thr Thr Thr
    1025                1030                1035

Trp Thr Leu Pro Asp Ser Trp Lys Asn Leu Ser Ser Val Lys Val
    1040                1045                1050

Tyr Gln Leu Thr Asp Gln Gly Lys Thr Asn Glu Gln Thr Val Ala
    1055                1060                1065

Val Ser Gly Gly Lys Val Thr Leu Thr Ala Asp Ala Glu Thr Pro
    1070                1075                1080

Tyr Val Val Tyr Lys Gly Glu Ala Lys Gln Ile Gln Val Asn Trp
    1085                1090                1095

Ser Glu Gly Met His Val Val Asp Ala Gly Phe Asn Gly Gly Ser
    1100                1105                1110

Asn Thr Leu Thr Asp Asn Trp Thr Val Ser Gly Ser Gly Lys Ala
    1115                1120                1125

Glu Val Glu Gly Asp Asn Asn Ala Met Leu Arg Leu Thr Gly Lys
    1130                1135                1140

Val Asp Val Ser Gln Arg Leu Thr Asp Leu Lys Ala Gly Gln Lys
    1145                1150                1155

Tyr Ala Leu Tyr Val Gly Val Asp Asn Arg Ser Thr Gly Asp Ala
    1160                1165                1170

Ser Val Thr Val Thr Ser Gly Gly Lys Val Leu Ala Thr Asn Ser
    1175                1180                1185

Thr Gly Lys Ser Ile Ala Lys Asn Tyr Ile Lys Ala Tyr Gly His
    1190                1195                1200

Asn Thr Asn Ser Asn Thr Glu Asn Gly Ser Ser Tyr Phe Gln Asn
    1205                1210                1215

Met Tyr Val Phe Phe Thr Ala Pro Glu Asn Gly Asp Ala Thr Val
    1220                1225                1230

Thr Leu Ser His Lys Ser Thr Asp Gly Ala His Thr Tyr Phe Asp
    1235                1240                1245

Asp Val Arg Ile Val Glu Asn Gln Tyr Ser Gly Ile Thr Tyr Glu
    1250                1255                1260

Lys Asp Gly Thr Leu Lys Ser Leu Thr Asn Gly Phe Glu Asn Asn
    1265                1270                1275

Ala Gln Gly Ile Trp Pro Val Val Ser Gly Ser Glu Gly Val
    1280                1285                1290

Glu Asp Asn Arg Ile His Leu Ser Glu Leu His Ala Pro Phe Thr
    1295                1300                1305

Arg Ala Gly Trp Asp Val Lys Lys Met Asp Asp Val Leu Asp Gly
    1310                1315                1320

Thr Trp Ser Val Lys Val Asn Gly Leu Thr Gln Lys Gly Thr Leu
    1325                1330                1335

Val Tyr Gln Thr Ile Pro Gln Asn Val Lys Phe Glu Ala Gly Ala
    1340                1345                1350

Lys Tyr Lys Val Ser Phe Asp Tyr Gln Ser Gly Ser Asp Asp Ile

-continued

```
              1355                1360                1365
Tyr Ala  Ile Ala Val Gly Gln  Gly Glu Tyr Ser Ala  Gly Ser Val
    1370                1375                1380

Lys Leu  Thr Asn Leu Lys Lys  Ala Leu Gly Glu Thr  Gly Lys Ala
    1385                1390                1395

Glu Phe  Glu Leu Thr Gly Gly  Val Asn Gly Asp Ser  Trp Phe Gly
    1400                1405                1410

Ile Tyr  Ser Thr Ala Thr Ala  Pro Asp Leu Gln Gly  Ser Thr Gly
    1415                1420                1425

Asn Ala  Gln Asp Phe Gly Gly  Tyr Lys Asp Phe Val  Leu Asp Asn
    1430                1435                1440

Leu Lys  Ile Glu Arg Ile Glu  Ser Gln Thr Arg Thr  Lys Ala Glu
    1445                1450                1455

Ala Gln  Asp Lys Val Lys Glu  Ile Arg Gly Lys Tyr  Asp Ser Lys
    1460                1465                1470

Arg Ala  Glu Leu Ser Asp Ala  Ala Trp Gln Gln Tyr  Gln Asp Thr
    1475                1480                1485

Leu Val  Lys Ala Arg Val Leu  Ile Asn Lys Asn Gly  Ala Thr Ala
    1490                1495                1500

Glu Asp  Phe Thr Lys Ala Tyr  Asp Ile Leu Val Ala  Leu Asp Glu
    1505                1510                1515

Tyr Met  Lys Thr Ala Pro Gly  Asn Glu Ser Ser Asp  Lys Tyr Asp
    1520                1525                1530

Val Ala  Ala Asp Gly Ser Asp  Glu Leu Gly Gly Tyr  Thr Val Ala
    1535                1540                1545

Thr Gly  Ser Glu Glu Pro Thr  Ala Gly Leu Pro Ser  Glu Gly Pro
    1550                1555                1560

Ala Asp  Leu Ala Gln Asp Gly  Asn Asp Ser Thr His  Trp His Thr
    1565                1570                1575

Ser Trp  Ser Glu Asn Ala Val  Gly Asn Gly Thr Ala  Trp Tyr Gln
    1580                1585                1590

Phe Asn  Leu Asn Glu Pro Thr  Thr Ile Asn Gly Leu  Arg Tyr Leu
    1595                1600                1605

Pro Arg  Ser Gly Gly Met Asn  Ala Asn Gly Lys Ile  Lys Gly Tyr
    1610                1615                1620

Lys Ile  Thr Leu Thr Leu Ala  Asp Gly Thr Thr Lys  Asp Val Val
    1625                1630                1635

Thr Asp  Ala Glu Phe Ser Thr  Thr Thr Met Trp Gln  Lys Ala Ser
    1640                1645                1650

Phe Asp  Ala Val Glu Asn Val  Thr Ala Val Arg Ser  Thr Val Leu
    1655                1660                1665

Ser Ser  Ala Gly Gln Ser Asp  Ser Gln Ala Asn Lys  Phe Ala Ser
    1670                1675                1680

Ala Ala  Glu Leu Arg Leu Thr  Thr Asp Arg Glu Val  Glu Glu Glu
    1685                1690                1695

Thr Val  Ala Pro Asp Lys Thr  Asp Leu Asn Asp Thr  Ile Ala Lys
    1700                1705                1710

Ala Asn  Gly Leu Lys Glu Ser  Asp Tyr Thr Ala Glu  Ser Trp Thr
    1715                1720                1725

Ala Leu  Val Lys Ala Arg Glu  Ala Ala Gln Ala Val  Ala Asp Asn
    1730                1735                1740

Asp Lys  Ala Thr Ala Tyr Asp  Val Ala Leu Ala Leu  Thr Asn Leu
    1745                1750                1755
```

```
Glu Ser Ala Ile Ala Gly Leu Glu Lys Thr Gly Glu Glu Pro Gly
    1760                1765                1770

Pro Gly Pro Val Glu Val Asn Lys Thr Asp Leu Gln Thr Ala Val
    1775                1780                1785

Asn Lys Ala Ser Lys Leu Glu Lys Ala Asp Tyr Thr Thr Asn Ser
    1790                1795                1800

Trp Glu Ala Phe Ala Glu Ala Leu Lys Ala Ala Gln Gln Val Leu
    1805                1810                1815

Asp Asn Lys Asn Ala Thr Gln Gln Asp Val Asp Thr Ala Leu Ser
    1820                1825                1830

Ala Leu Gln Asp Ala Ile Ser Lys Leu Glu Ala Ala Thr Glu Pro
    1835                1840                1845

Lys Pro Asn Pro Glu Pro Gly Val Val Asp Lys Ala Ala Leu Asn
    1850                1855                1860

Ala Thr Ile Asn Lys Ala Ala Ala Ile Asn Leu Gly Leu Tyr Thr
    1865                1870                1875

Asp Asp Ser Ala Asn Ala Leu Arg Ala Ala Leu Lys Lys Ala Arg
    1880                1885                1890

Glu Val Ser Asp Asn Ser Asn Ala Thr Gln Lys Gln Val Asp Ala
    1895                1900                1905

Ala Arg Glu Ala Leu Glu Lys Ala Ile Ala Ala Leu Val Lys Arg
    1910                1915                1920

Pro Ala Ala Lys Gly Asp Gly Asn Val Val Ser Asn Thr Gly Ser
    1925                1930                1935

Asp Val Ala Thr Ile Ala Leu Ala Gly Leu Leu Leu Ala Gly Ala
    1940                1945                1950

Gly Ala Ala Ile Ala Tyr Arg Arg Asn Arg Glu Gln Leu
    1955                1960                1965

<210> SEQ ID NO 3
<211> LENGTH: 5304
<212> TYPE: DNA
<213> ORGANISM: Streptococcus pneumoniae R6
<220> FEATURE:
<221> NAME/KEY: CDS
<222> LOCATION: (1)..(5304)

<400> SEQUENCE: 3 atg aat aaa gga tta ttt gaa aaa cgt tgt aaa tat agt att cgg aaa      48
Met Asn Lys Gly Leu Phe Glu Lys Arg Cys Lys Tyr Ser Ile Arg Lys
1               5                   10                  15 ttt tca tta ggt gtt gct tct gtt atg att gga gct aca ttc ttt ggg      96
Phe Ser Leu Gly Val Ala Ser Val Met Ile Gly Ala Thr Phe Phe Gly
            20                  25                  30 aca agt ccg gtt ctt gca gat agc gtg cag tct ggt tcc acg gcg aac     144
Thr Ser Pro Val Leu Ala Asp Ser Val Gln Ser Gly Ser Thr Ala Asn
        35                  40                  45 tta cca gct gat tta gct act gct ctt gca aca gca aaa gag aat gat     192
Leu Pro Ala Asp Leu Ala Thr Ala Leu Ala Thr Ala Lys Glu Asn Asp
    50                  55                  60 ggg cat gat ttt gaa gcg cct aag gtg gga gaa gac caa ggt tct cca     240
Gly His Asp Phe Glu Ala Pro Lys Val Gly Glu Asp Gln Gly Ser Pro
65                  70                  75                  80 gaa gtt aca gat gga cct aag aca gaa gaa gaa cta tta gca ctt gaa     288
Glu Val Thr Asp Gly Pro Lys Thr Glu Glu Glu Leu Leu Ala Leu Glu
                85                  90                  95 aaa gaa aaa ccg gct gaa gaa aaa cca aaa gag gat aaa cct gca gct     336
```

```
Lys Glu Lys Pro Ala Glu Glu Lys Pro Lys Glu Asp Lys Pro Ala Ala
            100                 105                 110 gct aaa cct gaa aca cct aag acg gta acc cct gaa tgg caa acg gta        384
Ala Lys Pro Glu Thr Pro Lys Thr Val Thr Pro Glu Trp Gln Thr Val
            115                 120                 125 gag aaa aaa gaa caa cag gga aca gtc act atc cga gaa gaa aaa ggt        432
Glu Lys Lys Glu Gln Gln Gly Thr Val Thr Ile Arg Glu Glu Lys Gly
        130                 135                 140 gtc cgc tac aac caa tta tcc tca act gct caa aat gat aac gca ggt        480
Val Arg Tyr Asn Gln Leu Ser Ser Thr Ala Gln Asn Asp Asn Ala Gly
145                 150                 155                 160 aaa cca gcc ctg ttt gaa aag aag ggc ttg acc gtt gat gcc aat gga        528
Lys Pro Ala Leu Phe Glu Lys Lys Gly Leu Thr Val Asp Ala Asn Gly
                165                 170                 175 aat gca act gtt gat tta acc ttc aaa gat gat tct gaa aag ggc aaa        576
Asn Ala Thr Val Asp Leu Thr Phe Lys Asp Asp Ser Glu Lys Gly Lys
            180                 185                 190 tca cgc ttt ggt gtc ttc ttg aaa ttt aaa gat acc aag aat aat gtt        624
Ser Arg Phe Gly Val Phe Leu Lys Phe Lys Asp Thr Lys Asn Asn Val
        195                 200                 205 ttt gtc ggt tac gac aag gat ggc tgg ttc tgg gag tat aaa tct cca        672
Phe Val Gly Tyr Asp Lys Asp Gly Trp Phe Trp Glu Tyr Lys Ser Pro
    210                 215                 220 aca act agc act tgg tat aga ggt agt cgt gtt gct gct cct gaa aca        720
Thr Thr Ser Thr Trp Tyr Arg Gly Ser Arg Val Ala Ala Pro Glu Thr
225                 230                 235                 240 gga tca aca aac cgt ctc tct atc act ctc aag tca gac ggt cag cta        768
Gly Ser Thr Asn Arg Leu Ser Ile Thr Leu Lys Ser Asp Gly Gln Leu
                245                 250                 255 aat gcc agc aat aac gat gtc aat ctc ttt gac aca gtg act cta cca        816
Asn Ala Ser Asn Asn Asp Val Asn Leu Phe Asp Thr Val Thr Leu Pro
            260                 265                 270 gct gcg gtc aat gac cat ctt aaa aat gag aag aag att ctt ctc aag        864
Ala Ala Val Asn Asp His Leu Lys Asn Glu Lys Lys Ile Leu Leu Lys
        275                 280                 285 gcg ggc tct tat gac gat gag cga aca gtt gtt agc gtt aaa acg gat        912
Ala Gly Ser Tyr Asp Asp Glu Arg Thr Val Val Ser Val Lys Thr Asp
    290                 295                 300 aac caa gag ggg gta aaa aca gag gat acc cct gct gaa aaa gaa aca        960
Asn Gln Glu Gly Val Lys Thr Glu Asp Thr Pro Ala Glu Lys Glu Thr
305                 310                 315                 320 ggt cct gaa gtt gat gat agc aag gtg act tat gac acg att cag tct       1008
Gly Pro Glu Val Asp Asp Ser Lys Val Thr Tyr Asp Thr Ile Gln Ser
                325                 330                 335 aag gtt ctc aaa gca gtg att gac caa gcc ttc cct cgt gtc aag gaa       1056
Lys Val Leu Lys Ala Val Ile Asp Gln Ala Phe Pro Arg Val Lys Glu
            340                 345                 350 tac agc ttg aat gga cat act ttg cca gga cag gtt caa cag ttc aac       1104
Tyr Ser Leu Asn Gly His Thr Leu Pro Gly Gln Val Gln Gln Phe Asn
        355                 360                 365 caa gtc ttt atc aat aac cac cga atc acc cct gaa gtc act tat aag       1152
Gln Val Phe Ile Asn Asn His Arg Ile Thr Pro Glu Val Thr Tyr Lys
    370                 375                 380 aaa atc aat gag aca aca gca gag tac ttg atg aag ctt cgc gat gat       1200
Lys Ile Asn Glu Thr Thr Ala Glu Tyr Leu Met Lys Leu Arg Asp Asp
385                 390                 395                 400 gct cac tta atc aat gcg gaa atg aca gta cgc ttg caa gtt gtg gac       1248
Ala His Leu Ile Asn Ala Glu Met Thr Val Arg Leu Gln Val Val Asp
                405                 410                 415
```

```
aat caa ttg cac ttt gat gtg acc aag att gtc aac cac aat caa gtc    1296
Asn Gln Leu His Phe Asp Val Thr Lys Ile Val Asn His Asn Gln Val
            420                 425                 430 act cca ggt caa aag att gat gac gaa aga aaa cta ctt tct tct att    1344
Thr Pro Gly Gln Lys Ile Asp Asp Glu Arg Lys Leu Leu Ser Ser Ile
        435                 440                 445 agt ttc ctc ggc aat gct tta gtc tct gtt tct agt gat caa act ggt    1392
Ser Phe Leu Gly Asn Ala Leu Val Ser Val Ser Ser Asp Gln Thr Gly
    450                 455                 460 gct aag ttt gat ggg gca acc atg tca aac aat acg cat gtc agc gga    1440
Ala Lys Phe Asp Gly Ala Thr Met Ser Asn Asn Thr His Val Ser Gly
465                 470                 475                 480 gat gat cat atc gat gta acc aat cca atg aaa gat cta gcc aag ggt    1488
Asp Asp His Ile Asp Val Thr Asn Pro Met Lys Asp Leu Ala Lys Gly
                485                 490                 495 tac atg tat gga ttt gtt tct aca gat aag ctt gct gct ggt gtt tgg    1536
Tyr Met Tyr Gly Phe Val Ser Thr Asp Lys Leu Ala Ala Gly Val Trp
            500                 505                 510 agt aac tct caa aac agc tat ggt ggt ggt tcg aat gac tgg act cgt    1584
Ser Asn Ser Gln Asn Ser Tyr Gly Gly Gly Ser Asn Asp Trp Thr Arg
        515                 520                 525 ttg aca gcc tat aaa gaa aca gtc gga aat gcc aac tat gta gga atc    1632
Leu Thr Ala Tyr Lys Glu Thr Val Gly Asn Ala Asn Tyr Val Gly Ile
    530                 535                 540 cac agc tct gaa tgg caa tgg gaa aaa gct tat aag ggc att gtt ttc    1680
His Ser Ser Glu Trp Gln Trp Glu Lys Ala Tyr Lys Gly Ile Val Phe
545                 550                 555                 560 cca gaa tac acg aag gaa ctt cca agt gct aag gtt gtt atc act gaa    1728
Pro Glu Tyr Thr Lys Glu Leu Pro Ser Ala Lys Val Val Ile Thr Glu
                565                 570                 575 gat gcc aat gca gac aag aaa gtc gat tgg cag gat ggt gcc att gct    1776
Asp Ala Asn Ala Asp Lys Lys Val Asp Trp Gln Asp Gly Ala Ile Ala
            580                 585                 590 tat cgt agc att atg aac aat cct caa ggt tgg aaa aaa gtt aag gat    1824
Tyr Arg Ser Ile Met Asn Asn Pro Gln Gly Trp Lys Lys Val Lys Asp
        595                 600                 605 atc aca gct tac cgt atc gcg atg aac ttt ggt tct caa gca caa aac    1872
Ile Thr Ala Tyr Arg Ile Ala Met Asn Phe Gly Ser Gln Ala Gln Asn
    610                 615                 620 cca ttc ctt atg acc ttg gat ggt atc aag aaa atc aat ctc cac aca    1920
Pro Phe Leu Met Thr Leu Asp Gly Ile Lys Lys Ile Asn Leu His Thr
625                 630                 635                 640 gat ggt ctt ggg caa ggt gtt ctc ctt aaa gga tat ggt agc gaa ggc    1968
Asp Gly Leu Gly Gln Gly Val Leu Leu Lys Gly Tyr Gly Ser Glu Gly
                645                 650                 655 cat gac tct ggt cac ttg aac tat gct gat att ggt aag cgt atc ggt    2016
His Asp Ser Gly His Leu Asn Tyr Ala Asp Ile Gly Lys Arg Ile Gly
            660                 665                 670 ggt gtc gaa gac ttc aag acc cta att gag aag gct aag aaa tat gga    2064
Gly Val Glu Asp Phe Lys Thr Leu Ile Glu Lys Ala Lys Lys Tyr Gly
        675                 680                 685 gct cat cta ggt atc cac gtt aac gct tca gaa act tat cct gag tct    2112
Ala His Leu Gly Ile His Val Asn Ala Ser Glu Thr Tyr Pro Glu Ser
    690                 695                 700 aaa tac ttc aat gaa aaa att ctc cgt aag aat cca gat gga agc tat    2160
Lys Tyr Phe Asn Glu Lys Ile Leu Arg Lys Asn Pro Asp Gly Ser Tyr
705                 710                 715                 720 agc tat ggt tgg aac tgg cta gat caa ggt atc aac att gat gct gcc    2208
Ser Tyr Gly Trp Asn Trp Leu Asp Gln Gly Ile Asn Ile Asp Ala Ala
                725                 730                 735
```

```
tat gac cta gct cat ggt cgt ttg gca cgt tgg gaa gat ttg aag aaa      2256
Tyr Asp Leu Ala His Gly Arg Leu Ala Arg Trp Glu Asp Leu Lys Lys
            740                 745                 750 aaa ctt ggt gac ggt ctc gac ttt atc tat gtg gac gtt tgg ggt aat      2304
Lys Leu Gly Asp Gly Leu Asp Phe Ile Tyr Val Asp Val Trp Gly Asn
                755                 760                 765 ggt caa tca ggt gat aac ggt gcc tgg gct acc cac gtt ctt gct aaa      2352
Gly Gln Ser Gly Asp Asn Gly Ala Trp Ala Thr His Val Leu Ala Lys
            770                 775                 780 gaa att aac aaa caa ggc tgg cgc ttt gcg atc gag tgg ggc cat ggt      2400
Glu Ile Asn Lys Gln Gly Trp Arg Phe Ala Ile Glu Trp Gly His Gly
785                 790                 795                 800 ggt gag tac gac tct acc ttc cat cac tgg gca gct gac ttg acc tac      2448
Gly Glu Tyr Asp Ser Thr Phe His His Trp Ala Ala Asp Leu Thr Tyr
                805                 810                 815 ggt ggc tac acc aat aaa ggt atc aac agt gcc atc acc cgc ttt ata      2496
Gly Gly Tyr Thr Asn Lys Gly Ile Asn Ser Ala Ile Thr Arg Phe Ile
            820                 825                 830 cgt aac cac caa aaa gat gct tgg gta ggg gac tac aga agt tat ggt      2544
Arg Asn His Gln Lys Asp Ala Trp Val Gly Asp Tyr Arg Ser Tyr Gly
        835                 840                 845 ggt gca gcc aac tat cca ctg cta ggt ggc tac agc atg aaa gac ttt      2592
Gly Ala Ala Asn Tyr Pro Leu Leu Gly Gly Tyr Ser Met Lys Asp Phe
850                 855                 860 gaa ggc tgg caa gga aga agt gac tac aat ggc tat gta act aac tta      2640
Glu Gly Trp Gln Gly Arg Ser Asp Tyr Asn Gly Tyr Val Thr Asn Leu
865                 870                 875                 880 ttt gcc cat gac gtc atg acc aag tac ttc caa cac ttc act gta agt      2688
Phe Ala His Asp Val Met Thr Lys Tyr Phe Gln His Phe Thr Val Ser
                885                 890                 895 aaa tgg gaa aat ggt aca ccg gtg act atg acc gat aac ggt agc acc      2736
Lys Trp Glu Asn Gly Thr Pro Val Thr Met Thr Asp Asn Gly Ser Thr
            900                 905                 910 tat aaa tgg act cca gaa atg cga gtg gaa ttg gta gat gct gac aat      2784
Tyr Lys Trp Thr Pro Glu Met Arg Val Glu Leu Val Asp Ala Asp Asn
        915                 920                 925 aat aaa gta gtt gta act cgt aag tca aat gat gtc aat agt cca caa      2832
Asn Lys Val Val Val Thr Arg Lys Ser Asn Asp Val Asn Ser Pro Gln
930                 935                 940 tat cgc gaa cgt aca gta act ctc aac gga cgt gtc atc caa gat ggt      2880
Tyr Arg Glu Arg Thr Val Thr Leu Asn Gly Arg Val Ile Gln Asp Gly
945                 950                 955                 960 tca gct tac ttg act cct tgg aac tgg gat gca aat ggt aag aaa ctt      2928
Ser Ala Tyr Leu Thr Pro Trp Asn Trp Asp Ala Asn Gly Lys Lys Leu
                965                 970                 975 tct act gat aag gaa aag atg tac tac ttc aat acg cag gcc ggt gca      2976
Ser Thr Asp Lys Glu Lys Met Tyr Tyr Phe Asn Thr Gln Ala Gly Ala
            980                 985                 990 aca act tgg acc ctt cca agc gat  tgg gca aag agc aag  gtt tac ctt    3024
Thr Thr Trp Thr Leu Pro Ser Asp  Trp Ala Lys Ser Lys  Val Tyr Leu
        995                 1000                1005 tac aag  cta act gac caa ggt  aag aca gaa gag caa  gaa cta act        3069
Tyr Lys  Leu Thr Asp Gln Gly  Lys Thr Glu Glu Gln  Glu Leu Thr
    1010                1015                1020 gta aaa  gat ggt aaa att acc  cta gat ctt cta gca  aat caa cca        3114
Val Lys  Asp Gly Lys Ile Thr  Leu Asp Leu Leu Ala  Asn Gln Pro
    1025                1030                1035 tac gtt  ctc tat cgt tcg aaa  caa acc aat cct gaa  atg tca tgg        3159
Tyr Val  Leu Tyr Arg Ser Lys  Gln Thr Asn Pro Glu  Met Ser Trp
```

```
                1040             1045            1050
agt gaa  ggc atg cac atc tat  gac caa gga ttt  aac agt ggt acc        3204
Ser Glu  Gly Met His Ile Tyr  Asp Gln Gly Phe  Asn Ser Gly Thr
   1055              1060               1065 ttg aaa  cat tgg acc att tca  ggc gat gct tct  aag gca gaa att        3249
Leu Lys  His Trp Thr Ile Ser  Gly Asp Ala Ser  Lys Ala Glu Ile
   1070              1075               1080 gtc aag  tct caa ggg gca aac  gat atg ctt cgt  att caa gga aac        3294
Val Lys  Ser Gln Gly Ala Asn  Asp Met Leu Arg  Ile Gln Gly Asn
   1085              1090               1095 aaa gaa  aaa gtt agt ctc act  cag aaa tta act  ggc ttg aaa cca        3339
Lys Glu  Lys Val Ser Leu Thr  Gln Lys Leu Thr  Gly Leu Lys Pro
   1100              1105               1110 aat acc  aag tat gcc gtt tat  gtc ggt gtc gat  aac cgt agt aat        3384
Asn Thr  Lys Tyr Ala Val Tyr  Val Gly Val Asp  Asn Arg Ser Asn
   1115              1120               1125 gcc aag  gcg agc atc act gta  aat act ggt gaa  aaa gaa gtg act        3429
Ala Lys  Ala Ser Ile Thr Val  Asn Thr Gly Glu  Lys Glu Val Thr
   1130              1135               1140 act tat  acc aat aag tct ctc  gcc ctc aac tat  gta aaa gcc tat        3474
Thr Tyr  Thr Asn Lys Ser Leu  Ala Leu Asn Tyr  Val Lys Ala Tyr
   1145              1150               1155 gcc cac  aat aca cgt cgt aac  aat gct aca gtt  gac gat aca agt        3519
Ala His  Asn Thr Arg Arg Asn  Asn Ala Thr Val  Asp Asp Thr Ser
   1160              1165               1170 tac ttc  caa aac atg tac gcc  ttc ttt aca act  gga tcg gac gta        3564
Tyr Phe  Gln Asn Met Tyr Ala  Phe Phe Thr Thr  Gly Ser Asp Val
   1175              1180               1185 tca aat  gtt act ctg aca ttg  agt cgt gaa gct  ggt gat gaa gca        3609
Ser Asn  Val Thr Leu Thr Leu  Ser Arg Glu Ala  Gly Asp Glu Ala
   1190              1195               1200 act tac  ttt gat gaa att cgt  acc ttt gaa aac  aat tca agc atg        3654
Thr Tyr  Phe Asp Glu Ile Arg  Thr Phe Glu Asn  Asn Ser Ser Met
   1205              1210               1215 tac gga  gac aag cat gat aca  ggt aaa ggc acc  ttc aag caa gac        3699
Tyr Gly  Asp Lys His Asp Thr  Gly Lys Gly Thr  Phe Lys Gln Asp
   1220              1225               1230 ttt gaa  aat gtt gct cag ggt  atc ttc cca ttt  gta gtg ggt ggt        3744
Phe Glu  Asn Val Ala Gln Gly  Ile Phe Pro Phe  Val Val Gly Gly
   1235              1240               1245 gtc gaa  ggt gtc gaa gac aac  cgc act cac ttg  tct gaa aaa cac        3789
Val Glu  Gly Val Glu Asp Asn  Arg Thr His Leu  Ser Glu Lys His
   1250              1255               1260 gat cca  tat aca caa cgt ggt  tgg aat ggt aag  aaa gtc gat gat        3834
Asp Pro  Tyr Thr Gln Arg Gly  Trp Asn Gly Lys  Lys Val Asp Asp
   1265              1270               1275 gtt atc  gaa gga aat tgg tca  ctc aag aca aat  gga cta gtg agc        3879
Val Ile  Glu Gly Asn Trp Ser  Leu Lys Thr Asn  Gly Leu Val Ser
   1280              1285               1290 cgt cgt  aac ttg gtt tac caa  act att ccg caa  aac ttc cgt ttt        3924
Arg Arg  Asn Leu Val Tyr Gln  Thr Ile Pro Gln  Asn Phe Arg Phe
   1295              1300               1305 gaa gca  ggt aag acc tac cgt  gta acc ttt gaa  tac gaa gca ggt        3969
Glu Ala  Gly Lys Thr Tyr Arg  Val Thr Phe Glu  Tyr Glu Ala Gly
   1310              1315               1320 tca gac  aat acc tat gct ttt  gta gtc ggt aag  gga gaa ttc cag        4014
Ser Asp  Asn Thr Tyr Ala Phe  Val Val Gly Lys  Gly Glu Phe Gln
   1325              1330               1335 tca ggt  cgt cgt ggt act caa  gca agc aac ttg  gaa atg cat gaa        4059
```

| | | | | | | | | | | | |
|---|---|---|---|---|---|---|---|---|---|---|---|
| Ser | Gly | Arg | Arg | Gly | Thr | Gln | Ala | Ser | Asn | Leu | Glu | Met | His | Glu |
| | 1340 | | | | 1345 | | | | 1350 | | |

```
ttg  cca  aat  act  tgg  aca  gat  tct  aag  aaa  gcc  aag  aag  gca  acc         4104
Leu  Pro  Asn  Thr  Trp  Thr  Asp  Ser  Lys  Lys  Ala  Lys  Lys  Ala  Thr
     1355                1360                     1365 ttc  ctc  gtg  aca  ggt  gca  gaa  aca  ggg  gat  act  tgg  gta  ggt  atc         4149
Phe  Leu  Val  Thr  Gly  Ala  Glu  Thr  Gly  Asp  Thr  Trp  Val  Gly  Ile
     1370                1375                     1380 tac  tca  act  gga  aat  gca  agt  aat  act  cgt  ggt  gat  tct  ggt  gga         4194
Tyr  Ser  Thr  Gly  Asn  Ala  Ser  Asn  Thr  Arg  Gly  Asp  Ser  Gly  Gly
     1385                1390                     1395 aat  gcc  aac  ttc  cgt  ggt  tat  aac  gac  ttc  atg  atg  gat  aat  ctt         4239
Asn  Ala  Asn  Phe  Arg  Gly  Tyr  Asn  Asp  Phe  Met  Met  Asp  Asn  Leu
     1400                1405                     1410 caa  atc  gaa  gaa  att  acc  cta  aca  ggt  aag  atg  ttg  aca  gaa  aat         4284
Gln  Ile  Glu  Glu  Ile  Thr  Leu  Thr  Gly  Lys  Met  Leu  Thr  Glu  Asn
     1415                1420                     1425 gct  ctg  aag  aac  tac  ttg  cca  acg  gtt  gcc  atg  act  aac  tac  acc         4329
Ala  Leu  Lys  Asn  Tyr  Leu  Pro  Thr  Val  Ala  Met  Thr  Asn  Tyr  Thr
     1430                1435                     1440 aaa  gag  tct  atg  gat  gct  ttg  aaa  gag  gcg  gtc  ttt  aac  ctc  agt         4374
Lys  Glu  Ser  Met  Asp  Ala  Leu  Lys  Glu  Ala  Val  Phe  Asn  Leu  Ser
     1445                1450                     1455 cag  gcc  gat  gat  gat  atc  agt  gtg  gaa  gaa  gcg  cgt  gca  gag  att         4419
Gln  Ala  Asp  Asp  Asp  Ile  Ser  Val  Glu  Glu  Ala  Arg  Ala  Glu  Ile
     1460                1465                     1470 gcc  aag  att  gaa  gcc  ttg  aag  aat  gct  ttg  gtt  cag  aag  aaa  acg         4464
Ala  Lys  Ile  Glu  Ala  Leu  Lys  Asn  Ala  Leu  Val  Gln  Lys  Lys  Thr
     1475                1480                     1485 gct  ttg  gta  gca  gat  gac  ttt  gca  agt  ctt  aca  gct  cct  gct  cag         4509
Ala  Leu  Val  Ala  Asp  Asp  Phe  Ala  Ser  Leu  Thr  Ala  Pro  Ala  Gln
     1490                1495                     1500 gct  caa  gaa  ggt  ctt  gca  aat  gcc  ttt  gat  gga  aac  tta  tct  agt         4554
Ala  Gln  Glu  Gly  Leu  Ala  Asn  Ala  Phe  Asp  Gly  Asn  Leu  Ser  Ser
     1505                1510                     1515 tta  tgg  cat  aca  tca  tgg  ggc  gga  gga  gat  gta  ggc  aag  cct  gca         4599
Leu  Trp  His  Thr  Ser  Trp  Gly  Gly  Gly  Asp  Val  Gly  Lys  Pro  Ala
     1520                1525                     1530 acc  atg  gtc  ttg  aaa  gaa  gca  act  gaa  atc  act  gga  ctt  cgt  tat         4644
Thr  Met  Val  Leu  Lys  Glu  Ala  Thr  Glu  Ile  Thr  Gly  Leu  Arg  Tyr
     1535                1540                     1545 gtt  cca  cgt  gga  tca  ggt  tca  aat  ggt  aac  ttg  cgt  gat  gtg  aaa         4689
Val  Pro  Arg  Gly  Ser  Gly  Ser  Asn  Gly  Asn  Leu  Arg  Asp  Val  Lys
     1550                1555                     1560 ctt  gtt  gtg  aca  gat  gag  tct  ggc  aag  gag  cat  acc  ttt  act  gca         4734
Leu  Val  Val  Thr  Asp  Glu  Ser  Gly  Lys  Glu  His  Thr  Phe  Thr  Ala
     1565                1570                     1575 act  gat  tgg  cca  gat  aac  aat  aag  cca  aaa  gac  att  gat  ttt  ggt         4779
Thr  Asp  Trp  Pro  Asp  Asn  Asn  Lys  Pro  Lys  Asp  Ile  Asp  Phe  Gly
     1580                1585                     1590 aag  aca  att  aag  gct  aag  aaa  att  gtc  ctt  aca  ggt  act  aag  act         4824
Lys  Thr  Ile  Lys  Ala  Lys  Lys  Ile  Val  Leu  Thr  Gly  Thr  Lys  Thr
     1595                1600                     1605 tac  gga  gat  ggt  ggc  gat  aaa  tac  caa  tct  gca  gcg  gaa  ctc  atc         4869
Tyr  Gly  Asp  Gly  Gly  Asp  Lys  Tyr  Gln  Ser  Ala  Ala  Glu  Leu  Ile
     1610                1615                     1620 ttt  act  cgt  cca  cag  gta  gca  gaa  aca  cct  ctt  gac  ttg  tca  ggc         4914
Phe  Thr  Arg  Pro  Gln  Val  Ala  Glu  Thr  Pro  Leu  Asp  Leu  Ser  Gly
     1625                1630                     1635
```

-continued

| | | | | | | | | | | | | |
|---|---|---|---|---|---|---|---|---|---|---|---|---|
| tat | gaa | gca | gct | ttg | gct | aag | gct | cag | aaa | tta | aca | gac aaa gac | 4959 |
| Tyr | Glu | Ala | Ala | Leu | Ala | Lys | Ala | Gln | Lys | Leu | Thr | Asp Lys Asp |
| | 1640 | | | | 1645 | | | | | 1650 | | |

```
tat gaa gca gct ttg gct aag gct cag aaa tta aca gac aaa gac      4959
Tyr Glu Ala Ala Leu Ala Lys Ala Gln Lys Leu Thr Asp Lys Asp
    1640                1645                1650 aat caa gag gaa gta gct agc gtt cag gca agc atg aaa tat gcg      5004
Asn Gln Glu Glu Val Ala Ser Val Gln Ala Ser Met Lys Tyr Ala
            1655                1660                1665 acg gat aac cat ctc ttg acg gaa aga atg gtg gaa tac ttt gca      5049
Thr Asp Asn His Leu Leu Thr Glu Arg Met Val Glu Tyr Phe Ala
1670                1675                1680 gat tat ctc aac caa tta aaa gat tct gct acg aaa cca gat gct      5094
Asp Tyr Leu Asn Gln Leu Lys Asp Ser Ala Thr Lys Pro Asp Ala
        1685                1690                1695 cca act gta gag aaa cct gag ttt aaa ctt agc tct gta gct tcc      5139
Pro Thr Val Glu Lys Pro Glu Phe Lys Leu Ser Ser Val Ala Ser
    1700                1705                1710 gat caa ggt aag acg cca gat tat aag caa gaa ata gct aga cca      5184
Asp Gln Gly Lys Thr Pro Asp Tyr Lys Gln Glu Ile Ala Arg Pro
1715                1720                1725 gaa aca cct gaa caa atc ttg cca gca aca ggt gag agt caa ttt      5229
Glu Thr Pro Glu Gln Ile Leu Pro Ala Thr Gly Glu Ser Gln Phe
        1730                1735                1740 gac aca gcc ctc ttc cta gca agt gtt agc cta gcc cta tct gct      5274
Asp Thr Ala Leu Phe Leu Ala Ser Val Ser Leu Ala Leu Ser Ala
    1745                1750                1755 ctc ttt gta gta aaa acg aag aaa gac tag                          5304
Leu Phe Val Val Lys Thr Lys Lys Asp
1760                1765
```

<210> SEQ ID NO 4
<211> LENGTH: 1767
<212> TYPE: PRT
<213> ORGANISM: Streptococcus pneumoniae R6

<400> SEQUENCE: 4

```
Met Asn Lys Gly Leu Phe Glu Lys Arg Cys Lys Tyr Ser Ile Arg Lys
1               5                   10                  15

Phe Ser Leu Gly Val Ala Ser Val Met Ile Gly Ala Thr Phe Phe Gly
            20                  25                  30

Thr Ser Pro Val Leu Ala Asp Ser Val Gln Ser Gly Ser Thr Ala Asn
        35                  40                  45

Leu Pro Ala Asp Leu Ala Thr Ala Leu Ala Thr Ala Lys Glu Asn Asp
    50                  55                  60

Gly His Asp Phe Glu Ala Pro Lys Val Gly Glu Asp Gln Gly Ser Pro
65                  70                  75                  80

Glu Val Thr Asp Gly Pro Lys Thr Glu Glu Glu Leu Leu Ala Leu Glu
                85                  90                  95

Lys Glu Lys Pro Ala Glu Glu Lys Pro Lys Glu Asp Lys Pro Ala Ala
            100                 105                 110

Ala Lys Pro Glu Thr Pro Lys Thr Val Thr Pro Glu Trp Gln Thr Val
        115                 120                 125

Glu Lys Lys Glu Gln Gln Gly Thr Val Thr Ile Arg Glu Glu Lys Gly
    130                 135                 140

Val Arg Tyr Asn Gln Leu Ser Ser Thr Ala Gln Asn Asp Asn Ala Gly
145                 150                 155                 160

Lys Pro Ala Leu Phe Glu Lys Lys Gly Leu Thr Val Asp Ala Asn Gly
                165                 170                 175

Asn Ala Thr Val Asp Leu Thr Phe Lys Asp Asp Ser Glu Lys Gly Lys
            180                 185                 190
```

-continued

```
Ser Arg Phe Gly Val Phe Leu Lys Phe Lys Asp Thr Lys Asn Asn Val
            195                 200                 205

Phe Val Gly Tyr Asp Lys Asp Gly Trp Phe Trp Glu Tyr Lys Ser Pro
            210                 215                 220

Thr Thr Ser Thr Trp Tyr Arg Gly Ser Arg Val Ala Ala Pro Glu Thr
225                 230                 235                 240

Gly Ser Thr Asn Arg Leu Ser Ile Thr Leu Lys Ser Asp Gly Gln Leu
            245                 250                 255

Asn Ala Ser Asn Asn Asp Val Asn Leu Phe Asp Thr Val Thr Leu Pro
            260                 265                 270

Ala Ala Val Asn Asp His Leu Lys Asn Glu Lys Lys Ile Leu Leu Lys
            275                 280                 285

Ala Gly Ser Tyr Asp Asp Glu Arg Thr Val Val Ser Val Lys Thr Asp
            290                 295                 300

Asn Gln Glu Gly Val Lys Thr Glu Asp Thr Pro Ala Glu Lys Glu Thr
305                 310                 315                 320

Gly Pro Glu Val Asp Asp Ser Lys Val Thr Tyr Asp Thr Ile Gln Ser
            325                 330                 335

Lys Val Leu Lys Ala Val Ile Asp Gln Ala Phe Pro Arg Val Lys Glu
            340                 345                 350

Tyr Ser Leu Asn Gly His Thr Leu Pro Gly Gln Val Gln Gln Phe Asn
            355                 360                 365

Gln Val Phe Ile Asn Asn His Arg Ile Thr Pro Glu Val Thr Tyr Lys
            370                 375                 380

Lys Ile Asn Glu Thr Thr Ala Glu Tyr Leu Met Lys Leu Arg Asp Asp
385                 390                 395                 400

Ala His Leu Ile Asn Ala Glu Met Thr Val Arg Leu Gln Val Val Asp
            405                 410                 415

Asn Gln Leu His Phe Asp Val Thr Lys Ile Val Asn His Asn Gln Val
            420                 425                 430

Thr Pro Gly Gln Lys Ile Asp Asp Glu Arg Lys Leu Leu Ser Ser Ile
            435                 440                 445

Ser Phe Leu Gly Asn Ala Leu Val Ser Val Ser Ser Asp Gln Thr Gly
            450                 455                 460

Ala Lys Phe Asp Gly Ala Thr Met Ser Asn Asn Thr His Val Ser Gly
465                 470                 475                 480

Asp Asp His Ile Asp Val Thr Asn Pro Met Lys Asp Leu Ala Lys Gly
            485                 490                 495

Tyr Met Tyr Gly Phe Val Ser Thr Asp Lys Leu Ala Ala Gly Val Trp
            500                 505                 510

Ser Asn Ser Gln Asn Ser Tyr Gly Gly Ser Asn Asp Trp Thr Arg
            515                 520                 525

Leu Thr Ala Tyr Lys Glu Thr Val Gly Asn Ala Asn Tyr Val Gly Ile
            530                 535                 540

His Ser Ser Glu Trp Gln Trp Glu Lys Ala Tyr Lys Gly Ile Val Phe
545                 550                 555                 560

Pro Glu Tyr Thr Lys Glu Leu Pro Ser Ala Lys Val Val Ile Thr Glu
            565                 570                 575

Asp Ala Asn Ala Asp Lys Lys Val Asp Trp Gln Asp Gly Ala Ile Ala
            580                 585                 590

Tyr Arg Ser Ile Met Asn Asn Pro Gln Gly Trp Lys Lys Val Lys Asp
            595                 600                 605
```

-continued

```
Ile Thr Ala Tyr Arg Ile Ala Met Asn Phe Gly Ser Gln Ala Gln Asn
    610                 615                 620
Pro Phe Leu Met Thr Leu Asp Gly Ile Lys Lys Ile Asn Leu His Thr
625                 630                 635                 640
Asp Gly Leu Gly Gln Gly Val Leu Leu Lys Gly Tyr Gly Ser Glu Gly
                645                 650                 655
His Asp Ser Gly His Leu Asn Tyr Ala Asp Ile Gly Lys Arg Ile Gly
            660                 665                 670
Gly Val Glu Asp Phe Lys Thr Leu Ile Glu Lys Ala Lys Lys Tyr Gly
        675                 680                 685
Ala His Leu Gly Ile His Val Asn Ala Ser Glu Thr Tyr Pro Glu Ser
    690                 695                 700
Lys Tyr Phe Asn Glu Lys Ile Leu Arg Lys Asn Pro Asp Gly Ser Tyr
705                 710                 715                 720
Ser Tyr Gly Trp Asn Trp Leu Asp Gln Gly Ile Asn Ile Asp Ala Ala
                725                 730                 735
Tyr Asp Leu Ala His Gly Arg Leu Ala Arg Trp Glu Asp Leu Lys Lys
            740                 745                 750
Lys Leu Gly Asp Gly Leu Asp Phe Ile Tyr Val Asp Val Trp Gly Asn
        755                 760                 765
Gly Gln Ser Gly Asp Asn Gly Ala Trp Ala Thr His Val Leu Ala Lys
    770                 775                 780
Glu Ile Asn Lys Gln Gly Trp Arg Phe Ala Ile Glu Trp Gly His Gly
785                 790                 795                 800
Gly Glu Tyr Asp Ser Thr Phe His His Trp Ala Ala Asp Leu Thr Tyr
                805                 810                 815
Gly Gly Tyr Thr Asn Lys Gly Ile Asn Ser Ala Ile Thr Arg Phe Ile
            820                 825                 830
Arg Asn His Gln Lys Asp Ala Trp Val Gly Asp Tyr Arg Ser Tyr Gly
        835                 840                 845
Gly Ala Ala Asn Tyr Pro Leu Leu Gly Gly Tyr Ser Met Lys Asp Phe
    850                 855                 860
Glu Gly Trp Gln Gly Arg Ser Asp Tyr Asn Gly Tyr Val Thr Asn Leu
865                 870                 875                 880
Phe Ala His Asp Val Met Thr Lys Tyr Phe Gln His Phe Thr Val Ser
                885                 890                 895
Lys Trp Glu Asn Gly Thr Pro Val Thr Met Thr Asp Asn Gly Ser Thr
            900                 905                 910
Tyr Lys Trp Thr Pro Glu Met Arg Val Glu Leu Val Asp Ala Asp Asn
        915                 920                 925
Asn Lys Val Val Thr Arg Lys Ser Asn Asp Val Asn Ser Pro Gln
    930                 935                 940
Tyr Arg Glu Arg Thr Val Thr Leu Asn Gly Arg Val Ile Gln Asp Gly
945                 950                 955                 960
Ser Ala Tyr Leu Thr Pro Trp Asn Trp Asp Ala Asn Gly Lys Lys Leu
                965                 970                 975
Ser Thr Asp Lys Glu Lys Met Tyr Tyr Phe Asn Thr Gln Ala Gly Ala
            980                 985                 990
Thr Thr Trp Thr Leu Pro Ser Asp Trp Ala Lys Ser Lys Val Tyr Leu
        995                 1000                1005
Tyr Lys Leu Thr Asp Gln Gly Lys Thr Glu Glu Gln Glu Leu Thr
    1010                1015                1020
Val Lys Asp Gly Lys Ile Thr Leu Asp Leu Leu Ala Asn Gln Pro
```

-continued

```
            1025                1030                1035

Tyr Val Leu Tyr Arg Ser Lys Gln Thr Asn Pro Glu Met Ser Trp
        1040                1045                1050

Ser Glu Gly Met His Ile Tyr Asp Gln Gly Phe Asn Ser Gly Thr
        1055                1060                1065

Leu Lys His Trp Thr Ile Ser Gly Asp Ala Ser Lys Ala Glu Ile
        1070                1075                1080

Val Lys Ser Gln Gly Ala Asn Asp Met Leu Arg Ile Gln Gly Asn
        1085                1090                1095

Lys Glu Lys Val Ser Leu Thr Gln Lys Leu Thr Gly Leu Lys Pro
        1100                1105                1110

Asn Thr Lys Tyr Ala Val Tyr Val Gly Val Asp Asn Arg Ser Asn
        1115                1120                1125

Ala Lys Ala Ser Ile Thr Val Asn Thr Gly Glu Lys Glu Val Thr
        1130                1135                1140

Thr Tyr Thr Asn Lys Ser Leu Ala Leu Asn Tyr Val Lys Ala Tyr
        1145                1150                1155

Ala His Asn Thr Arg Arg Asn Asn Ala Thr Val Asp Asp Thr Ser
        1160                1165                1170

Tyr Phe Gln Asn Met Tyr Ala Phe Phe Thr Thr Gly Ser Asp Val
        1175                1180                1185

Ser Asn Val Thr Leu Thr Leu Ser Arg Glu Ala Gly Asp Glu Ala
        1190                1195                1200

Thr Tyr Phe Asp Glu Ile Arg Thr Phe Glu Asn Asn Ser Ser Met
        1205                1210                1215

Tyr Gly Asp Lys His Asp Thr Gly Lys Gly Thr Phe Lys Gln Asp
        1220                1225                1230

Phe Glu Asn Val Ala Gln Gly Ile Phe Pro Phe Val Val Gly Gly
        1235                1240                1245

Val Glu Gly Val Glu Asp Asn Arg Thr His Leu Ser Glu Lys His
        1250                1255                1260

Asp Pro Tyr Thr Gln Arg Gly Trp Asn Gly Lys Lys Val Asp Asp
        1265                1270                1275

Val Ile Glu Gly Asn Trp Ser Leu Lys Thr Asn Gly Leu Val Ser
        1280                1285                1290

Arg Arg Asn Leu Val Tyr Gln Thr Ile Pro Gln Asn Phe Arg Phe
        1295                1300                1305

Glu Ala Gly Lys Thr Tyr Arg Val Thr Phe Glu Tyr Glu Ala Gly
        1310                1315                1320

Ser Asp Asn Thr Tyr Ala Phe Val Val Gly Lys Gly Glu Phe Gln
        1325                1330                1335

Ser Gly Arg Arg Gly Thr Gln Ala Ser Asn Leu Glu Met His Glu
        1340                1345                1350

Leu Pro Asn Thr Trp Thr Asp Ser Lys Lys Ala Lys Lys Ala Thr
        1355                1360                1365

Phe Leu Val Thr Gly Ala Glu Thr Gly Asp Thr Trp Val Gly Ile
        1370                1375                1380

Tyr Ser Thr Gly Asn Ala Ser Asn Thr Arg Gly Asp Ser Gly Gly
        1385                1390                1395

Asn Ala Asn Phe Arg Gly Tyr Asn Asp Phe Met Met Asp Asn Leu
        1400                1405                1410

Gln Ile Glu Glu Ile Thr Leu Thr Gly Lys Met Leu Thr Glu Asn
        1415                1420                1425
```

```
Ala Leu Lys Asn Tyr Leu Pro Thr Val Ala Met Thr Asn Tyr Thr
    1430                1435                1440

Lys Glu Ser Met Asp Ala Leu Lys Glu Ala Val Phe Asn Leu Ser
1445                1450                1455

Gln Ala Asp Asp Ile Ser Val Glu Glu Ala Arg Ala Glu Ile
    1460                1465                1470

Ala Lys Ile Glu Ala Leu Lys Asn Ala Leu Val Gln Lys Lys Thr
1475                1480                1485

Ala Leu Val Ala Asp Phe Ala Ser Leu Thr Ala Pro Ala Gln
    1490                1495                1500

Ala Gln Glu Gly Leu Ala Asn Ala Phe Asp Gly Asn Leu Ser Ser
1505                1510                1515

Leu Trp His Thr Ser Trp Gly Gly Gly Asp Val Gly Lys Pro Ala
    1520                1525                1530

Thr Met Val Leu Lys Glu Ala Thr Glu Ile Thr Gly Leu Arg Tyr
1535                1540                1545

Val Pro Arg Gly Ser Gly Ser Asn Gly Asn Leu Arg Asp Val Lys
    1550                1555                1560

Leu Val Val Thr Asp Glu Ser Gly Lys Glu His Thr Phe Thr Ala
1565                1570                1575

Thr Asp Trp Pro Asp Asn Asn Lys Pro Lys Asp Ile Asp Phe Gly
    1580                1585                1590

Lys Thr Ile Lys Ala Lys Lys Ile Val Leu Thr Gly Thr Lys Thr
1595                1600                1605

Tyr Gly Asp Gly Gly Asp Lys Tyr Gln Ser Ala Ala Glu Leu Ile
    1610                1615                1620

Phe Thr Arg Pro Gln Val Ala Glu Thr Pro Leu Asp Leu Ser Gly
1625                1630                1635

Tyr Glu Ala Ala Leu Ala Lys Ala Gln Lys Leu Thr Asp Lys Asp
    1640                1645                1650

Asn Gln Glu Glu Val Ala Ser Val Gln Ala Ser Met Lys Tyr Ala
1655                1660                1665

Thr Asp Asn His Leu Leu Thr Glu Arg Met Val Glu Tyr Phe Ala
    1670                1675                1680

Asp Tyr Leu Asn Gln Leu Lys Asp Ser Ala Thr Lys Pro Asp Ala
1685                1690                1695

Pro Thr Val Glu Lys Pro Glu Phe Lys Leu Ser Ser Val Ala Ser
    1700                1705                1710

Asp Gln Gly Lys Thr Pro Asp Tyr Lys Gln Glu Ile Ala Arg Pro
1715                1720                1725

Glu Thr Pro Glu Gln Ile Leu Pro Ala Thr Gly Glu Ser Gln Phe
    1730                1735                1740

Asp Thr Ala Leu Phe Leu Ala Ser Val Ser Leu Ala Leu Ser Ala
1745                1750                1755

Leu Phe Val Val Lys Thr Lys Lys Asp
    1760                1765

<210> SEQ ID NO 5
<211> LENGTH: 5901
<212> TYPE: DNA
<213> ORGANISM: Bifidobacterium longum NCC2705
<220> FEATURE:
<221> NAME/KEY: CDS
<222> LOCATION: (1)..(5901)
```

<400> SEQUENCE: 5

```
atg aaa aag aag aag act ata tcg gct gcg ctg gca aca gcg tta gcc        48
Met Lys Lys Lys Lys Thr Ile Ser Ala Ala Leu Ala Thr Ala Leu Ala
1               5                   10                  15 tta acc tgc atg ggc agc ggg gga ggt act gcg ttc gca gtg ccc ctg        96
Leu Thr Cys Met Gly Ser Gly Gly Gly Thr Ala Phe Ala Val Pro Leu
            20                  25                  30 tct gat gct gac ttg cag act ttg gca agt cag att cag caa atc aac       144
Ser Asp Ala Asp Leu Gln Thr Leu Ala Ser Gln Ile Gln Gln Ile Asn
        35                  40                  45 gat act tct gat tct gca act gct tcc gag act cct tcc gca caa gcc       192
Asp Thr Ser Asp Ser Ala Thr Ala Ser Glu Thr Pro Ser Ala Gln Ala
    50                  55                  60 gat gcg gtt gaa ggc tgg act att gat tcc aac atc gct cag ggc gac       240
Asp Ala Val Glu Gly Trp Thr Ile Asp Ser Asn Ile Ala Gln Gly Asp
65                  70                  75                  80 gaa atc ctg gag atg gca aac ggt tgg ctg cac ctc aag tcc act gcc       288
Glu Ile Leu Glu Met Ala Asn Gly Trp Leu His Leu Lys Ser Thr Ala
                85                  90                  95 tct aac ggt aat gcg gca gcg aac ccc agc tcc agc aac aac tgg ccg       336
Ser Asn Gly Asn Ala Ala Ala Asn Pro Ser Ser Ser Asn Asn Trp Pro
            100                 105                 110 gca gta gcc gta tgg ggc aca gat tac gac ttc tcc aag gcc ggc tcc       384
Ala Val Ala Val Trp Gly Thr Asp Tyr Asp Phe Ser Lys Ala Gly Ser
        115                 120                 125 ttc cac gcc acc atc aaa tcc ccg cag gaa ggc tcc gcc aac cgc ttc       432
Phe His Ala Thr Ile Lys Ser Pro Gln Glu Gly Ser Ala Asn Arg Phe
    130                 135                 140 ggc ttc tac ctg ggc tac aac gac ccg ggc agc ggc ctg ttc atc ggc       480
Gly Phe Tyr Leu Gly Tyr Asn Asp Pro Gly Ser Gly Leu Phe Ile Gly
145                 150                 155                 160 tac gat tcg gac ggc tgg ttc tgg cag acc tac acc ggt ggt ggt agc       528
Tyr Asp Ser Asp Gly Trp Phe Trp Gln Thr Tyr Thr Gly Gly Gly Ser
                165                 170                 175 ggc agc tgg tac agc ggt gct cgt atc gct gct ccg agc gcc aac gaa       576
Gly Ser Trp Tyr Ser Gly Ala Arg Ile Ala Ala Pro Ser Ala Asn Glu
            180                 185                 190 gag cac gac att cag gtc tcc tgg acc gac gcc aag gtc gcc aca ctg       624
Glu His Asp Ile Gln Val Ser Trp Thr Asp Ala Lys Val Ala Thr Leu
        195                 200                 205 acc gtg gat ggc cag aag gca ttc gat gtc gat tac tcc gca atg acg       672
Thr Val Asp Gly Gln Lys Ala Phe Asp Val Asp Tyr Ser Ala Met Thr
    210                 215                 220 aac ctc tcc aac aag ctt gcc atc aag gcc ggc tcc tgg aag ggg ctg       720
Asn Leu Ser Asn Lys Leu Ala Ile Lys Ala Gly Ser Trp Lys Gly Leu
225                 230                 235                 240 aac cag gtc acc gac gtg tac atc aag gac ttc ccg gag gtt gtc gaa       768
Asn Gln Val Thr Asp Val Tyr Ile Lys Asp Phe Pro Glu Val Val Glu
                245                 250                 255 gcc gcc aag cac gcg gtt tcc ggc aag gtt gtg gac gct gga ggc gct       816
Ala Ala Lys His Ala Val Ser Gly Lys Val Val Asp Ala Gly Gly Ala
            260                 265                 270 gcc att gaa ggc gca aca gtg cgt ttg gat aag acc aag gtg aag acc       864
Ala Ile Glu Gly Ala Thr Val Arg Leu Asp Lys Thr Lys Val Lys Thr
        275                 280                 285 ggt gca gat ggc acc ttc tcc ttc gcc gac att gaa gaa ggc gaa cac       912
Gly Ala Asp Gly Thr Phe Ser Phe Ala Asp Ile Glu Glu Gly Glu His
    290                 295                 300 acg ctt tcg att gcc aag gaa ggc tat gag gac gtc tcc cag cag gtg       960
Thr Leu Ser Ile Ala Lys Glu Gly Tyr Glu Asp Val Ser Gln Gln Val
```

```
Thr Leu Ser Ile Ala Lys Glu Gly Tyr Glu Asp Val Ser Gln Gln Val
305                 310                 315                 320 gcg gtc tcc ggc gcg gac ctt gcc atc gat ccc atc acc ctg aac aaa    1008
Ala Val Ser Gly Ala Asp Leu Ala Ile Asp Pro Ile Thr Leu Asn Lys
                325                 330                 335 acc gtt cag gtc gcc tcc gaa acg ctg aag acc aag aag atg gaa gtt    1056
Thr Val Gln Val Ala Ser Glu Thr Leu Lys Thr Lys Lys Met Glu Val
            340                 345                 350 cag att aag aag aac ttc ccc tct gtg ctg cag tac acg atg acc gac    1104
Gln Ile Lys Lys Asn Phe Pro Ser Val Leu Gln Tyr Thr Met Thr Asp
        355                 360                 365 ggc aag gtg atg tac ggc caa acc aag gat gtg cgc acc gtt gag atc    1152
Gly Lys Val Met Tyr Gly Gln Thr Lys Asp Val Arg Thr Val Glu Ile
370                 375                 380 aac ggc acc aac atc gaa ctg acc gac gat gac gtg acc ttc aag aag    1200
Asn Gly Thr Asn Ile Glu Leu Thr Asp Asp Asp Val Thr Phe Lys Lys
385                 390                 395                 400 gtt tcc gat acc gaa gcc acc tac acg ctg aag gtc aag gat gag gcc    1248
Val Ser Asp Thr Glu Ala Thr Tyr Thr Leu Lys Val Lys Asp Glu Ala
                405                 410                 415 aag aag att gac gcg gtg atc acc gtt cag atc acg gtc aag gcc aac    1296
Lys Lys Ile Asp Ala Val Ile Thr Val Gln Ile Thr Val Lys Ala Asn
            420                 425                 430 cag ctg cac ctc aac gtc acc aag atc aag aac aac ctg tcc gaa ggc    1344
Gln Leu His Leu Asn Val Thr Lys Ile Lys Asn Asn Leu Ser Glu Gly
        435                 440                 445 att cct gag ggc aac ggt gtg gag gag aac gcc atc cag acg ctg tcc    1392
Ile Pro Glu Gly Asn Gly Val Glu Glu Asn Ala Ile Gln Thr Leu Ser
450                 455                 460 ttc ccg aac cag agt ctc gtt tcc gtg cgt tcc agc cag gaa aat gcc    1440
Phe Pro Asn Gln Ser Leu Val Ser Val Arg Ser Ser Gln Glu Asn Ala
465                 470                 475                 480 caa ttc act ggt gct cgt atg tct tcc aac acg cag aag cct ggc gat    1488
Gln Phe Thr Gly Ala Arg Met Ser Ser Asn Thr Gln Lys Pro Gly Asp
                485                 490                 495 acc aac ttc gca gtg acc gaa gat act aac gtc acc gat agc gac tac    1536
Thr Asn Phe Ala Val Thr Glu Asp Thr Asn Val Thr Asp Ser Asp Tyr
            500                 505                 510 acc tac ggc ttc atc tcc ggt gct ggc ctg agt gcc ggc ctg tgg agc    1584
Thr Tyr Gly Phe Ile Ser Gly Ala Gly Leu Ser Ala Gly Leu Trp Ser
        515                 520                 525 aac tcc gag cac gat ggc acc tat gtg gcg gct cct gtg cgc ggc ggc    1632
Asn Ser Glu His Asp Gly Thr Tyr Val Ala Ala Pro Val Arg Gly Gly
530                 535                 540 agc cag aac acg cgt gtc tac gcc acc acc cag cag act ggt gac gcc    1680
Ser Gln Asn Thr Arg Val Tyr Ala Thr Thr Gln Gln Thr Gly Asp Ala
545                 550                 555                 560 acc tcc ctg ggc ctg gcc agc gct ccg tgg tac tac cac cgc acg gtc    1728
Thr Ser Leu Gly Leu Ala Ser Ala Pro Trp Tyr Tyr His Arg Thr Val
                565                 570                 575 acc gat tcc aag ggc aag aag tac acc gtg gcc gaa acc gct ctg ccg    1776
Thr Asp Ser Lys Gly Lys Lys Tyr Thr Val Ala Glu Thr Ala Leu Pro
            580                 585                 590 cag atg gcc gtg gcc atc gcc ggc gac gag aac ggt gac ggt gcc gtc    1824
Gln Met Ala Val Ala Ile Ala Gly Asp Glu Asn Gly Asp Gly Ala Val
        595                 600                 605 aac tgg cag gat ggc gca atc gcc tac cgc gac atc atg aac aac ccg    1872
Asn Trp Gln Asp Gly Ala Ile Ala Tyr Arg Asp Ile Met Asn Asn Pro
610                 615                 620
```

```
tac aag tcc gag gaa gtt ccc gaa ctg gtg gca tgg cgt atc gcc atg    1920
Tyr Lys Ser Glu Glu Val Pro Glu Leu Val Ala Trp Arg Ile Ala Met
625                 630                 635                 640 aac ttc ggc tcc cag gcg cag aac ccg ttc ctc acc acg ctt gac aac    1968
Asn Phe Gly Ser Gln Ala Gln Asn Pro Phe Leu Thr Thr Leu Asp Asn
            645                 650                 655 gtc aag aag gtg gcc ttg aac acc gac ggc ctc ggc cag tcc gtg ctg    2016
Val Lys Lys Val Ala Leu Asn Thr Asp Gly Leu Gly Gln Ser Val Leu
        660                 665                 670 ctc aag ggc tac ggc aat gaa ggc cac gac tcc ggc cac ccg gac tac    2064
Leu Lys Gly Tyr Gly Asn Glu Gly His Asp Ser Gly His Pro Asp Tyr
    675                 680                 685 ggc gat atc ggc cag cgt ctc ggc ggc gcc gac gac atg aac acc atg    2112
Gly Asp Ile Gly Gln Arg Leu Gly Gly Ala Asp Asp Met Asn Thr Met
690                 695                 700 atg gaa gag ggc tcc aag tat ggc gct cgc ttc ggt gtg cac gtc aac    2160
Met Glu Glu Gly Ser Lys Tyr Gly Ala Arg Phe Gly Val His Val Asn
705                 710                 715                 720 gcc tcc gaa atg tat ccg gaa gcc aag gcc ttc agc gag gac atg gtg    2208
Ala Ser Glu Met Tyr Pro Glu Ala Lys Ala Phe Ser Glu Asp Met Val
            725                 730                 735 cgc cgc aac tct gca ggc ggc ctg agc tac ggc tgg aac tgg ctt gat    2256
Arg Arg Asn Ser Ala Gly Gly Leu Ser Tyr Gly Trp Asn Trp Leu Asp
        740                 745                 750 cag ggt gtc ggc atc gac ggc atc tac gat ctg gca tcc ggt tct cgt    2304
Gln Gly Val Gly Ile Asp Gly Ile Tyr Asp Leu Ala Ser Gly Ser Arg
    755                 760                 765 gta agc cgt ttc gct gac ctc agc aag gaa gtc ggc gac aac atg gac    2352
Val Ser Arg Phe Ala Asp Leu Ser Lys Glu Val Gly Asp Asn Met Asp
770                 775                 780 ttc atc tac ctc gat gtg tgg ggc aac ctg act tct tcc ggt tcg gaa    2400
Phe Ile Tyr Leu Asp Val Trp Gly Asn Leu Thr Ser Ser Gly Ser Glu
785                 790                 795                 800 gat tct tgg gaa acc cgc aag atg agc aag atg atc aac gac aac ggc    2448
Asp Ser Trp Glu Thr Arg Lys Met Ser Lys Met Ile Asn Asp Asn Gly
            805                 810                 815 tgg cgt atg acc acc gaa tgg ggt tcc ggc aac gag tac gac tcc acc    2496
Trp Arg Met Thr Thr Glu Trp Gly Ser Gly Asn Glu Tyr Asp Ser Thr
        820                 825                 830 ttc cag cac tgg gca gct gat ctg acc tac ggc ggc tac acc tcc aag    2544
Phe Gln His Trp Ala Ala Asp Leu Thr Tyr Gly Gly Tyr Thr Ser Lys
    835                 840                 845 ggc gag aac tcc gaa gtg atg cgc ttc ctg cgc aac cac cag aag gac    2592
Gly Glu Asn Ser Glu Val Met Arg Phe Leu Arg Asn His Gln Lys Asp
850                 855                 860 agc tgg gtt ggc gac tac ccg caa tac ggc ggc gct gcc aac gcc ccg    2640
Ser Trp Val Gly Asp Tyr Pro Gln Tyr Gly Gly Ala Ala Asn Ala Pro
865                 870                 875                 880 ctg ctc ggc ggc tac aac atg aag gac ttc gaa ggc tgg cag ggc cgc    2688
Leu Leu Gly Gly Tyr Asn Met Lys Asp Phe Glu Gly Trp Gln Gly Arg
            885                 890                 895 aac gac tat gcc gcc tac atc aag aac ctg tac acc cat gat gtg tcc    2736
Asn Asp Tyr Ala Ala Tyr Ile Lys Asn Leu Tyr Thr His Asp Val Ser
        900                 905                 910 act aag ttc atc cag cac ttc aag gtg acc cgc tgg gtc aac aac ccg    2784
Thr Lys Phe Ile Gln His Phe Lys Val Thr Arg Trp Val Asn Asn Pro
    915                 920                 925 ctg ctg acc gcc gac aat ggc aat gcc gct gcc gtg tcc gac ccg aac    2832
Leu Leu Thr Ala Asp Asn Gly Asn Ala Ala Ala Val Ser Asp Pro Asn
930                 935                 940
```

```
acg aac aac ggc aac gag cag att acc ctg aag gat tcc aac ggc aac    2880
Thr Asn Asn Gly Asn Glu Gln Ile Thr Leu Lys Asp Ser Asn Gly Asn
945                 950                 955                 960 gtt gta gta gtc tcc cgt ggt tcc aac gac acc tct agc gca gcc tac    2928
Val Val Val Val Ser Arg Gly Ser Asn Asp Thr Ser Ser Ala Ala Tyr
            965                 970                 975 cgc cag cgc acc atc acc ttc aac ggc gtg aag gtc gca tcc ggt gtg    2976
Arg Gln Arg Thr Ile Thr Phe Asn Gly Val Lys Val Ala Ser Gly Val
        980                 985                 990 gtc tcc gca ggc gat ggc agc gcc act ggc gac gag tcc tac ctg ctg    3024
Val Ser Ala Gly Asp Gly Ser Ala Thr Gly Asp Glu Ser Tyr Leu Leu
    995                 1000                1005 ccg tgg atg tgg gat tcc ttc acc ggc aag ctg gtc aag gat tcc        3069
Pro Trp Met Trp Asp Ser Phe Thr Gly Lys Leu Val Lys Asp Ser
1010                1015                1020 gag cag aag ctc tac cac tgg aac acc aag ggc ggc acc acc acc        3114
Glu Gln Lys Leu Tyr His Trp Asn Thr Lys Gly Gly Thr Thr Thr
1025                1030                1035 tgg acg ctg ccg gac agc tgg aag aac ctc tcc agc gta aag gtg        3159
Trp Thr Leu Pro Asp Ser Trp Lys Asn Leu Ser Ser Val Lys Val
1040                1045                1050 tac cag ctc acc gat cag ggc aag acc aac gag cag acc gtt gcc        3204
Tyr Gln Leu Thr Asp Gln Gly Lys Thr Asn Glu Gln Thr Val Ala
1055                1060                1065 gtc tcc ggc ggc aag gtg acg ctt acc gct gat gcc gaa acc ccg        3249
Val Ser Gly Gly Lys Val Thr Leu Thr Ala Asp Ala Glu Thr Pro
1070                1075                1080 tac gtg gtg tac aag ggc gaa gcc aag cag atc cag gtc aac tgg        3294
Tyr Val Val Tyr Lys Gly Glu Ala Lys Gln Ile Gln Val Asn Trp
1085                1090                1095 agc gaa ggc atg cat gtg gta gac gcc ggc ttc aac ggc ggc tcc        3339
Ser Glu Gly Met His Val Val Asp Ala Gly Phe Asn Gly Gly Ser
1100                1105                1110 aac acc ctc acc gac aac tgg acc gtc gcc gga acc ggc aag gcc        3384
Asn Thr Leu Thr Asp Asn Trp Thr Val Ala Gly Thr Gly Lys Ala
1115                1120                1125 gaa gtt gaa ggc gac aac aac gcc atg ctg cgc ctg acc ggc aag        3429
Glu Val Glu Gly Asp Asn Asn Ala Met Leu Arg Leu Thr Gly Lys
1130                1135                1140 gtc gat gtc tcc cag cgt ctg acc gat ctc aag gct ggc cag aag        3474
Val Asp Val Ser Gln Arg Leu Thr Asp Leu Lys Ala Gly Gln Lys
1145                1150                1155 tac gcg ctg tat gtt ggc gtc gac aac cgc tcc acc ggc gat gca        3519
Tyr Ala Leu Tyr Val Gly Val Asp Asn Arg Ser Thr Gly Asp Ala
1160                1165                1170 tcc gtc acc gta acc agc ggc ggc aag gtg ctg gcc gcc aac tcc        3564
Ser Val Thr Val Thr Ser Gly Gly Lys Val Leu Ala Ala Asn Ser
1175                1180                1185 acc ggc aag tcc atc gcc aag aac tac atc aag gca tac ggc cac        3609
Thr Gly Lys Ser Ile Ala Lys Asn Tyr Ile Lys Ala Tyr Gly His
1190                1195                1200 aac acg aac agc aat acg gaa aat ggc tcc agc tac ttc cag aac        3654
Asn Thr Asn Ser Asn Thr Glu Asn Gly Ser Ser Tyr Phe Gln Asn
1205                1210                1215 atg tac gtg ttc ttc acc gcg cct gag aac ggc gat gcc acg gta        3699
Met Tyr Val Phe Phe Thr Ala Pro Glu Asn Gly Asp Ala Thr Val
1220                1225                1230 acc ctg tct cac aag agc acc gac gga gca cac acc tac ttc gac        3744
Thr Leu Ser His Lys Ser Thr Asp Gly Ala His Thr Tyr Phe Asp
```

```
                      1235                    1240                    1245 gat gtg cgc atc gtg gag aac cag tac tcc ggc atc acc tat gag          3789
Asp Val Arg Ile Val Glu Asn Gln Tyr Ser Gly Ile Thr Tyr Glu
    1250                    1255                    1260 aag gac ggc acg ctg aag tcc ctc acc aac gga ttc gaa aac aac          3834
Lys Asp Gly Thr Leu Lys Ser Leu Thr Asn Gly Phe Glu Asn Asn
    1265                    1270                    1275 gcc cag ggc atc tgg ccg ttc gtc gtc tcc ggt tcc gaa ggc gtt          3879
Ala Gln Gly Ile Trp Pro Phe Val Val Ser Gly Ser Glu Gly Val
    1280                    1285                    1290 gag gac aac cgc atc cac ctc tcc gag ctg cat gct ccg ttc acg          3924
Glu Asp Asn Arg Ile His Leu Ser Glu Leu His Ala Pro Phe Thr
    1295                    1300                    1305 cag gcc ggt tgg gat gtc aag aag atg gac gat gtg ctc gat ggc          3969
Gln Ala Gly Trp Asp Val Lys Lys Met Asp Asp Val Leu Asp Gly
    1310                    1315                    1320 act tgg tct gtg aag gtt aac ggc ctg acc cag aag ggc acg ctg          4014
Thr Trp Ser Val Lys Val Asn Gly Leu Thr Gln Lys Gly Thr Leu
    1325                    1330                    1335 gtc tac cag acg atc ccg cag aac gtg aag ttc gag gcg ggt gcc          4059
Val Tyr Gln Thr Ile Pro Gln Asn Val Lys Phe Glu Ala Gly Ala
    1340                    1345                    1350 aag tac aag gtg agc ttc gac tac cag tcc ggt tcc gat gac atc          4104
Lys Tyr Lys Val Ser Phe Asp Tyr Gln Ser Gly Ser Asp Asp Ile
    1355                    1360                    1365 tac gcc atc gct gtg ggc cag ggt gaa tac tct gcc ggc agc gtg          4149
Tyr Ala Ile Ala Val Gly Gln Gly Glu Tyr Ser Ala Gly Ser Val
    1370                    1375                    1380 aag ctg acc aac ctg aag aag gct ctg ggt gag acc ggc aag gcc          4194
Lys Leu Thr Asn Leu Lys Lys Ala Leu Gly Glu Thr Gly Lys Ala
    1385                    1390                    1395 gag ttc gag ctg acc ggt ggc gtc aac ggc gat tcc tgg ttc ggt          4239
Glu Phe Glu Leu Thr Gly Gly Val Asn Gly Asp Ser Trp Phe Gly
    1400                    1405                    1410 att tac tcg acc gca acc gca cct gat ctg cag ggt tcc acc ggc          4284
Ile Tyr Ser Thr Ala Thr Ala Pro Asp Leu Gln Gly Ser Thr Gly
    1415                    1420                    1425 aat gca cag gac ttc ggc gga tac aag gac ttc gtg ctc gac aac          4329
Asn Ala Gln Asp Phe Gly Gly Tyr Lys Asp Phe Val Leu Asp Asn
    1430                    1435                    1440 ctg aag atc gag cgc atc gag tcc cag acc cgc acc aag gcc gaa          4374
Leu Lys Ile Glu Arg Ile Glu Ser Gln Thr Arg Thr Lys Ala Glu
    1445                    1450                    1455 gcg cag gac aag gtc aag gaa atc cgc ggc aag tac gat tcc aag          4419
Ala Gln Asp Lys Val Lys Glu Ile Arg Gly Lys Tyr Asp Ser Lys
    1460                    1465                    1470 cgt gct gag ctc tcc gat gcc gca tgg cag cag tat cag gac acc          4464
Arg Ala Glu Leu Ser Asp Ala Ala Trp Gln Gln Tyr Gln Asp Thr
    1475                    1480                    1485 ttg gtc aag gct cgc gtg ctc atc aac aag aat ggc gca acc gct          4509
Leu Val Lys Ala Arg Val Leu Ile Asn Lys Asn Gly Ala Thr Ala
    1490                    1495                    1500 gag gac ttc acc aag gca tac gac att ctc gtg gcc ctc gac gag          4554
Glu Asp Phe Thr Lys Ala Tyr Asp Ile Leu Val Ala Leu Asp Glu
    1505                    1510                    1515 tac atg aag acc gct ccc ggc aac gag agc agc gac aag tac gac          4599
Tyr Met Lys Thr Ala Pro Gly Asn Glu Ser Ser Asp Lys Tyr Asp
    1520                    1525                    1530 gtg gca gct gac ggc tcc gat gag ctg ggt ggc tac acc gtg gcc          4644
```

|     |     |     |     |     |     |     |     |     |     |     |     |     |
| --- | --- | --- | --- | --- | --- | --- | --- | --- | --- | --- | --- | --- |
| Val | Ala | Ala | Asp | Gly | Ser | Asp | Glu | Leu | Gly | Gly | Tyr | Thr Val Ala |
| 1535 |     |     |     | 1540 |     |     |     |     | 1545 |     |     |     |

| acg | ggc | agc | gaa | gag | cct | acc | gca | ggc | ctg | ccg | agc | gaa | ggc | ccg | 4689 |
|---|---|---|---|---|---|---|---|---|---|---|---|---|---|---|---|
| Thr | Gly | Ser | Glu | Glu | Pro | Thr | Ala | Gly | Leu | Pro | Ser | Glu | Gly | Pro | |
| 1550 | | | | | 1555 | | | | | 1560 | | | | | |

| gcc | gat | ctg | gca | cag | gat | ggc | aac | gac | agc | acc | cac | tgg | cac | acc | 4734 |
|---|---|---|---|---|---|---|---|---|---|---|---|---|---|---|---|
| Ala | Asp | Leu | Ala | Gln | Asp | Gly | Asn | Asp | Ser | Thr | His | Trp | His | Thr | |
| 1565 | | | | | 1570 | | | | | 1575 | | | | | |

| agc | tgg | agc | gag | aac | gca | gtc | ggc | aac | ggc | acc | gca | tgg | tat | cag | 4779 |
|---|---|---|---|---|---|---|---|---|---|---|---|---|---|---|---|
| Ser | Trp | Ser | Glu | Asn | Ala | Val | Gly | Asn | Gly | Thr | Ala | Trp | Tyr | Gln | |
| 1580 | | | | | 1585 | | | | | 1590 | | | | | |

| ttc | aac | ctc | aac | gaa | ccg | acc | acc | atc | aac | ggc | ctg | cgc | tac | ctg | 4824 |
|---|---|---|---|---|---|---|---|---|---|---|---|---|---|---|---|
| Phe | Asn | Leu | Asn | Glu | Pro | Thr | Thr | Ile | Asn | Gly | Leu | Arg | Tyr | Leu | |
| 1595 | | | | | 1600 | | | | | 1605 | | | | | |

| ccg | cgc | tcc | gga | ggt | atg | aac | gcc | aac | ggc | aag | atc | aag | ggc | tac | 4869 |
|---|---|---|---|---|---|---|---|---|---|---|---|---|---|---|---|
| Pro | Arg | Ser | Gly | Gly | Met | Asn | Ala | Asn | Gly | Lys | Ile | Lys | Gly | Tyr | |
| 1610 | | | | | 1615 | | | | | 1620 | | | | | |

| aag | atc | acg | ctc | act | ctg | gcg | gat | ggc | acc | acc | aag | gat | gtc | gtc | 4914 |
|---|---|---|---|---|---|---|---|---|---|---|---|---|---|---|---|
| Lys | Ile | Thr | Leu | Thr | Leu | Ala | Asp | Gly | Thr | Thr | Lys | Asp | Val | Val | |
| 1625 | | | | | 1630 | | | | | 1635 | | | | | |

| acc | gat | gct | gag | ttc | tcc | acc | acc | acc | atg | tgg | cag | aag | gcc | agc | 4959 |
|---|---|---|---|---|---|---|---|---|---|---|---|---|---|---|---|
| Thr | Asp | Ala | Glu | Phe | Ser | Thr | Thr | Thr | Met | Trp | Gln | Lys | Ala | Ser | |
| 1640 | | | | | 1645 | | | | | 1650 | | | | | |

| ttc | gac | gcc | gtc | gag | aat | gtg | acc | gcc | gta | cgc | ttg | acc | gtc | ctg | 5004 |
|---|---|---|---|---|---|---|---|---|---|---|---|---|---|---|---|
| Phe | Asp | Ala | Val | Glu | Asn | Val | Thr | Ala | Val | Arg | Leu | Thr | Val | Leu | |
| 1655 | | | | | 1660 | | | | | 1665 | | | | | |

| tct | tcc | gca | ggc | cag | agc | gac | tcc | cag | gcc | aac | aag | ttc | gca | tcc | 5049 |
|---|---|---|---|---|---|---|---|---|---|---|---|---|---|---|---|
| Ser | Ser | Ala | Gly | Gln | Ser | Asp | Ser | Gln | Ala | Asn | Lys | Phe | Ala | Ser | |
| 1670 | | | | | 1675 | | | | | 1680 | | | | | |

| gct | gcc | gaa | ctg | cgt | ttg | acc | acg | gac | cgc | gag | gtt | gag | gaa | gag | 5094 |
|---|---|---|---|---|---|---|---|---|---|---|---|---|---|---|---|
| Ala | Ala | Glu | Leu | Arg | Leu | Thr | Thr | Asp | Arg | Glu | Val | Glu | Glu | Glu | |
| 1685 | | | | | 1690 | | | | | 1695 | | | | | |

| act | gtc | gct | ccg | gac | aag | acc | gac | ctc | aac | gac | acc | atc | gcc | aag | 5139 |
|---|---|---|---|---|---|---|---|---|---|---|---|---|---|---|---|
| Thr | Val | Ala | Pro | Asp | Lys | Thr | Asp | Leu | Asn | Asp | Thr | Ile | Ala | Lys | |
| 1700 | | | | | 1705 | | | | | 1710 | | | | | |

| gct | aac | ggt | ctt | aag | gaa | tcc | gac | tac | acg | gct | gaa | agc | tgg | act | 5184 |
|---|---|---|---|---|---|---|---|---|---|---|---|---|---|---|---|
| Ala | Asn | Gly | Leu | Lys | Glu | Ser | Asp | Tyr | Thr | Ala | Glu | Ser | Trp | Thr | |
| 1715 | | | | | 1720 | | | | | 1725 | | | | | |

| gct | ctg | gtc | aag | gcc | cgc | gaa | gct | gca | cag | gcc | gtg | gcg | gat | aac | 5229 |
|---|---|---|---|---|---|---|---|---|---|---|---|---|---|---|---|
| Ala | Leu | Val | Lys | Ala | Arg | Glu | Ala | Ala | Gln | Ala | Val | Ala | Asp | Asn | |
| 1730 | | | | | 1735 | | | | | 1740 | | | | | |

| gat | aag | gcc | acc | gct | tac | gat | gtg | gct | ctg | gcg | ctg | acg | aac | ctc | 5274 |
|---|---|---|---|---|---|---|---|---|---|---|---|---|---|---|---|
| Asp | Lys | Ala | Thr | Ala | Tyr | Asp | Val | Ala | Leu | Ala | Leu | Thr | Asn | Leu | |
| 1745 | | | | | 1750 | | | | | 1755 | | | | | |

| gaa | tcc | gct | atc | gct | ggt | ctc | gag | aag | acc | ggt | gag | gag | cct | ggc | 5319 |
|---|---|---|---|---|---|---|---|---|---|---|---|---|---|---|---|
| Glu | Ser | Ala | Ile | Ala | Gly | Leu | Glu | Lys | Thr | Gly | Glu | Glu | Pro | Gly | |
| 1760 | | | | | 1765 | | | | | 1770 | | | | | |

| cca | ggc | ccg | gtt | gag | gtg | aac | aag | acc | gac | ctg | cag | act | gca | gtg | 5364 |
|---|---|---|---|---|---|---|---|---|---|---|---|---|---|---|---|
| Pro | Gly | Pro | Val | Glu | Val | Asn | Lys | Thr | Asp | Leu | Gln | Thr | Ala | Val | |
| 1775 | | | | | 1780 | | | | | 1785 | | | | | |

| aac | aag | gca | agc | aag | ctc | gag | aag | gcc | gat | tac | acg | acc | aac | tcg | 5409 |
|---|---|---|---|---|---|---|---|---|---|---|---|---|---|---|---|
| Asn | Lys | Ala | Ser | Lys | Leu | Glu | Lys | Ala | Asp | Tyr | Thr | Thr | Asn | Ser | |
| 1790 | | | | | 1795 | | | | | 1800 | | | | | |

| tgg | gaa | gct | ttc | gcc | gag | gca | ctg | aag | gct | gca | cag | cag | gtg | ctc | 5454 |
|---|---|---|---|---|---|---|---|---|---|---|---|---|---|---|---|
| Trp | Glu | Ala | Phe | Ala | Glu | Ala | Leu | Lys | Ala | Ala | Gln | Gln | Val | Leu | |
| 1805 | | | | | 1810 | | | | | 1815 | | | | | |

| gac | aac | aag | aac | gcc | acc | cag | cag | gat | gtg | gat | acc | gca | ctg | agc | 5499 |
|---|---|---|---|---|---|---|---|---|---|---|---|---|---|---|---|
| Asp | Asn | Lys | Asn | Ala | Thr | Gln | Gln | Asp | Val | Asp | Thr | Ala | Leu | Ser | |
| 1820 | | | | | 1825 | | | | | 1830 | | | | | |

-continued

```
gct ctt cag gac gcc atc tcc aag ctg gaa gct acc gcc gag ccg      5544
Ala Leu Gln Asp Ala Ile Ser Lys Leu Glu Ala Thr Ala Glu Pro
    1835                1840                1845 aag ccg aat ccg gaa ccg ggc gtg gtg gac aag gct gct ctg aac      5589
Lys Pro Asn Pro Glu Pro Gly Val Val Asp Lys Ala Ala Leu Asn
1850                1855                1860 gcg acc atc aac aag gcc gcc gcc atc aac ctg ggt ctc tac acc      5634
Ala Thr Ile Asn Lys Ala Ala Ala Ile Asn Leu Gly Leu Tyr Thr
    1865                1870                1875 gac gac tcc gcc aac gct ctg cgc gcc gcg ctg aag aag gcc cgt      5679
Asp Asp Ser Ala Asn Ala Leu Arg Ala Ala Leu Lys Lys Ala Arg
    1880                1885                1890 gag gtc tcc gac aac agc aac gcc acg cag aag cag gtc gac gca      5724
Glu Val Ser Asp Asn Ser Asn Ala Thr Gln Lys Gln Val Asp Ala
    1895                1900                1905 gct cgc gag gct ctc gag aag gca att gcc ggc ttg gtg aag cgt      5769
Ala Arg Glu Ala Leu Glu Lys Ala Ile Ala Gly Leu Val Lys Arg
    1910                1915                1920 acc gct gcc aag ggt gat ggc aac gtt gtt tcc aac acg ggc tcc      5814
Thr Ala Ala Lys Gly Asp Gly Asn Val Val Ser Asn Thr Gly Ser
    1925                1930                1935 gat gtc gcc acg atc gct ctg gct gga ctg ctg ctg gca ggt gct      5859
Asp Val Ala Thr Ile Ala Leu Ala Gly Leu Leu Leu Ala Gly Ala
    1940                1945                1950 ggc gcc gcc atc gcc tac cgt cgc aat cgc gag caa ctg tga          5901
Gly Ala Ala Ile Ala Tyr Arg Arg Asn Arg Glu Gln Leu
    1955                1960                1965
```

<210> SEQ ID NO 6
<211> LENGTH: 1966
<212> TYPE: PRT
<213> ORGANISM: Bifidobacterium longum NCC2705

<400> SEQUENCE: 6

```
Met Lys Lys Lys Lys Thr Ile Ser Ala Ala Leu Ala Thr Ala Leu Ala
1               5                   10                  15

Leu Thr Cys Met Gly Ser Gly Gly Thr Ala Phe Ala Val Pro Leu
            20                  25                  30

Ser Asp Ala Asp Leu Gln Thr Leu Ala Ser Gln Ile Gln Gln Ile Asn
        35                  40                  45

Asp Thr Ser Asp Ser Ala Thr Ala Ser Glu Thr Pro Ser Ala Gln Ala
    50                  55                  60

Asp Ala Val Glu Gly Trp Thr Ile Asp Ser Asn Ile Ala Gln Gly Asp
65                  70                  75                  80

Glu Ile Leu Glu Met Ala Asn Gly Trp Leu His Leu Lys Ser Thr Ala
                85                  90                  95

Ser Asn Gly Asn Ala Ala Ala Asn Pro Ser Ser Ser Asn Asn Trp Pro
            100                 105                 110

Ala Val Ala Val Trp Gly Thr Asp Tyr Asp Phe Ser Lys Ala Gly Ser
        115                 120                 125

Phe His Ala Thr Ile Lys Ser Pro Gln Glu Gly Ser Ala Asn Arg Phe
    130                 135                 140

Gly Phe Tyr Leu Gly Tyr Asn Asp Pro Gly Ser Gly Leu Phe Ile Gly
145                 150                 155                 160

Tyr Asp Ser Asp Gly Trp Phe Trp Gln Thr Tyr Thr Gly Gly Gly Ser
                165                 170                 175

Gly Ser Trp Tyr Ser Gly Ala Arg Ile Ala Ala Pro Ser Ala Asn Glu
            180                 185                 190
```

-continued

```
Glu His Asp Ile Gln Val Ser Trp Thr Asp Ala Lys Val Ala Thr Leu
    195                 200                 205

Thr Val Asp Gly Gln Lys Ala Phe Asp Val Asp Tyr Ser Ala Met Thr
210                 215                 220

Asn Leu Ser Asn Lys Leu Ala Ile Lys Ala Gly Ser Trp Lys Gly Leu
225                 230                 235                 240

Asn Gln Val Thr Asp Val Tyr Ile Lys Asp Phe Pro Glu Val Val Glu
                245                 250                 255

Ala Ala Lys His Ala Val Ser Gly Lys Val Asp Ala Gly Gly Ala
            260                 265                 270

Ala Ile Glu Gly Ala Thr Val Arg Leu Asp Lys Thr Lys Val Lys Thr
    275                 280                 285

Gly Ala Asp Gly Thr Phe Ser Phe Ala Asp Ile Glu Gly Glu His
290                 295                 300

Thr Leu Ser Ile Ala Lys Glu Gly Tyr Glu Asp Val Ser Gln Gln Val
305                 310                 315                 320

Ala Val Ser Gly Ala Asp Leu Ala Ile Asp Pro Ile Thr Leu Asn Lys
                325                 330                 335

Thr Val Gln Val Ala Ser Glu Thr Leu Lys Thr Lys Lys Met Glu Val
            340                 345                 350

Gln Ile Lys Lys Asn Phe Pro Ser Val Leu Gln Tyr Thr Met Thr Asp
    355                 360                 365

Gly Lys Val Met Tyr Gly Gln Thr Lys Asp Val Arg Thr Val Glu Ile
370                 375                 380

Asn Gly Thr Asn Ile Glu Leu Thr Asp Asp Val Thr Phe Lys Lys
385                 390                 395                 400

Val Ser Asp Thr Glu Ala Thr Tyr Thr Leu Lys Val Lys Asp Glu Ala
                405                 410                 415

Lys Lys Ile Asp Ala Val Ile Thr Val Gln Ile Thr Val Lys Ala Asn
            420                 425                 430

Gln Leu His Leu Asn Val Thr Lys Ile Lys Asn Asn Leu Ser Glu Gly
    435                 440                 445

Ile Pro Glu Gly Asn Gly Val Glu Glu Asn Ala Ile Gln Thr Leu Ser
450                 455                 460

Phe Pro Asn Gln Ser Leu Val Ser Val Arg Ser Ser Gln Glu Asn Ala
465                 470                 475                 480

Gln Phe Thr Gly Ala Arg Met Ser Ser Asn Thr Gln Lys Pro Gly Asp
                485                 490                 495

Thr Asn Phe Ala Val Thr Glu Asp Thr Asn Val Thr Asp Ser Asp Tyr
            500                 505                 510

Thr Tyr Gly Phe Ile Ser Gly Ala Gly Leu Ser Ala Gly Leu Trp Ser
    515                 520                 525

Asn Ser Glu His Asp Gly Thr Tyr Val Ala Pro Val Arg Gly Gly
530                 535                 540

Ser Gln Asn Thr Arg Val Tyr Ala Thr Gln Gln Thr Gly Asp Ala
545                 550                 555                 560

Thr Ser Leu Gly Leu Ala Ser Ala Pro Trp Tyr Tyr His Arg Thr Val
                565                 570                 575

Thr Asp Ser Lys Gly Lys Lys Tyr Thr Val Ala Glu Thr Ala Leu Pro
            580                 585                 590

Gln Met Ala Val Ala Ile Ala Gly Asp Glu Asn Gly Asp Gly Ala Val
    595                 600                 605
```

-continued

Asn Trp Gln Asp Gly Ala Ile Ala Tyr Arg Asp Ile Met Asn Asn Pro
    610                 615                 620

Tyr Lys Ser Glu Glu Val Pro Glu Leu Val Ala Trp Arg Ile Ala Met
625                 630                 635                 640

Asn Phe Gly Ser Gln Ala Gln Asn Pro Phe Leu Thr Thr Leu Asp Asn
                645                 650                 655

Val Lys Lys Val Ala Leu Asn Thr Asp Gly Leu Gly Gln Ser Val Leu
            660                 665                 670

Leu Lys Gly Tyr Gly Asn Glu Gly His Asp Ser Gly His Pro Asp Tyr
        675                 680                 685

Gly Asp Ile Gly Gln Arg Leu Gly Gly Ala Asp Met Asn Thr Met
    690                 695                 700

Met Glu Glu Gly Ser Lys Tyr Gly Ala Arg Phe Gly Val His Val Asn
705                 710                 715                 720

Ala Ser Glu Met Tyr Pro Glu Ala Lys Ala Phe Ser Glu Asp Met Val
                725                 730                 735

Arg Arg Asn Ser Ala Gly Gly Leu Ser Tyr Gly Trp Asn Trp Leu Asp
            740                 745                 750

Gln Gly Val Gly Ile Asp Gly Ile Tyr Asp Leu Ala Ser Gly Ser Arg
        755                 760                 765

Val Ser Arg Phe Ala Asp Leu Ser Lys Glu Val Gly Asp Asn Met Asp
    770                 775                 780

Phe Ile Tyr Leu Asp Val Trp Gly Asn Leu Thr Ser Ser Gly Ser Glu
785                 790                 795                 800

Asp Ser Trp Glu Thr Arg Lys Met Ser Lys Met Ile Asn Asp Asn Gly
                805                 810                 815

Trp Arg Met Thr Thr Glu Trp Gly Ser Gly Asn Glu Tyr Asp Ser Thr
            820                 825                 830

Phe Gln His Trp Ala Ala Asp Leu Thr Tyr Gly Gly Tyr Thr Ser Lys
        835                 840                 845

Gly Glu Asn Ser Glu Val Met Arg Phe Leu Arg Asn His Gln Lys Asp
    850                 855                 860

Ser Trp Val Gly Asp Tyr Pro Gln Tyr Gly Gly Ala Ala Asn Ala Pro
865                 870                 875                 880

Leu Leu Gly Gly Tyr Asn Met Lys Asp Phe Glu Gly Trp Gln Gly Arg
                885                 890                 895

Asn Asp Tyr Ala Ala Tyr Ile Lys Asn Leu Tyr Thr His Asp Val Ser
            900                 905                 910

Thr Lys Phe Ile Gln His Phe Lys Val Thr Arg Trp Val Asn Asn Pro
        915                 920                 925

Leu Leu Thr Ala Asp Asn Gly Asn Ala Ala Ala Val Ser Asp Pro Asn
    930                 935                 940

Thr Asn Asn Gly Asn Glu Gln Ile Thr Leu Lys Asp Ser Asn Gly Asn
945                 950                 955                 960

Val Val Val Val Ser Arg Gly Ser Asn Asp Thr Ser Ser Ala Ala Tyr
                965                 970                 975

Arg Gln Arg Thr Ile Thr Phe Asn Gly Val Lys Val Ala Ser Gly Val
            980                 985                 990

Val Ser Ala Gly Asp Gly Ser Ala Thr Gly Asp Glu Ser Tyr Leu Leu
        995                 1000                1005

Pro Trp Met Trp Asp Ser Phe Thr Gly Lys Leu Val Lys Asp Ser
    1010                1015                1020

Glu Gln Lys Leu Tyr His Trp Asn Thr Lys Gly Gly Thr Thr Thr

-continued

```
                1025                1030                1035
Trp Thr Leu Pro Asp Ser Trp Lys Asn Leu Ser Ser Val Lys Val
    1040                1045                1050

Tyr Gln Leu Thr Asp Gln Gly Lys Thr Asn Glu Gln Thr Val Ala
    1055                1060                1065

Val Ser Gly Gly Lys Val Thr Leu Thr Ala Asp Ala Glu Thr Pro
    1070                1075                1080

Tyr Val Val Tyr Lys Gly Glu Ala Lys Gln Ile Gln Val Asn Trp
    1085                1090                1095

Ser Glu Gly Met His Val Val Asp Ala Gly Phe Asn Gly Gly Ser
    1100                1105                1110

Asn Thr Leu Thr Asp Asn Trp Thr Val Ala Gly Thr Gly Lys Ala
    1115                1120                1125

Glu Val Glu Gly Asp Asn Asn Ala Met Leu Arg Leu Thr Gly Lys
    1130                1135                1140

Val Asp Val Ser Gln Arg Leu Thr Asp Leu Lys Ala Gly Gln Lys
    1145                1150                1155

Tyr Ala Leu Tyr Val Gly Val Asp Asn Arg Ser Thr Gly Asp Ala
    1160                1165                1170

Ser Val Thr Val Thr Ser Gly Gly Lys Val Leu Ala Ala Asn Ser
    1175                1180                1185

Thr Gly Lys Ser Ile Ala Lys Asn Tyr Ile Lys Ala Tyr Gly His
    1190                1195                1200

Asn Thr Asn Ser Asn Thr Glu Asn Gly Ser Ser Tyr Phe Gln Asn
    1205                1210                1215

Met Tyr Val Phe Phe Thr Ala Pro Glu Asn Gly Asp Ala Thr Val
    1220                1225                1230

Thr Leu Ser His Lys Ser Thr Asp Gly Ala His Thr Tyr Phe Asp
    1235                1240                1245

Asp Val Arg Ile Val Glu Asn Gln Tyr Ser Gly Ile Thr Tyr Glu
    1250                1255                1260

Lys Asp Gly Thr Leu Lys Ser Leu Thr Asn Gly Phe Glu Asn Asn
    1265                1270                1275

Ala Gln Gly Ile Trp Pro Phe Val Val Ser Gly Ser Glu Gly Val
    1280                1285                1290

Glu Asp Asn Arg Ile His Leu Ser Glu Leu His Ala Pro Phe Thr
    1295                1300                1305

Gln Ala Gly Trp Asp Val Lys Lys Met Asp Asp Val Leu Asp Gly
    1310                1315                1320

Thr Trp Ser Val Lys Val Asn Gly Leu Thr Gln Lys Gly Thr Leu
    1325                1330                1335

Val Tyr Gln Thr Ile Pro Gln Asn Val Lys Phe Glu Ala Gly Ala
    1340                1345                1350

Lys Tyr Lys Val Ser Phe Asp Tyr Gln Ser Gly Ser Asp Asp Ile
    1355                1360                1365

Tyr Ala Ile Ala Val Gly Gln Gly Glu Tyr Ser Ala Gly Ser Val
    1370                1375                1380

Lys Leu Thr Asn Leu Lys Lys Ala Leu Gly Glu Thr Gly Lys Ala
    1385                1390                1395

Glu Phe Glu Leu Thr Gly Gly Val Asn Gly Asp Ser Trp Phe Gly
    1400                1405                1410

Ile Tyr Ser Thr Ala Thr Ala Pro Asp Leu Gln Gly Ser Thr Gly
    1415                1420                1425
```

-continued

```
Asn Ala Gln Asp Phe Gly Gly Tyr Lys Asp Phe Val Leu Asp Asn
            1430            1435            1440

Leu Lys Ile Glu Arg Ile Glu Ser Gln Thr Arg Thr Lys Ala Glu
    1445            1450            1455

Ala Gln Asp Lys Val Lys Glu Ile Arg Gly Lys Tyr Asp Ser Lys
1460            1465            1470

Arg Ala Glu Leu Ser Asp Ala Ala Trp Gln Gln Tyr Gln Asp Thr
        1475            1480            1485

Leu Val Lys Ala Arg Val Leu Ile Asn Lys Asn Gly Ala Thr Ala
    1490            1495            1500

Glu Asp Phe Thr Lys Ala Tyr Asp Ile Leu Val Ala Leu Asp Glu
1505            1510            1515

Tyr Met Lys Thr Ala Pro Gly Asn Glu Ser Ser Asp Lys Tyr Asp
        1520            1525            1530

Val Ala Ala Asp Gly Ser Asp Glu Leu Gly Gly Tyr Thr Val Ala
    1535            1540            1545

Thr Gly Ser Glu Glu Pro Thr Ala Gly Leu Pro Ser Glu Gly Pro
1550            1555            1560

Ala Asp Leu Ala Gln Asp Gly Asn Asp Ser Thr His Trp His Thr
        1565            1570            1575

Ser Trp Ser Glu Asn Ala Val Gly Asn Gly Thr Ala Trp Tyr Gln
    1580            1585            1590

Phe Asn Leu Asn Glu Pro Thr Thr Ile Asn Gly Leu Arg Tyr Leu
1595            1600            1605

Pro Arg Ser Gly Gly Met Asn Ala Asn Gly Lys Ile Lys Gly Tyr
        1610            1615            1620

Lys Ile Thr Leu Thr Leu Ala Asp Gly Thr Thr Lys Asp Val Val
    1625            1630            1635

Thr Asp Ala Glu Phe Ser Thr Thr Thr Met Trp Gln Lys Ala Ser
1640            1645            1650

Phe Asp Ala Val Glu Asn Val Thr Ala Val Arg Leu Thr Val Leu
        1655            1660            1665

Ser Ser Ala Gly Gln Ser Asp Ser Gln Ala Asn Lys Phe Ala Ser
    1670            1675            1680

Ala Ala Glu Leu Arg Leu Thr Thr Asp Arg Glu Val Glu Glu Glu
1685            1690            1695

Thr Val Ala Pro Asp Lys Thr Asp Leu Asn Asp Thr Ile Ala Lys
        1700            1705            1710

Ala Asn Gly Leu Lys Glu Ser Asp Tyr Thr Ala Glu Ser Trp Thr
    1715            1720            1725

Ala Leu Val Lys Ala Arg Glu Ala Ala Gln Ala Val Ala Asp Asn
1730            1735            1740

Asp Lys Ala Thr Ala Tyr Asp Val Ala Leu Ala Leu Thr Asn Leu
        1745            1750            1755

Glu Ser Ala Ile Ala Gly Leu Glu Lys Thr Gly Glu Glu Pro Gly
    1760            1765            1770

Pro Gly Pro Val Glu Val Asn Lys Thr Asp Leu Gln Thr Ala Val
1775            1780            1785

Asn Lys Ala Ser Lys Leu Glu Lys Ala Asp Tyr Thr Thr Asn Ser
        1790            1795            1800

Trp Glu Ala Phe Ala Glu Ala Leu Lys Ala Ala Gln Gln Val Leu
    1805            1810            1815
```

-continued

```
Asp Asn Lys Asn Ala Thr Gln Gln Asp Val Asp Thr Ala Leu Ser
    1820              1825                1830

Ala Leu Gln Asp Ala Ile Ser Lys Leu Glu Ala Thr Ala Glu Pro
    1835                1840                1845

Lys Pro Asn Pro Glu Pro Gly Val Val Asp Lys Ala Ala Leu Asn
    1850                1855                1860

Ala Thr Ile Asn Lys Ala Ala Ala Ile Asn Leu Gly Leu Tyr Thr
    1865                1870                1875

Asp Asp Ser Ala Asn Ala Leu Arg Ala Ala Leu Lys Lys Ala Arg
    1880                1885                1890

Glu Val Ser Asp Asn Ser Asn Ala Thr Gln Lys Gln Val Asp Ala
    1895                1900                1905

Ala Arg Glu Ala Leu Glu Lys Ala Ile Ala Gly Leu Val Lys Arg
    1910                1915                1920

Thr Ala Ala Lys Gly Asp Gly Asn Val Val Ser Asn Thr Gly Ser
    1925                1930                1935

Asp Val Ala Thr Ile Ala Leu Ala Gly Leu Leu Leu Ala Gly Ala
    1940                1945                1950

Gly Ala Ala Ile Ala Tyr Arg Arg Asn Arg Glu Gln Leu
    1955                1960                1965

<210> SEQ ID NO 7
<211> LENGTH: 5061
<212> TYPE: DNA
<213> ORGANISM: Clostridium perfringens str. 13
<220> FEATURE:
<221> NAME/KEY: CDS
<222> LOCATION: (1)..(5061)

<400> SEQUENCE: 7 atg ggt aga aaa tgc atg aat aag aag att gcc gca ata ata gca gct      48
Met Gly Arg Lys Cys Met Asn Lys Lys Ile Ala Ala Ile Ile Ala Ala
1               5                   10                  15 gca gtt att gta gga caa tta cca att tca gta ctt gct aca cct gtt      96
Ala Val Ile Val Gly Gln Leu Pro Ile Ser Val Leu Ala Thr Pro Val
                20                  25                  30 aat gaa gct gga gat gag att aat agt gaa tca gct gaa att tta act     144
Asn Glu Ala Gly Asp Glu Ile Asn Ser Glu Ser Ala Glu Ile Leu Thr
            35                  40                  45 aat agt gat gaa gaa gct gag gct tat att caa aac tat gat aga cca     192
Asn Ser Asp Glu Glu Ala Glu Ala Tyr Ile Gln Asn Tyr Asp Arg Pro
        50                  55                  60 gag ggg att act tgg aca aaa tta gca ggc tca gga agt gtt gag gta     240
Glu Gly Ile Thr Trp Thr Lys Leu Ala Gly Ser Gly Ser Val Glu Val
65                  70                  75                  80 act gat gga ttt tta tca gtt act aat aat gga gat tat aga att atg     288
Thr Asp Gly Phe Leu Ser Val Thr Asn Asn Gly Asp Tyr Arg Ile Met
                85                  90                  95 gaa gat caa tcg cct aat ata aaa aat ggt gag tta gaa agt aaa ttt     336
Glu Asp Gln Ser Pro Asn Ile Lys Asn Gly Glu Leu Glu Ser Lys Phe
            100                 105                 110 aca gtt gga ggt tct caa act gga ata ata ttt aga gca act gag tca     384
Thr Val Gly Gly Ser Gln Thr Gly Ile Ile Phe Arg Ala Thr Glu Ser
        115                 120                 125 aac tat gga atg atc aac tat aac tca ggt act ggc tgg gtt ata gaa     432
Asn Tyr Gly Met Ile Asn Tyr Asn Ser Gly Thr Gly Trp Val Ile Glu
    130                 135                 140 aat aaa aat agt tgg gag gat att aca gga cca aaa cta aat aat gga     480
Asn Lys Asn Ser Trp Glu Asp Ile Thr Gly Pro Lys Leu Asn Asn Gly
```

```
                145                 150                 155                 160
gat gtt gta aca gtt aag gct act ttt gtt gaa aag cat tta act gtt      528
Asp Val Val Thr Val Lys Ala Thr Phe Val Glu Lys His Leu Thr Val
                    165                 170                 175 aat gtt tct gta aat gat gga gaa ttt gaa act ata tat gat aaa gaa      576
Asn Val Ser Val Asn Asp Gly Glu Phe Glu Thr Ile Tyr Asp Lys Glu
                180                 185                 190 tca gat tta att cca tta caa gct ggt aaa gtt gga tat aga gga tgg      624
Ser Asp Leu Ile Pro Leu Gln Ala Gly Lys Val Gly Tyr Arg Gly Trp
            195                 200                 205 ggt aac gct aaa act acc aaa ttt gat tat att aag tat gct cct atg      672
Gly Asn Ala Lys Thr Thr Lys Phe Asp Tyr Ile Lys Tyr Ala Pro Met
        210                 215                 220 act ata gat aag gga cct ata gta tca ata aat gaa gta aat gta gaa      720
Thr Ile Asp Lys Gly Pro Ile Val Ser Ile Asn Glu Val Asn Val Glu
225                 230                 235                 240 act tat cca aga gtt aag cct att tta cca tca agt gtt aca gta aat      768
Thr Tyr Pro Arg Val Lys Pro Ile Leu Pro Ser Ser Val Thr Val Asn
                245                 250                 255 cat gaa aat ggt atg tct agt att aag gat gtt tct tgg aat tat ata      816
His Glu Asn Gly Met Ser Ser Ile Lys Asp Val Ser Trp Asn Tyr Ile
            260                 265                 270 cct aag gaa agt tat tca aag cca ggt aca ttc aaa gtt gaa ggt aca      864
Pro Lys Glu Ser Tyr Ser Lys Pro Gly Thr Phe Lys Val Glu Gly Thr
        275                 280                 285 gtt gaa ggt aca gat gta aaa gca ata gct aat gta act gta agt tca      912
Val Glu Gly Thr Asp Val Lys Ala Ile Ala Asn Val Thr Val Ser Ser
    290                 295                 300 gat tta gca tat tat gaa act aat ttt gaa aca gaa gaa aca aga gga      960
Asp Leu Ala Tyr Tyr Glu Thr Asn Phe Glu Thr Glu Glu Thr Arg Gly
305                 310                 315                 320 gat tgg caa gtt gta caa gga gga gga tct cca agt tat gaa gag ggt     1008
Asp Trp Gln Val Val Gln Gly Gly Gly Ser Pro Ser Tyr Glu Glu Gly
                325                 330                 335 aaa gta aaa ata cct atg aat gga gta tca atc gct gtt gat atg aat     1056
Lys Val Lys Ile Pro Met Asn Gly Val Ser Ile Ala Val Asp Met Asn
            340                 345                 350 tct cca gag gtt aag aac ttt act tat gaa act gat ttt tct gtt gat     1104
Ser Pro Glu Val Lys Asn Phe Thr Tyr Glu Thr Asp Phe Ser Val Asp
        355                 360                 365 aat aat gga gga aga ata ggt cta tta ttt aga tat gta tca gaa act     1152
Asn Asn Gly Gly Arg Ile Gly Leu Leu Phe Arg Tyr Val Ser Glu Thr
    370                 375                 380 gag tgg gga gct gtt tgc tat gat aat ggt tct tgg gta tgg aaa act     1200
Glu Trp Gly Ala Val Cys Tyr Asp Asn Gly Ser Trp Val Trp Lys Thr
385                 390                 395                 400 gga gat ggc aaa tat ggt aat ttc cca gga aca ttt aca cca gag cca     1248
Gly Asp Gly Lys Tyr Gly Asn Phe Pro Gly Thr Phe Thr Pro Glu Pro
                405                 410                 415 gga aaa act tac aga ata aag ctt aaa gta gaa gat aca aat att act     1296
Gly Lys Thr Tyr Arg Ile Lys Leu Lys Val Glu Asp Thr Asn Ile Thr
            420                 425                 430 atg tgg gtt gat gga gag aaa ata ggg caa gtt gca gta tct aat tta     1344
Met Trp Val Asp Gly Glu Lys Ile Gly Gln Val Ala Val Ser Asn Leu
        435                 440                 445 cca gat gta aga gga aaa gtt ggc tta act gga tgg ttt gga aat aaa     1392
Pro Asp Val Arg Gly Lys Val Gly Leu Thr Gly Trp Phe Gly Asn Lys
    450                 455                 460 aat gtt act tta gat aat ctt gtt gtt gag gaa tta ggt gga ata atg     1440
```

```
Asn Val Thr Leu Asp Asn Leu Val Val Glu Glu Leu Gly Gly Ile Met
465                 470                 475                 480 gca cca gaa gta ggt cca tta gaa gaa caa agt ata gaa tca gat tct       1488
Ala Pro Glu Val Gly Pro Leu Glu Glu Gln Ser Ile Glu Ser Asp Ser
                    485                 490                 495 atg aaa gtt gtt tta gat aat aga ttc cca act gtt att aga tat gag       1536
Met Lys Val Val Leu Asp Asn Arg Phe Pro Thr Val Ile Arg Tyr Glu
            500                 505                 510 tgg aaa gga act gaa gat gtt tta tca gga gca tct gta gat gat tta       1584
Trp Lys Gly Thr Glu Asp Val Leu Ser Gly Ala Ser Val Asp Asp Leu
        515                 520                 525 gaa gct caa tat atg gtt gaa att aat ggt gaa aag aga att cca aaa       1632
Glu Ala Gln Tyr Met Val Glu Ile Asn Gly Glu Lys Arg Ile Pro Lys
    530                 535                 540 gta act agt gaa ttt gca aat aat gaa ggt ata tat aca tta aac ttt       1680
Val Thr Ser Glu Phe Ala Asn Asn Glu Gly Ile Tyr Thr Leu Asn Phe
545                 550                 555                 560 gaa gat ata gga atg act att act tta aag atg act gtt aat gaa aat       1728
Glu Asp Ile Gly Met Thr Ile Thr Leu Lys Met Thr Val Asn Glu Asn
                    565                 570                 575 aaa tta aga atg gaa gtt act gat att caa gaa ggg gat gtt aaa ctt       1776
Lys Leu Arg Met Glu Val Thr Asp Ile Gln Glu Gly Asp Val Lys Leu
            580                 585                 590 caa aca tta aat ttc cca aat cat agt tta gct tca gta agc agt tta       1824
Gln Thr Leu Asn Phe Pro Asn His Ser Leu Ala Ser Val Ser Ser Leu
        595                 600                 605 aat aat ggt aaa aca gcc tct gtt cta aca act ggt gac tgg aat aac       1872
Asn Asn Gly Lys Thr Ala Ser Val Leu Thr Thr Gly Asp Trp Asn Asn
    610                 615                 620 ata aat gaa gag ttt aca gat gtt gct aag gca aaa cca ggg gtt aag       1920
Ile Asn Glu Glu Phe Thr Asp Val Ala Lys Ala Lys Pro Gly Val Lys
625                 630                 635                 640 ggt aaa act tat gca ttt ata aat gat gat aag ttt gct gtt act ata       1968
Gly Lys Thr Tyr Ala Phe Ile Asn Asp Asp Lys Phe Ala Val Thr Ile
                    645                 650                 655 aat aat aat act att gaa ggt gga aat agg gtt gta tta aca aca gaa       2016
Asn Asn Asn Thr Ile Glu Gly Gly Asn Arg Val Val Leu Thr Thr Glu
            660                 665                 670 aat gat act ctt cct gat aat aca aac tat aag aaa gtt gga ata tca       2064
Asn Asp Thr Leu Pro Asp Asn Thr Asn Tyr Lys Lys Val Gly Ile Ser
        675                 680                 685 aac ggt act tgg act tat aaa gaa ata ctt caa gat aca aca gat caa       2112
Asn Gly Thr Trp Thr Tyr Lys Glu Ile Leu Gln Asp Thr Thr Asp Gln
    690                 695                 700 gga agt aag cta tat caa ggt gaa aag cca tgg tca gaa gta att ata       2160
Gly Ser Lys Leu Tyr Gln Gly Glu Lys Pro Trp Ser Glu Val Ile Ile
705                 710                 715                 720 gca aga gat gag aat gaa gat ggt caa gta gat tgg caa gat ggt gct       2208
Ala Arg Asp Glu Asn Glu Asp Gly Gln Val Asp Trp Gln Asp Gly Ala
                    725                 730                 735 att caa tat aga aaa aat atg aaa att cca gta ggt gga gaa gaa ata       2256
Ile Gln Tyr Arg Lys Asn Met Lys Ile Pro Val Gly Gly Glu Glu Ile
            740                 745                 750 aaa aat caa atg tca tat att gat ttt aat att gga tac act caa aat       2304
Lys Asn Gln Met Ser Tyr Ile Asp Phe Asn Ile Gly Tyr Thr Gln Asn
        755                 760                 765 cca ttc tta aga tca tta gat aca att aaa aag ctt tca aat tat aca       2352
Pro Phe Leu Arg Ser Leu Asp Thr Ile Lys Lys Leu Ser Asn Tyr Thr
    770                 775                 780
```

```
gat gga ttt gga caa tta gtt ctt cat aag gga tat caa gga gaa gga      2400
Asp Gly Phe Gly Gln Leu Val Leu His Lys Gly Tyr Gln Gly Glu Gly
785                 790                 795                 800 cat gac gac tct cat cca gac tat ggc gga cat att ggt atg aga caa      2448
His Asp Asp Ser His Pro Asp Tyr Gly Gly His Ile Gly Met Arg Gln
            805                 810                 815 ggt ggt aag gaa gac ttc aat acc tta ata gaa caa ggt aag gaa tat      2496
Gly Gly Lys Glu Asp Phe Asn Thr Leu Ile Glu Gln Gly Lys Glu Tyr
        820                 825                 830 aat gct aaa ata ggt gtt cat ata aat gca acc gaa tat act atg gat      2544
Asn Ala Lys Ile Gly Val His Ile Asn Ala Thr Glu Tyr Thr Met Asp
    835                 840                 845 gcg ttt gaa tat cca act gaa tta gtt aac gaa aat gct cca gga tgg      2592
Ala Phe Glu Tyr Pro Thr Glu Leu Val Asn Glu Asn Ala Pro Gly Trp
850                 855                 860 gga tgg tta gac caa gct tat tat gta aat caa aga gga gat ata act      2640
Gly Trp Leu Asp Gln Ala Tyr Tyr Val Asn Gln Arg Gly Asp Ile Thr
865                 870                 875                 880 agt ggt gaa tta ttc aga aga ctt gat atg tta atg gaa gat gca cca      2688
Ser Gly Glu Leu Phe Arg Arg Leu Asp Met Leu Met Glu Asp Ala Pro
            885                 890                 895 gaa cta gga tgg att tac gtt gac gtt tat aca ggt aat gga tgg aat      2736
Glu Leu Gly Trp Ile Tyr Val Asp Val Tyr Thr Gly Asn Gly Trp Asn
        900                 905                 910 gct cat caa tta gga gaa aag ata aat gat tat gga att atg att gca      2784
Ala His Gln Leu Gly Glu Lys Ile Asn Asp Tyr Gly Ile Met Ile Ala
    915                 920                 925 aca gaa atg aat gga cca tta gag caa cat gtt cca tgg act cac tgg      2832
Thr Glu Met Asn Gly Pro Leu Glu Gln His Val Pro Trp Thr His Trp
930                 935                 940 ggt gga gat cct gca tat cca aac aag gga aat gca agt aaa ata atg      2880
Gly Gly Asp Pro Ala Tyr Pro Asn Lys Gly Asn Ala Ser Lys Ile Met
945                 950                 955                 960 aga ttt atg aaa aat gat act caa gat tca ttc tta gca gat cca tta      2928
Arg Phe Met Lys Asn Asp Thr Gln Asp Ser Phe Leu Ala Asp Pro Leu
            965                 970                 975 gta aaa ggt aat aag cat tta tta tca ggt gga tgg gga act aga cat      2976
Val Lys Gly Asn Lys His Leu Leu Ser Gly Gly Trp Gly Thr Arg His
        980                 985                 990 gat ata gaa ggt gct tat ggt aca gaa gta ttc tat aat caa gta tta      3024
Asp Ile Glu Gly Ala Tyr Gly Thr Glu Val Phe Tyr Asn Gln Val Leu
    995                 1000                1005 cct act aag tat tta caa cac ttc caa ata act aag atg agc gaa          3069
Pro Thr Lys Tyr Leu Gln His Phe Gln Ile Thr Lys Met Ser Glu
1010                1015                1020 aat gaa gta tta ttt gaa aat gga gtt aag gct gtt aga gaa aac          3114
Asn Glu Val Leu Phe Glu Asn Gly Val Lys Ala Val Arg Glu Asn
1025                1030                1035 tct aat ata aat tac tat aga aat gat aga tta gtt gct act act          3159
Ser Asn Ile Asn Tyr Tyr Arg Asn Asp Arg Leu Val Ala Thr Thr
1040                1045                1050 cca gaa aat tca att gga aat act ggt ata ggg gat act caa tta          3204
Pro Glu Asn Ser Ile Gly Asn Thr Gly Ile Gly Asp Thr Gln Leu
1055                1060                1065 ttc tta cca tgg aat cct gtt gat gag gca aat agt gaa aag ata          3249
Phe Leu Pro Trp Asn Pro Val Asp Glu Ala Asn Ser Glu Lys Ile
1070                1075                1080 tat cac tgg aat cca tta gga act act tca gaa tgg act tta cca          3294
Tyr His Trp Asn Pro Leu Gly Thr Thr Ser Glu Trp Thr Leu Pro
1085                1090                1095
```

| | | |
|---|---|---|
| gaa gga tgg act tct aat gac aaa gtt tat tta tat gaa tta tca<br>Glu Gly Trp Thr Ser Asn Asp Lys Val Tyr Leu Tyr Glu Leu Ser<br>1100                        1105                      1110 | 3339 |
| gat tta gga aga act tta gtt aag gaa gta cca gtt gta gat gga<br>Asp Leu Gly Arg Thr Leu Val Lys Glu Val Pro Val Val Asp Gly<br>1115                        1120                      1125 | 3384 |
| aaa gtt aat tta gaa gta aaa caa gat act cct tat ata gtt act<br>Lys Val Asn Leu Glu Val Lys Gln Asp Thr Pro Tyr Ile Val Thr<br>1130                        1135                      1140 | 3429 |
| aag gaa aaa gtt gaa gag aag aga ata gag gat tgg gga tat ggc<br>Lys Glu Lys Val Glu Glu Lys Arg Ile Glu Asp Trp Gly Tyr Gly<br>1145                        1150                      1155 | 3474 |
| tca gaa ata gct gat cca gga ttt gat tct caa act ttt gat aag<br>Ser Glu Ile Ala Asp Pro Gly Phe Asp Ser Gln Thr Phe Asp Lys<br>1160                        1165                      1170 | 3519 |
| tgg aat aaa gaa tct act gct gaa aat aca gat cat ata act att<br>Trp Asn Lys Glu Ser Thr Ala Glu Asn Thr Asp His Ile Thr Ile<br>1175                        1180                      1185 | 3564 |
| gaa aat gaa agt gtt caa aag aga tta ggt aat gat gtt ctt aaa<br>Glu Asn Glu Ser Val Gln Lys Arg Leu Gly Asn Asp Val Leu Lys<br>1190                        1195                      1200 | 3609 |
| ata agt gga aat gaa ggc gct gat gct aaa att tct caa agc ata<br>Ile Ser Gly Asn Glu Gly Ala Asp Ala Lys Ile Ser Gln Ser Ile<br>1205                        1210                      1215 | 3654 |
| agt gga tta gaa gaa gga gta act tat tca gta tct gca tgg gtt<br>Ser Gly Leu Glu Glu Gly Val Thr Tyr Ser Val Ser Ala Trp Val<br>1220                        1225                      1230 | 3699 |
| aaa aat gat aat aat aga gaa gtt aca cta gga gtt aat gtt ggt<br>Lys Asn Asp Asn Asn Arg Glu Val Thr Leu Gly Val Asn Val Gly<br>1235                        1240                      1245 | 3744 |
| gga aaa gat ttc act aat gta ata aca agt ggt ggt aaa gta aga<br>Gly Lys Asp Phe Thr Asn Val Ile Thr Ser Gly Gly Lys Val Arg<br>1250                        1255                      1260 | 3789 |
| caa gga gaa ggt gtt aag tat att gac gat act ttc gtg aga atg<br>Gln Gly Glu Gly Val Lys Tyr Ile Asp Asp Thr Phe Val Arg Met<br>1265                        1270                      1275 | 3834 |
| gaa gta gaa ttt act gta cct aaa gga gta aat tca gct gat gtt<br>Glu Val Glu Phe Thr Val Pro Lys Gly Val Asn Ser Ala Asp Val<br>1280                        1285                      1290 | 3879 |
| tac tta aag gct tca gaa gga gat gct gac tca gtt gta cta gtt<br>Tyr Leu Lys Ala Ser Glu Gly Asp Ala Asp Ser Val Val Leu Val<br>1295                        1300                      1305 | 3924 |
| gat gac ttt aga ata tgg gat cat cca gga cac act aat aga gat<br>Asp Asp Phe Arg Ile Trp Asp His Pro Gly His Thr Asn Arg Asp<br>1310                        1315                      1320 | 3969 |
| gga tat gta ttc tac gaa gat ttt gaa aat gta gat gaa ggt ata<br>Gly Tyr Val Phe Tyr Glu Asp Phe Glu Asn Val Asp Glu Gly Ile<br>1325                        1330                      1335 | 4014 |
| tca cca ttt tat tta tct cca gga aga gga cat tca aat aga tct<br>Ser Pro Phe Tyr Leu Ser Pro Gly Arg Gly His Ser Asn Arg Ser<br>1340                        1345                      1350 | 4059 |
| cac tta gct gag aag gat ata tct ata gat gct aat caa aga atg<br>His Leu Ala Glu Lys Asp Ile Ser Ile Asp Ala Asn Gln Arg Met<br>1355                        1360                      1365 | 4104 |
| aac tgg gta ctt gat gga aga ttc tca tta aaa tct aac caa caa<br>Asn Trp Val Leu Asp Gly Arg Phe Ser Leu Lys Ser Asn Gln Gln<br>1370                        1375                      1380 | 4149 |
| cca aag gaa ata ggt gaa atg ttg act acg gat gtt tca tca ttc<br>Pro Lys Glu Ile Gly Glu Met Leu Thr Thr Asp Val Ser Ser Phe | 4194 |

-continued

|     |     |     |     | 1385 |     |     |     |     | 1390 |     |     |     |     | 1395 |     |      |
|-----|-----|-----|-----|------|-----|-----|-----|-----|------|-----|-----|-----|-----|------|-----|------|
| aaa | tta | gaa | cca | aat  | aaa | act | tat | gaa | ttt  | gga | ttc | tta | tat | tca  |     | 4239 |
| Lys | Leu | Glu | Pro | Asn  | Lys | Thr | Tyr | Glu | Phe  | Gly | Phe | Leu | Tyr | Ser  |     |      |
|     | 1400|     |     |      | 1405|     |     |     |      | 1410|     |     |     |      |     |      |

| tta | gaa | aat | gct | gct | cca | gga | tat | tct | gta | aat | att | aag | aat | aga | 4284 |
|-----|-----|-----|-----|-----|-----|-----|-----|-----|-----|-----|-----|-----|-----|-----|------|
| Leu | Glu | Asn | Ala | Ala | Pro | Gly | Tyr | Ser | Val | Asn | Ile | Lys | Asn | Arg |      |
|     | 1415|     |     |     |     | 1420|     |     |     |     | 1425|     |     |     |      |

| gat | ggt | gaa | aag | att | gta | agt | att | cct | tta | gag | gct | act | ggt | tca | 4329 |
| Asp | Gly | Glu | Lys | Ile | Val | Ser | Ile | Pro | Leu | Glu | Ala | Thr | Gly | Ser |      |
|     | 1430|     |     |     |     | 1435|     |     |     |     | 1440|     |     |     |      |

| aat | tat | gca | caa | gat | att | ttc | act | aaa | act | aaa | tct | gta | act | cac | 4374 |
| Asn | Tyr | Ala | Gln | Asp | Ile | Phe | Thr | Lys | Thr | Lys | Ser | Val | Thr | His |      |
|     | 1445|     |     |     |     | 1450|     |     |     |     | 1455|     |     |     |      |

| gag | ttt | aca | act | gga | gat | ttt | gct | gga | gat | tac | tat | att | act | tta | 4419 |
| Glu | Phe | Thr | Thr | Gly | Asp | Phe | Ala | Gly | Asp | Tyr | Tyr | Ile | Thr | Leu |      |
|     | 1460|     |     |     |     | 1465|     |     |     |     | 1470|     |     |     |      |

| gaa | aaa | ggt | gat | gga | ttt | aaa | gaa | gta | atc | tta | gat | aat | att | tat | 4464 |
| Glu | Lys | Gly | Asp | Gly | Phe | Lys | Glu | Val | Ile | Leu | Asp | Asn | Ile | Tyr |      |
|     | 1475|     |     |     |     | 1480|     |     |     |     | 1485|     |     |     |      |

| gtt | aag | gaa | ata | gat | aag | tca | att | gaa | tca | cct | gaa | tta | gct | cat | 4509 |
| Val | Lys | Glu | Ile | Asp | Lys | Ser | Ile | Glu | Ser | Pro | Glu | Leu | Ala | His |      |
|     | 1490|     |     |     |     | 1495|     |     |     |     | 1500|     |     |     |      |

| gta | aac | tta | aat | aca | gta | gaa | cat | gac | tta | gaa | gtt | gga | caa | agc | 4554 |
| Val | Asn | Leu | Asn | Thr | Val | Glu | His | Asp | Leu | Glu | Val | Gly | Gln | Ser |      |
|     | 1505|     |     |     |     | 1510|     |     |     |     | 1515|     |     |     |      |

| gtt | cca | ttt | gct | ata | aat | gca | tta | atg | aat | aat | ggt | gca | aat | gtt | 4599 |
| Val | Pro | Phe | Ala | Ile | Asn | Ala | Leu | Met | Asn | Asn | Gly | Ala | Asn | Val |      |
|     | 1520|     |     |     |     | 1525|     |     |     |     | 1530|     |     |     |      |

| aac | tta | gaa | gaa | gct | gaa | gtt | gaa | tat | aaa | gtt | tca | aaa | cca | gaa | 4644 |
| Asn | Leu | Glu | Glu | Ala | Glu | Val | Glu | Tyr | Lys | Val | Ser | Lys | Pro | Glu |      |
|     | 1535|     |     |     |     | 1540|     |     |     |     | 1545|     |     |     |      |

| gtt | tta | act | att | gaa | aat | gga | atg | atg | act | gga | gct | tct | gaa | ggc | 4689 |
| Val | Leu | Thr | Ile | Glu | Asn | Gly | Met | Met | Thr | Gly | Ala | Ser | Glu | Gly |      |
|     | 1550|     |     |     |     | 1555|     |     |     |     | 1560|     |     |     |      |

| ttt | act | gat | gtc | caa | gta | aat | att | act | gtt | aat | gga | aat | aaa | gtt | 4734 |
| Phe | Thr | Asp | Val | Gln | Val | Asn | Ile | Thr | Val | Asn | Gly | Asn | Lys | Val |      |
|     | 1565|     |     |     |     | 1570|     |     |     |     | 1575|     |     |     |      |

| tct | tca | aat | aca | gta | aga | gtt | aag | gtt | gga | aat | cca | gaa | gtt | gag | 4779 |
| Ser | Ser | Asn | Thr | Val | Arg | Val | Lys | Val | Gly | Asn | Pro | Glu | Val | Glu |      |
|     | 1580|     |     |     |     | 1585|     |     |     |     | 1590|     |     |     |      |

| gaa | gaa | gaa | gtt | ata | gta | aac | cca | gta | aga | aac | ttt | aag | gtt | act | 4824 |
| Glu | Glu | Glu | Val | Ile | Val | Asn | Pro | Val | Arg | Asn | Phe | Lys | Val | Thr |      |
|     | 1595|     |     |     |     | 1600|     |     |     |     | 1605|     |     |     |      |

| gat | aag | act | aag | aag | aat | gta | act | gta | agc | tgg | gaa | gag | cca | gaa | 4869 |
| Asp | Lys | Thr | Lys | Lys | Asn | Val | Thr | Val | Ser | Trp | Glu | Glu | Pro | Glu |      |
|     | 1610|     |     |     |     | 1615|     |     |     |     | 1620|     |     |     |      |

| aaa | act | tat | gga | tta | gaa | ggc | tat | gtt | ctt | tat | aaa | gat | ggt | aag | 4914 |
| Lys | Thr | Tyr | Gly | Leu | Glu | Gly | Tyr | Val | Leu | Tyr | Lys | Asp | Gly | Lys |      |
|     | 1625|     |     |     |     | 1630|     |     |     |     | 1635|     |     |     |      |

| aaa | gtt | aaa | gaa | ata | ggt | gct | gat | aaa | act | gaa | ttt | aca | ttt | aag | 4959 |
| Lys | Val | Lys | Glu | Ile | Gly | Ala | Asp | Lys | Thr | Glu | Phe | Thr | Phe | Lys |      |
|     | 1640|     |     |     |     | 1645|     |     |     |     | 1650|     |     |     |      |

| gga | tta | aac | aga | cac | act | att | tat | aac | ttt | aag | att | gct | gct | aaa | 5004 |
| Gly | Leu | Asn | Arg | His | Thr | Ile | Tyr | Asn | Phe | Lys | Ile | Ala | Ala | Lys |      |
|     | 1655|     |     |     |     | 1660|     |     |     |     | 1665|     |     |     |      |

| tat | tct | aat | ggt | gaa | ctt | tca | act | aag | gaa | tca | ata | act | gtt | aga | 5049 |
| Tyr | Ser | Asn | Gly | Glu | Leu | Ser | Thr | Lys | Glu | Ser | Ile | Thr | Val | Arg |      |
|     | 1670|     |     |     |     | 1675|     |     |     |     | 1680|     |     |     |      |

| act | gca | aga | taa |     |     |     |     |     |     |     |     |     |     |     | 5061 |

-continued

```
Thr Ala  Arg
    1685

<210> SEQ ID NO 8
<211> LENGTH: 1686
<212> TYPE: PRT
<213> ORGANISM: Clostridium perfringens str. 13

<400> SEQUENCE: 8

Met Gly Arg Lys Cys Met Asn Lys Lys Ile Ala Ala Ile Ile Ala Ala
1               5                   10                  15

Ala Val Ile Val Gly Gln Leu Pro Ile Ser Val Leu Ala Thr Pro Val
            20                  25                  30

Asn Glu Ala Gly Asp Glu Ile Asn Ser Glu Ser Ala Glu Ile Leu Thr
        35                  40                  45

Asn Ser Asp Glu Glu Ala Glu Ala Tyr Ile Gln Asn Tyr Asp Arg Pro
    50                  55                  60

Glu Gly Ile Thr Trp Thr Lys Leu Ala Gly Ser Gly Ser Val Glu Val
65                  70                  75                  80

Thr Asp Gly Phe Leu Ser Val Thr Asn Asn Gly Asp Tyr Arg Ile Met
                85                  90                  95

Glu Asp Gln Ser Pro Asn Ile Lys Asn Gly Glu Leu Glu Ser Lys Phe
            100                 105                 110

Thr Val Gly Gly Ser Gln Thr Gly Ile Ile Phe Arg Ala Thr Glu Ser
        115                 120                 125

Asn Tyr Gly Met Ile Asn Tyr Asn Ser Gly Thr Gly Trp Val Ile Glu
    130                 135                 140

Asn Lys Asn Ser Trp Glu Asp Ile Thr Gly Pro Lys Leu Asn Asn Gly
145                 150                 155                 160

Asp Val Val Thr Val Lys Ala Thr Phe Val Glu Lys His Leu Thr Val
                165                 170                 175

Asn Val Ser Val Asn Asp Gly Glu Phe Glu Thr Ile Tyr Asp Lys Glu
            180                 185                 190

Ser Asp Leu Ile Pro Leu Gln Ala Gly Lys Val Gly Tyr Arg Gly Trp
        195                 200                 205

Gly Asn Ala Lys Thr Thr Lys Phe Asp Tyr Ile Lys Tyr Ala Pro Met
    210                 215                 220

Thr Ile Asp Lys Gly Pro Ile Val Ser Ile Asn Glu Val Asn Val Glu
225                 230                 235                 240

Thr Tyr Pro Arg Val Lys Pro Ile Leu Pro Ser Ser Val Thr Val Asn
                245                 250                 255

His Glu Asn Gly Met Ser Ser Ile Lys Asp Val Ser Trp Asn Tyr Ile
            260                 265                 270

Pro Lys Glu Ser Tyr Ser Lys Pro Gly Thr Phe Lys Val Glu Gly Thr
        275                 280                 285

Val Glu Gly Thr Asp Val Lys Ala Ile Ala Asn Val Thr Val Ser Ser
    290                 295                 300

Asp Leu Ala Tyr Tyr Glu Thr Asn Phe Glu Thr Glu Glu Thr Arg Gly
305                 310                 315                 320

Asp Trp Gln Val Val Gln Gly Gly Gly Ser Pro Ser Tyr Glu Glu Gly
                325                 330                 335

Lys Val Lys Ile Pro Met Asn Gly Val Ser Ile Ala Val Asp Met Asn
            340                 345                 350

Ser Pro Glu Val Lys Asn Phe Thr Tyr Glu Thr Asp Phe Ser Val Asp
        355                 360                 365
```

-continued

Asn Asn Gly Gly Arg Ile Gly Leu Leu Phe Arg Tyr Val Ser Glu Thr
    370                 375                 380

Glu Trp Gly Ala Val Cys Tyr Asp Asn Gly Ser Trp Val Trp Lys Thr
385                 390                 395                 400

Gly Asp Gly Lys Tyr Gly Asn Phe Pro Gly Thr Phe Thr Pro Glu Pro
                405                 410                 415

Gly Lys Thr Tyr Arg Ile Lys Leu Lys Val Glu Asp Thr Asn Ile Thr
                420                 425                 430

Met Trp Val Asp Gly Glu Lys Ile Gly Gln Val Ala Val Ser Asn Leu
        435                 440                 445

Pro Asp Val Arg Gly Lys Val Gly Leu Thr Gly Trp Phe Gly Asn Lys
    450                 455                 460

Asn Val Thr Leu Asp Asn Leu Val Val Glu Glu Leu Gly Gly Ile Met
465                 470                 475                 480

Ala Pro Glu Val Gly Pro Leu Glu Glu Gln Ser Ile Glu Ser Asp Ser
                485                 490                 495

Met Lys Val Val Leu Asp Asn Arg Phe Pro Thr Val Ile Arg Tyr Glu
                500                 505                 510

Trp Lys Gly Thr Glu Asp Val Leu Ser Gly Ala Ser Val Asp Asp Leu
        515                 520                 525

Glu Ala Gln Tyr Met Val Glu Ile Asn Gly Glu Lys Arg Ile Pro Lys
    530                 535                 540

Val Thr Ser Glu Phe Ala Asn Asn Glu Gly Ile Tyr Thr Leu Asn Phe
545                 550                 555                 560

Glu Asp Ile Gly Met Thr Ile Thr Leu Lys Met Thr Val Asn Glu Asn
                565                 570                 575

Lys Leu Arg Met Glu Val Thr Asp Ile Gln Glu Gly Asp Val Lys Leu
                580                 585                 590

Gln Thr Leu Asn Phe Pro Asn His Ser Leu Ala Ser Val Ser Ser Leu
        595                 600                 605

Asn Asn Gly Lys Thr Ala Ser Val Leu Thr Thr Gly Asp Trp Asn Asn
    610                 615                 620

Ile Asn Glu Glu Phe Thr Asp Val Ala Lys Ala Lys Pro Gly Val Lys
625                 630                 635                 640

Gly Lys Thr Tyr Ala Phe Ile Asn Asp Lys Phe Ala Val Thr Ile
                645                 650                 655

Asn Asn Asn Thr Ile Glu Gly Gly Asn Arg Val Val Leu Thr Thr Glu
                660                 665                 670

Asn Asp Thr Leu Pro Asp Asn Thr Asn Tyr Lys Lys Val Gly Ile Ser
        675                 680                 685

Asn Gly Thr Trp Thr Tyr Lys Glu Ile Leu Gln Asp Thr Thr Asp Gln
    690                 695                 700

Gly Ser Lys Leu Tyr Gln Gly Glu Lys Pro Trp Ser Glu Val Ile Ile
705                 710                 715                 720

Ala Arg Asp Glu Asn Glu Asp Gly Gln Val Asp Trp Gln Asp Gly Ala
                725                 730                 735

Ile Gln Tyr Arg Lys Asn Met Lys Ile Pro Val Gly Gly Glu Glu Ile
                740                 745                 750

Lys Asn Gln Met Ser Tyr Ile Asp Phe Asn Ile Gly Tyr Thr Gln Asn
        755                 760                 765

Pro Phe Leu Arg Ser Leu Asp Thr Ile Lys Lys Leu Ser Asn Tyr Thr
    770                 775                 780

```
Asp Gly Phe Gly Gln Leu Val Leu His Lys Gly Tyr Gln Gly Glu Gly
785                 790                 795                 800

His Asp Asp Ser His Pro Asp Tyr Gly Gly His Ile Gly Met Arg Gln
                805                 810                 815

Gly Gly Lys Glu Asp Phe Asn Thr Leu Ile Glu Gln Gly Lys Glu Tyr
            820                 825                 830

Asn Ala Lys Ile Gly Val His Ile Asn Ala Thr Glu Tyr Thr Met Asp
                835                 840                 845

Ala Phe Glu Tyr Pro Thr Glu Leu Val Asn Glu Asn Ala Pro Gly Trp
850                 855                 860

Gly Trp Leu Asp Gln Ala Tyr Tyr Val Asn Gln Arg Gly Asp Ile Thr
865                 870                 875                 880

Ser Gly Glu Leu Phe Arg Arg Leu Asp Met Leu Met Glu Asp Ala Pro
                885                 890                 895

Glu Leu Gly Trp Ile Tyr Val Asp Val Tyr Thr Gly Asn Gly Trp Asn
                900                 905                 910

Ala His Gln Leu Gly Glu Lys Ile Asn Asp Tyr Gly Ile Met Ile Ala
            915                 920                 925

Thr Glu Met Asn Gly Pro Leu Glu Gln His Val Pro Trp Thr His Trp
        930                 935                 940

Gly Gly Asp Pro Ala Tyr Pro Asn Lys Gly Asn Ala Ser Lys Ile Met
945                 950                 955                 960

Arg Phe Met Lys Asn Asp Thr Gln Asp Ser Phe Leu Ala Asp Pro Leu
                965                 970                 975

Val Lys Gly Asn Lys His Leu Leu Ser Gly Gly Trp Gly Thr Arg His
                980                 985                 990

Asp Ile Glu Gly Ala Tyr Gly Thr  Glu Val Phe Tyr Asn  Gln Val Leu
            995                 1000                1005

Pro Thr  Lys Tyr Leu Gln His  Phe Gln Ile Thr Lys  Met Ser Glu
    1010                1015                1020

Asn Glu  Val Leu Phe Glu Asn  Gly Val Lys Ala Val  Arg Glu Asn
    1025                1030                1035

Ser Asn  Ile Asn Tyr Tyr Arg  Asn Asp Arg Leu Val  Ala Thr Thr
    1040                1045                1050

Pro Glu  Asn Ser Ile Gly Asn  Thr Gly Ile Gly Asp  Thr Gln Leu
    1055                1060                1065

Phe Leu  Pro Trp Asn Pro Val  Asp Glu Ala Asn Ser  Glu Lys Ile
    1070                1075                1080

Tyr His  Trp Asn Pro Leu Gly  Thr Thr Ser Glu Trp  Thr Leu Pro
    1085                1090                1095

Glu Gly  Trp Thr Ser Asn Asp  Lys Val Tyr Leu Tyr  Glu Leu Ser
    1100                1105                1110

Asp Leu  Gly Arg Thr Leu Val  Lys Glu Val Pro Val  Val Asp Gly
    1115                1120                1125

Lys Val  Asn Leu Glu Val Lys  Gln Asp Thr Pro Tyr  Ile Val Thr
    1130                1135                1140

Lys Glu  Lys Val Glu Glu Lys  Arg Ile Glu Asp Trp  Gly Tyr Gly
    1145                1150                1155

Ser Glu  Ile Ala Asp Pro Gly  Phe Asp Ser Gln Thr  Phe Asp Lys
    1160                1165                1170

Trp Asn  Lys Glu Ser Thr Ala  Glu Asn Thr Asp His  Ile Thr Ile
    1175                1180                1185

Glu Asn  Glu Ser Val Gln Lys  Arg Leu Gly Asn Asp  Val Leu Lys
```

-continued

```
             1190                1195                1200
Ile Ser  Gly Asn Glu Gly  Ala Asp Ala Lys  Ile Ser Gln Ser  Ile
    1205                1210                1215

Ser Gly  Leu Glu Glu Gly  Val Thr Tyr Ser  Val Ser Ala Trp  Val
    1220                1225                1230

Lys Asn  Asp Asn Asn Arg  Glu Val Thr Leu  Gly Val Asn Val  Gly
    1235                1240                1245

Gly Lys  Asp Phe Thr Asn  Val Ile Thr Ser  Gly Lys Val Arg
    1250                1255                1260

Gln Gly  Glu Gly Val Lys  Tyr Ile Asp Asp  Thr Phe Val Arg  Met
    1265                1270                1275

Glu Val  Glu Phe Thr Val  Pro Lys Gly Val  Asn Ser Ala Asp  Val
    1280                1285                1290

Tyr Leu  Lys Ala Ser Glu  Gly Asp Ala Asp  Ser Val Val Leu  Val
    1295                1300                1305

Asp Asp  Phe Arg Ile Trp  Asp His Pro Gly  His Thr Asn Arg  Asp
    1310                1315                1320

Gly Tyr  Val Phe Tyr Glu  Asp Phe Glu Asn  Val Asp Glu Gly  Ile
    1325                1330                1335

Ser Pro  Phe Tyr Leu Ser  Pro Gly Arg Gly  His Ser Asn Arg  Ser
    1340                1345                1350

His Leu  Ala Glu Lys Asp  Ile Ser Ile Asp  Ala Asn Gln Arg  Met
    1355                1360                1365

Asn Trp  Val Leu Asp Gly  Arg Phe Ser Leu  Lys Ser Asn Gln  Gln
    1370                1375                1380

Pro Lys  Glu Ile Gly Glu  Met Leu Thr Thr  Asp Val Ser Ser  Phe
    1385                1390                1395

Lys Leu  Glu Pro Asn Lys  Thr Tyr Glu Phe  Gly Phe Leu Tyr  Ser
    1400                1405                1410

Leu Glu  Asn Ala Ala Pro  Gly Tyr Ser Val  Asn Ile Lys Asn  Arg
    1415                1420                1425

Asp Gly  Glu Lys Ile Val  Ser Ile Pro Leu  Glu Ala Thr Gly  Ser
    1430                1435                1440

Asn Tyr  Ala Gln Asp Ile  Phe Thr Lys Thr  Lys Ser Val Thr  His
    1445                1450                1455

Glu Phe  Thr Thr Gly Asp  Phe Ala Gly Asp  Tyr Tyr Ile Thr  Leu
    1460                1465                1470

Glu Lys  Gly Asp Gly Phe  Lys Glu Val Ile  Leu Asp Asn Ile  Tyr
    1475                1480                1485

Val Lys  Glu Ile Asp Lys  Ser Ile Glu Ser  Pro Glu Leu Ala  His
    1490                1495                1500

Val Asn  Leu Asn Thr Val  Glu His Asp Leu  Glu Val Gly Gln  Ser
    1505                1510                1515

Val Pro  Phe Ala Ile Asn  Ala Leu Met Asn  Asn Gly Ala Asn  Val
    1520                1525                1530

Asn Leu  Glu Glu Ala Glu  Val Glu Tyr Lys  Val Ser Lys Pro  Glu
    1535                1540                1545

Val Leu  Thr Ile Glu Asn  Gly Met Met Thr  Gly Ala Ser Glu  Gly
    1550                1555                1560

Phe Thr  Asp Val Gln Val  Asn Ile Thr Val  Asn Gly Asn Lys  Val
    1565                1570                1575

Ser Ser  Asn Thr Val Arg  Val Lys Val Gly  Asn Pro Glu Val  Glu
    1580                1585                1590
```

-continued

```
Glu Glu Glu Val Ile Val Asn Pro Val Arg Asn Phe Lys Val Thr
    1595                1600                1605

Asp Lys Thr Lys Lys Asn Val Thr Val Ser Trp Glu Glu Pro Glu
    1610                1615                1620

Lys Thr Tyr Gly Leu Glu Gly Tyr Val Leu Tyr Lys Asp Gly Lys
    1625                1630                1635

Lys Val Lys Glu Ile Gly Ala Asp Lys Thr Glu Phe Thr Phe Lys
    1640                1645                1650

Gly Leu Asn Arg His Thr Ile Tyr Asn Phe Lys Ile Ala Ala Lys
    1655                1660                1665

Tyr Ser Asn Gly Glu Leu Ser Thr Lys Glu Ser Ile Thr Val Arg
    1670                1675                1680

Thr Ala Arg
    1685

<210> SEQ ID NO 9
<211> LENGTH: 4086
<212> TYPE: DNA
<213> ORGANISM: Streptomyces coelicolor A3(2)
<220> FEATURE:
<221> NAME/KEY: CDS
<222> LOCATION: (1)..(4086)

<400> SEQUENCE: 9
```

| | | |
|---|---|---|
| atg gca gcg atc aca ccg aag cga tcg gtc aga gtg gac acc tcg aca<br>Met Ala Ala Ile Thr Pro Lys Arg Ser Val Arg Val Asp Thr Ser Thr<br>1               5                   10                  15 | 48 |
| ggc tca tca tct ccc cca acc gga cgc gca cgg gtc cgg cgg cac ggc<br>Gly Ser Ser Ser Pro Pro Thr Gly Arg Ala Arg Val Arg Arg His Gly<br>            20                  25                  30 | 96 |
| gcc gtc gtc gcg gcg ctg ggc ctc acc gcg ggc ctg ctg tcg gcc gcc<br>Ala Val Val Ala Ala Leu Gly Leu Thr Ala Gly Leu Leu Ser Ala Ala<br>        35                  40                  45 | 144 |
| gcc ctg ccc gcg ggc gcg gcc ccg ccc cgc ccc gct gcc gct gcg gcg<br>Ala Leu Pro Ala Gly Ala Ala Pro Pro Arg Pro Ala Ala Ala Ala Ala<br>    50                  55                  60 | 192 |
| ccc gcg ggg gca ccg acg ccg gtg gaa ctg agc cgg ggc ggg ctg acc<br>Pro Ala Gly Ala Pro Thr Pro Val Glu Leu Ser Arg Gly Gly Leu Thr<br>65                  70                  75                  80 | 240 |
| gtc acc gtg gcg aag gag ttc ccc cag gtg atc tcc tac cgg ctg ggc<br>Val Thr Val Ala Lys Glu Phe Pro Gln Val Ile Ser Tyr Arg Leu Gly<br>                85                  90                  95 | 288 |
| cgg cgc gga ctc gac ggg cgg gca acg gcg ctg gac ggc ttc acc gtc<br>Arg Arg Gly Leu Asp Gly Arg Ala Thr Ala Leu Asp Gly Phe Thr Val<br>            100                 105                 110 | 336 |
| aac ggc gag agc cac cgc gcc acc acc acc gtg aag gcg aag ggc agc<br>Asn Gly Glu Ser His Arg Ala Thr Thr Thr Val Lys Ala Lys Gly Ser<br>        115                 120                 125 | 384 |
| agg gcg gtc tac acc tcc acg ttc gag gac ctg ccc ggt ctc acg atc<br>Arg Ala Val Tyr Thr Ser Thr Phe Glu Asp Leu Pro Gly Leu Thr Ile<br>    130                 135                 140 | 432 |
| acc tcc agc atc acg gtc acc aag gag acg acg gtc gtc ttc gcc gtc<br>Thr Ser Ser Ile Thr Val Thr Lys Glu Thr Thr Val Val Phe Ala Val<br>145                 150                 155                 160 | 480 |
| gag aag atc tcg ggc gag gcc gcg ccg ggc gtg cgc acc ctc gcg atc<br>Glu Lys Ile Ser Gly Glu Ala Ala Pro Gly Val Arg Thr Leu Ala Ile<br>                165                 170                 175 | 528 |
| ccc ggc cag tcc ctc gtc tcc gtc gac tcc gcc gag ccg ggc gcc aac<br>Pro Gly Gln Ser Leu Val Ser Val Asp Ser Ala Glu Pro Gly Ala Asn | 576 |

-continued

```
                180                 185                 190
ctc gcc cgg acg aag atc tcc acc gac tcg acg acg gcc gac cgc       624
Leu Ala Arg Thr Lys Ile Ser Thr Asp Ser Thr Thr Ala Asp Arg
        195                 200                 205 ttc gtc ccc gtc acc ggc gac acc gcc ccg gac aag ggg ccc gtc ggc   672
Phe Val Pro Val Thr Gly Asp Thr Ala Pro Asp Lys Gly Pro Val Gly
210                 215                 220 acc ccg tac gcg ttc gtc ggc aac gcg cag ttg tcg gcg ggc atc atc   720
Thr Pro Tyr Ala Phe Val Gly Asn Ala Gln Leu Ser Ala Gly Ile Ile
225                 230                 235                 240 acc aac gcg acc gag gac tcg ccg cag gac gac aac acc gac tgg aac   768
Thr Asn Ala Thr Glu Asp Ser Pro Gln Asp Asp Asn Thr Asp Trp Asn
                245                 250                 255 acc cgc ctg cag tcc cgc atc gtc gac gag ggc gag gga cgc gcc cgg   816
Thr Arg Leu Gln Ser Arg Ile Val Asp Glu Gly Glu Gly Arg Arg Arg
            260                 265                 270 gcg gag ctg tcg gcc ggc acg tac acc tac cac ccc gag ggc gcc acc   864
Ala Glu Leu Ser Ala Gly Thr Tyr Thr Tyr His Pro Glu Gly Ala Thr
        275                 280                 285 gat cca cgg gtc gac acc tac gag ctg ccc cgg gcg acg gtg gtc ctc   912
Asp Pro Arg Val Asp Thr Tyr Glu Leu Pro Arg Ala Thr Val Val Leu
290                 295                 300 gcc gcc gac gcc aac cgg gac ggc acg gtc gac tgg cag gac ggc gcc   960
Ala Ala Asp Ala Asn Arg Asp Gly Thr Val Asp Trp Gln Asp Gly Ala
305                 310                 315                 320 atc gcc cac cgg gag cac atg cgc cgc ccg ctc ggc gcc gac cgg gtg   1008
Ile Ala His Arg Glu His Met Arg Arg Pro Leu Gly Ala Asp Arg Val
                325                 330                 335 ccc gaa cgc gtg gtc cag cgc atc ccg ttc aac ttc gcg agc cag gcc   1056
Pro Glu Arg Val Val Gln Arg Ile Pro Phe Asn Phe Ala Ser Gln Ala
            340                 345                 350 acc aac ccg ttc ctg aag acg ctg gac aac acc aag cgc atc tcc atg   1104
Thr Asn Pro Phe Leu Lys Thr Leu Asp Asn Thr Lys Arg Ile Ser Met
        355                 360                 365 gcc acc gac gac ctc ggg cag tgg gtg ctg gag aag ggg tac gcg agc   1152
Ala Thr Asp Asp Leu Gly Gln Trp Val Leu Glu Lys Gly Tyr Ala Ser
370                 375                 380 gag ggc cac gac tcc gcc cac ccc gac tac ggc ggc aac gag aac gtc   1200
Glu Gly His Asp Ser Ala His Pro Asp Tyr Gly Gly Asn Glu Asn Val
385                 390                 395                 400 cgc gcg ggc ggc tgg aag gac ctg aac cgc ctc acc cgg acg gga gcc   1248
Arg Ala Gly Gly Trp Lys Asp Leu Asn Arg Leu Thr Arg Thr Gly Ala
                405                 410                 415 ggc tac aac gcg gac ttc gcc gtc cac gtc aac gcc acg gag gcc tac   1296
Gly Tyr Asn Ala Asp Phe Ala Val His Val Asn Ala Thr Glu Ala Tyr
            420                 425                 430 gcc cag gcc agg acc ttc acc gag gac atg gtc gcg ggc cag gcc gac   1344
Ala Gln Ala Arg Thr Phe Thr Glu Asp Met Val Ala Gly Gln Ala Asp
        435                 440                 445 ggc tgg gac tgg ctc aac cag gcc tac cac atc gac cag cgc aag gac   1392
Gly Trp Asp Trp Leu Asn Gln Ala Tyr His Ile Asp Gln Arg Lys Asp
450                 455                 460 ctg ggc acc ggc gcc gtc ctc gac cgc ttc aag cag ctc cgc aag gaa   1440
Leu Gly Thr Gly Ala Val Leu Asp Arg Phe Lys Gln Leu Arg Lys Glu
465                 470                 475                 480 gca ccg ggc atc aga acc gtc tac atc gac gcc tac tac tcc agc ggc   1488
Ala Pro Gly Ile Arg Thr Val Tyr Ile Asp Ala Tyr Tyr Ser Ser Gly
                485                 490                 495 tgg ctg gcc gac ggt ctg gcc gcc ggg ctg cgt gag atg ggc ttc gag   1536
```

```
                Trp Leu Ala Asp Gly Leu Ala Ala Gly Leu Arg Glu Met Gly Phe Glu
                            500                 505                 510 gtc gcc acc gag tgg gcg tac aag ttc gag ggc acc tcg gtg tgg tcg         1584
Val Ala Thr Glu Trp Ala Tyr Lys Phe Glu Gly Thr Ser Val Trp Ser
            515                 520                 525 cac tgg gcg gcc gac aag aac tac ggc ggc gcc acg aac aag ggc atc         1632
His Trp Ala Ala Asp Lys Asn Tyr Gly Gly Ala Thr Asn Lys Gly Ile
            530                 535                 540 aac tcg gac atc gtc cgg ttc atc gcc aac gcc gac cgc gac gtg tgg         1680
Asn Ser Asp Ile Val Arg Phe Ile Ala Asn Ala Asp Arg Asp Val Trp
545                 550                 555                 560 aac gtg gac ccg ctc ctc ggc ggc gcg agc gtc gtc gag ttc gag ggc         1728
Asn Val Asp Pro Leu Leu Gly Gly Ala Ser Val Val Glu Phe Glu Gly
                565                 570                 575 tgg acc ggc cag gac gac tgg aac gcc ttc tac cgc aac atc tgg acc         1776
Trp Thr Gly Gln Asp Asp Trp Asn Ala Phe Tyr Arg Asn Ile Trp Thr
            580                 585                 590 gac aac ctg ccg acc aag ttc ctc cag cac ttc cag gtg ctg gac tgg         1824
Asp Asn Leu Pro Thr Lys Phe Leu Gln His Phe Gln Val Leu Asp Trp
            595                 600                 605 gac cgc ggc agg tcc gcg agg ctc acc ggc ggg gtg gac gtg aag tcc         1872
Asp Arg Gly Arg Ser Ala Arg Leu Thr Gly Gly Val Asp Val Lys Ser
610                 615                 620 gtc gac ggc gag cgg cgg atc tcc atg gac ggc acc gag gtc ctc aag         1920
Val Asp Gly Glu Arg Arg Ile Ser Met Asp Gly Thr Glu Val Leu Lys
625                 630                 635                 640 ggc gac acc tac ctg ctg ccc tgg cag aac gcc ggg aag gac gac ggc         1968
Gly Asp Thr Tyr Leu Leu Pro Trp Gln Asn Ala Gly Lys Asp Asp Gly
                645                 650                 655 acc tcg tcg ccc cgc gac gcc gac aag atg tac ttc tac agc gcc tcc         2016
Thr Ser Ser Pro Arg Asp Ala Asp Lys Met Tyr Phe Tyr Ser Ala Ser
                660                 665                 670 ggc ggc gag cac acc ttc gaa ctg acc gga cag ttc gcg ggc acc gag         2064
Gly Gly Glu His Thr Phe Glu Leu Thr Gly Gln Phe Ala Gly Thr Glu
            675                 680                 685 gac ttc acc ctc tac gaa ctc acc gac cag ggc cgg gcg gag aag gcc         2112
Asp Phe Thr Leu Tyr Glu Leu Thr Asp Gln Gly Arg Ala Glu Lys Ala
            690                 695                 700 cgg gtg acg gcc cac gag ggg cgg gtg acc ctc acc gcc gag aag ggg         2160
Arg Val Thr Ala His Glu Gly Arg Val Thr Leu Thr Ala Glu Lys Gly
705                 710                 715                 720 cag ccc tac gtc ctc gtg ccg aac ggc ggc agg gca ccg cac cgc gac         2208
Gln Pro Tyr Val Leu Val Pro Asn Gly Gly Arg Ala Pro His Arg Asp
                725                 730                 735 gcc cac tac ggc gag ttc acc ggg ctg tcc gac ccc ggc ttc aac ggc         2256
Ala His Tyr Gly Glu Phe Thr Gly Leu Ser Asp Pro Gly Phe Asn Gly
            740                 745                 750 ggg gac ctc gac gcc tgg aac gcg agc ggc ggc gcg gag atc gtc cgg         2304
Gly Asp Leu Asp Ala Trp Asn Ala Ser Gly Gly Ala Glu Ile Val Arg
            755                 760                 765 gcc ggc aac ggg gac aac gtg gtc cgc ctg ggc gag gac gcc tcg ggc         2352
Ala Gly Asn Gly Asp Asn Val Val Arg Leu Gly Glu Asp Ala Ser Gly
            770                 775                 780 atc gcg cag cgg gtc cgc ggc ctg acc ccg ggc gag cgg tac acg ctc         2400
Ile Ala Gln Arg Val Arg Gly Leu Thr Pro Gly Glu Arg Tyr Thr Leu
785                 790                 795                 800 ggc gcg gac gtc ggg atc ggc ccc ggc gag cgc cgg gag acg acg ctg         2448
Gly Ala Asp Val Gly Ile Gly Pro Gly Glu Arg Arg Glu Thr Thr Leu
                805                 810                 815
```

```
cgg gtg cgc ggc ggc aag gac agc gag gcc agg acc ttc gac atc acg        2496
Arg Val Arg Gly Gly Lys Asp Ser Glu Ala Arg Thr Phe Asp Ile Thr
        820                 825                 830 ccg gcg cgg aac agg atg gcg tcc gac gag aag cga gac acg tac tcc        2544
Pro Ala Arg Asn Arg Met Ala Ser Asp Glu Lys Arg Asp Thr Tyr Ser
835                 840                 845 cag cgg gcc tcg gtc tcc ttc acc gcg ccg cgc gac ggc tcg gtc acc        2592
Gln Arg Ala Ser Val Ser Phe Thr Ala Pro Arg Asp Gly Ser Val Thr
    850                 855                 860 gtg gag ctc ggg gcg gtc gcc ggt ggc gcc ccg gtg gtc ctg gac gac        2640
Val Glu Leu Gly Ala Val Ala Gly Gly Ala Pro Val Val Leu Asp Asp
865                 870                 875                 880 gta cgg gtc atg gtg gac acc acc gct ccg ctc ccc cgc tcc cag gac        2688
Val Arg Val Met Val Asp Thr Thr Ala Pro Leu Pro Arg Ser Gln Asp
            885                 890                 895 ggc acg gtc gtc gcc cac gac gac ttc gag ggc aac cgg ccc ggc tgg        2736
Gly Thr Val Val Ala His Asp Asp Phe Glu Gly Asn Arg Pro Gly Trp
        900                 905                 910 gga ccg ttc gtc aag ggc gac gcc ggc ggc gtc acc gac ccc cgc acc        2784
Gly Pro Phe Val Lys Gly Asp Ala Gly Gly Val Thr Asp Pro Arg Thr
            915                 920                 925 agc atc agc gac ctg cac gcg ccc tac agc cag aag gag tgg aag aac        2832
Ser Ile Ser Asp Leu His Ala Pro Tyr Ser Gln Lys Glu Trp Lys Asn
930                 935                 940 acc tac tcg ccc tac gac acc ggc gcg ctg aag ggc agg gcc gtc gac        2880
Thr Tyr Ser Pro Tyr Asp Thr Gly Ala Leu Lys Gly Arg Ala Val Asp
945                 950                 955                 960 gac gtg ctc gcg ggc cgg cac tcg ctg aag tcc cac gcc gag aac acc        2928
Asp Val Leu Ala Gly Arg His Ser Leu Lys Ser His Ala Glu Asn Thr
                965                 970                 975 ggg ctg gtc cac cgc acg acc cct gcc acc gtg ccg ttc gag gag ggc        2976
Gly Leu Val His Arg Thr Thr Pro Ala Thr Val Pro Phe Glu Glu Gly
            980                 985                 990 cac cgg tac cgg gtc tcc ttc tcg tac cag acc aac gtc gag ggc cag        3024
His Arg Tyr Arg Val Ser Phe Ser Tyr Gln Thr Asn Val Glu Gly Gln
        995                 1000                1005 tgg gcc tgg gtc acc ggc gcg gac cgg gtc gcc gac ggg acg acg             3069
Trp Ala Trp Val Thr Gly Ala Asp Arg Val Ala Asp Gly Thr Thr
    1010                1015                1020 acc tcg cgg gac atc acc cgt gac gtc ctg gca ccc gcc ctg gac             3114
Thr Ser Arg Asp Ile Thr Arg Asp Val Leu Ala Pro Ala Leu Asp
1025                1030                1035 acg gcg gcc tac tcc cgc gag ttc gtc gcc ggc tgc ggg gac acc             3159
Thr Ala Ala Tyr Ser Arg Glu Phe Val Ala Gly Cys Gly Asp Thr
    1040                1045                1050 tgg gtc ggg ctg cgc aga ctc ggc agc gcc cgg ggc acc gat ctc             3204
Trp Val Gly Leu Arg Arg Leu Gly Ser Ala Arg Gly Thr Asp Leu
1055                1060                1065 gtc ctc gac gac ttc acg gtg acc gac ctc ggc gag gcg gac acc             3249
Val Leu Asp Asp Phe Thr Val Thr Asp Leu Gly Glu Ala Asp Thr
1070                1075                1080 ggg gcc gcc tgc gcc gct gtc acg gcc ccg tcc ggc gcc gaa ctg             3294
Gly Ala Ala Cys Ala Ala Val Thr Ala Pro Ser Gly Ala Glu Leu
    1085                1090                1095 agc ccc ggg gtc ccc ggt gag tac gtc acg gcg ttc acc aac cac             3339
Ser Pro Gly Val Pro Gly Glu Tyr Val Thr Ala Phe Thr Asn His
1100                1105                1110 gag tcc gcc ggc gcc gag aac gtg ggc atc gcc ctc cag ggt ctg             3384
Glu Ser Ala Gly Ala Glu Asn Val Gly Ile Ala Leu Gln Gly Leu
    1115                1120                1125
```

```
ccc gag ggc tgg aag gcc gag gtg aag gag aag gac ggc aat ctc      3429
Pro Glu Gly Trp Lys Ala Glu Val Lys Glu Lys Asp Gly Asn Leu
    1130            1135                1140 ttc gag cgc gtg cag ccg ggc gcg acc gtg cgc acc acc tgg ctc      3474
Phe Glu Arg Val Gln Pro Gly Ala Thr Val Arg Thr Thr Trp Leu
1145                1150                1155 ctc acc ccg ccc gcc ggc acg gcc ggc acc tcc gcc acg tgg cag      3519
Leu Thr Pro Pro Ala Gly Thr Ala Gly Thr Ser Ala Thr Trp Gln
    1160            1165                1170 gtg acg gcc gcc tac gca cac gag gga gcc acc agg acg gtc tcc      3564
Val Thr Ala Ala Tyr Ala His Glu Gly Ala Thr Arg Thr Val Ser
1175                1180                1185 acc ggg gcc cgc gcc gcg gtg acc gac gaa ccg gta ctg gcc ccg      3609
Thr Gly Ala Arg Ala Ala Val Thr Asp Glu Pro Val Leu Ala Pro
    1190            1195                1200 gct tcg acg acc gcg acc gcc gac tcg gag aac acc tcg tcg ggc      3654
Ala Ser Thr Thr Ala Thr Ala Asp Ser Glu Asn Thr Ser Ser Gly
1205                1210                1215 gcc tcc gaa ggg ccg gtg tcc aac gtc ctc gac ggt gac gcc ggc      3699
Ala Ser Glu Gly Pro Val Ser Asn Val Leu Asp Gly Asp Ala Gly
    1220            1225                1230 acc atc tgg cac acc gac tac acc acc tcc cag gcg ccg tat ccg      3744
Thr Ile Trp His Thr Asp Tyr Thr Thr Ser Gln Ala Pro Tyr Pro
1235                1240                1245 cac tgg gtg acg ctg aag ctc ggc ggc gcc gcc gac gtc gac ggg      3789
His Trp Val Thr Leu Lys Leu Gly Gly Ala Ala Asp Val Asp Gly
    1250            1255                1260 ttc ggg tac ctg ggc cga cag agc ggg ggc ccg aac gga cgc gtc      3834
Phe Gly Tyr Leu Gly Arg Gln Ser Gly Gly Pro Asn Gly Arg Val
1265                1270                1275 gcc gac tac gag gtc gcc gtg tcg gac gac ggc gag gcg tgg acg      3879
Ala Asp Tyr Glu Val Ala Val Ser Asp Asp Gly Glu Ala Trp Thr
    1280            1285                1290 acg gtg gcc acc ggc acc ctg aag gac gtc ccg cgg acc cag cgc      3924
Thr Val Ala Thr Gly Thr Leu Lys Asp Val Pro Arg Thr Gln Arg
1295                1300                1305 gtc tcc ttc gac cgg gtc cgc gcc tcc tac gtg cgc ttc acc gcc      3969
Val Ser Phe Asp Arg Val Arg Ala Ser Tyr Val Arg Phe Thr Ala
    1310            1315                1320 ctc gac gcg ctc aac ggg cag ccc tac gcg gcc gcc gcg gag atg      4014
Leu Asp Ala Leu Asn Gly Gln Pro Tyr Ala Ala Ala Ala Glu Met
1325                1330                1335 cgc gtg tac ggc gtg ccc gtg gac ctg ccc acg ggc tac ccg ccg      4059
Arg Val Tyr Gly Val Pro Val Asp Leu Pro Thr Gly Tyr Pro Pro
    1340            1345                1350 ggc gaa cgc ccc gcc gac gcc cgc tga                              4086
Gly Glu Arg Pro Ala Asp Ala Arg
1355                1360
```

<210> SEQ ID NO 10
<211> LENGTH: 1361
<212> TYPE: PRT
<213> ORGANISM: Streptomyces coelicolor A3(2)

<400> SEQUENCE: 10

```
Met Ala Ala Ile Thr Pro Lys Arg Ser Val Arg Val Asp Thr Ser Thr
1               5                   10                  15

Gly Ser Ser Ser Pro Pro Thr Gly Arg Ala Arg Val Arg Arg His Gly
            20                  25                  30
```

-continued

```
Ala Val Val Ala Ala Leu Gly Leu Thr Ala Gly Leu Leu Ser Ala Ala
         35                  40                  45

Ala Leu Pro Ala Gly Ala Ala Pro Pro Arg Pro Ala Ala Ala Ala Ala
 50                  55                  60

Pro Ala Gly Ala Pro Thr Pro Val Glu Leu Ser Arg Gly Gly Leu Thr
 65                  70                  75                  80

Val Thr Val Ala Lys Glu Phe Pro Gln Val Ile Ser Tyr Arg Leu Gly
                 85                  90                  95

Arg Arg Gly Leu Asp Gly Arg Ala Thr Ala Leu Asp Gly Phe Thr Val
                100                 105                 110

Asn Gly Glu Ser His Arg Ala Thr Thr Val Lys Ala Lys Gly Ser
            115                 120                 125

Arg Ala Val Tyr Thr Ser Thr Phe Glu Asp Leu Pro Gly Leu Thr Ile
        130                 135                 140

Thr Ser Ser Ile Thr Val Thr Lys Glu Thr Thr Val Val Phe Ala Val
145                 150                 155                 160

Glu Lys Ile Ser Gly Glu Ala Ala Pro Gly Val Arg Thr Leu Ala Ile
                165                 170                 175

Pro Gly Gln Ser Leu Val Ser Val Asp Ser Ala Glu Pro Gly Ala Asn
                180                 185                 190

Leu Ala Arg Thr Lys Ile Ser Thr Asp Ser Thr Thr Ala Asp Arg
            195                 200                 205

Phe Val Pro Val Thr Gly Asp Thr Ala Pro Asp Lys Gly Pro Val Gly
        210                 215                 220

Thr Pro Tyr Ala Phe Val Gly Asn Ala Gln Leu Ser Ala Gly Ile Ile
225                 230                 235                 240

Thr Asn Ala Thr Glu Asp Ser Pro Gln Asp Asn Thr Asp Trp Asn
                245                 250                 255

Thr Arg Leu Gln Ser Arg Ile Val Asp Glu Gly Glu Gly Arg Arg Arg
            260                 265                 270

Ala Glu Leu Ser Ala Gly Thr Tyr Thr Tyr His Pro Glu Gly Ala Thr
        275                 280                 285

Asp Pro Arg Val Asp Thr Tyr Glu Leu Pro Arg Ala Thr Val Val Leu
290                 295                 300

Ala Ala Asp Ala Asn Arg Asp Gly Thr Val Asp Trp Gln Asp Gly Ala
305                 310                 315                 320

Ile Ala His Arg Glu His Met Arg Arg Pro Leu Gly Ala Asp Arg Val
                325                 330                 335

Pro Glu Arg Val Val Gln Arg Ile Pro Phe Asn Phe Ala Ser Gln Ala
            340                 345                 350

Thr Asn Pro Phe Leu Lys Thr Leu Asp Asn Thr Lys Arg Ile Ser Met
        355                 360                 365

Ala Thr Asp Asp Leu Gly Gln Trp Val Leu Glu Lys Gly Tyr Ala Ser
        370                 375                 380

Glu Gly His Asp Ser Ala His Pro Asp Tyr Gly Gly Asn Glu Asn Val
385                 390                 395                 400

Arg Ala Gly Gly Trp Lys Asp Leu Asn Arg Leu Thr Arg Thr Gly Ala
                405                 410                 415

Gly Tyr Asn Ala Asp Phe Ala Val His Val Asn Ala Thr Glu Ala Tyr
            420                 425                 430

Ala Gln Ala Arg Thr Phe Thr Glu Asp Met Val Ala Gly Gln Ala Asp
        435                 440                 445

Gly Trp Asp Trp Leu Asn Gln Ala Tyr His Ile Asp Gln Arg Lys Asp
```

-continued

```
            450                 455                 460
Leu Gly Thr Gly Ala Val Leu Asp Arg Phe Lys Gln Leu Arg Lys Glu
465                 470                 475                 480

Ala Pro Gly Ile Arg Thr Val Tyr Ile Asp Ala Tyr Tyr Ser Ser Gly
            485                 490                 495

Trp Leu Ala Asp Gly Leu Ala Ala Gly Leu Arg Glu Met Gly Phe Glu
            500                 505                 510

Val Ala Thr Glu Trp Ala Tyr Lys Phe Glu Gly Thr Ser Val Trp Ser
            515                 520                 525

His Trp Ala Ala Asp Lys Asn Tyr Gly Gly Ala Thr Asn Lys Gly Ile
530                 535                 540

Asn Ser Asp Ile Val Arg Phe Ile Ala Asn Ala Asp Arg Asp Val Trp
545                 550                 555                 560

Asn Val Asp Pro Leu Leu Gly Gly Ala Ser Val Val Glu Phe Glu Gly
            565                 570                 575

Trp Thr Gly Gln Asp Asp Trp Asn Ala Phe Tyr Arg Asn Ile Trp Thr
            580                 585                 590

Asp Asn Leu Pro Thr Lys Phe Leu Gln His Phe Gln Val Leu Asp Trp
            595                 600                 605

Asp Arg Gly Arg Ser Ala Arg Leu Thr Gly Gly Val Asp Val Lys Ser
            610                 615                 620

Val Asp Gly Glu Arg Arg Ile Ser Met Asp Gly Thr Glu Val Leu Lys
625                 630                 635                 640

Gly Asp Thr Tyr Leu Leu Pro Trp Gln Asn Ala Gly Lys Asp Asp Gly
            645                 650                 655

Thr Ser Ser Pro Arg Asp Ala Asp Lys Met Tyr Phe Tyr Ser Ala Ser
            660                 665                 670

Gly Gly Glu His Thr Phe Glu Leu Thr Gly Gln Phe Ala Gly Thr Glu
            675                 680                 685

Asp Phe Thr Leu Tyr Glu Leu Thr Asp Gln Gly Arg Ala Glu Lys Ala
            690                 695                 700

Arg Val Thr Ala His Glu Gly Arg Val Thr Leu Thr Ala Glu Lys Gly
705                 710                 715                 720

Gln Pro Tyr Val Leu Val Pro Asn Gly Gly Arg Ala Pro His Arg Asp
            725                 730                 735

Ala His Tyr Gly Glu Phe Thr Gly Leu Ser Asp Pro Gly Phe Asn Gly
            740                 745                 750

Gly Asp Leu Asp Ala Trp Asn Ala Ser Gly Gly Ala Glu Ile Val Arg
            755                 760                 765

Ala Gly Asn Gly Asp Asn Val Val Arg Leu Gly Glu Asp Ala Ser Gly
            770                 775                 780

Ile Ala Gln Arg Val Arg Gly Leu Thr Pro Gly Glu Arg Tyr Thr Leu
785                 790                 795                 800

Gly Ala Asp Val Gly Ile Gly Pro Gly Glu Arg Glu Thr Thr Leu
            805                 810                 815

Arg Val Arg Gly Gly Lys Asp Ser Glu Ala Arg Thr Phe Asp Ile Thr
            820                 825                 830

Pro Ala Arg Asn Arg Met Ala Ser Asp Glu Lys Arg Asp Thr Tyr Ser
            835                 840                 845

Gln Arg Ala Ser Val Ser Phe Thr Ala Pro Arg Asp Gly Ser Val Thr
            850                 855                 860

Val Glu Leu Gly Ala Val Ala Gly Gly Ala Pro Val Val Leu Asp Asp
865                 870                 875                 880
```

-continued

Val Arg Val Met Val Asp Thr Thr Ala Pro Leu Pro Arg Ser Gln Asp
            885                 890                 895

Gly Thr Val Val Ala His Asp Asp Phe Glu Gly Asn Arg Pro Gly Trp
            900                 905                 910

Gly Pro Phe Val Lys Gly Asp Ala Gly Gly Val Thr Asp Pro Arg Thr
            915                 920                 925

Ser Ile Ser Asp Leu His Ala Pro Tyr Ser Gln Lys Glu Trp Lys Asn
            930                 935                 940

Thr Tyr Ser Pro Tyr Asp Thr Gly Ala Leu Lys Gly Arg Ala Val Asp
945                 950                 955                 960

Asp Val Leu Ala Gly Arg His Ser Leu Lys Ser His Ala Glu Asn Thr
            965                 970                 975

Gly Leu Val His Arg Thr Thr Pro Ala Thr Val Pro Phe Glu Glu Gly
            980                 985                 990

His Arg Tyr Arg Val Ser Phe Ser Tyr Gln Thr Asn Val Glu Gly Gln
            995                 1000                1005

Trp Ala Trp Val Thr Gly Ala Asp Arg Val Ala Asp Gly Thr Thr
    1010                1015                1020

Thr Ser Arg Asp Ile Thr Arg Asp Val Leu Ala Pro Ala Leu Asp
    1025                1030                1035

Thr Ala Ala Tyr Ser Arg Glu Phe Val Ala Gly Cys Gly Asp Thr
    1040                1045                1050

Trp Val Gly Leu Arg Arg Leu Gly Ser Ala Arg Gly Thr Asp Leu
    1055                1060                1065

Val Leu Asp Asp Phe Thr Val Thr Asp Leu Gly Glu Ala Asp Thr
    1070                1075                1080

Gly Ala Ala Cys Ala Ala Val Thr Ala Pro Ser Gly Ala Glu Leu
    1085                1090                1095

Ser Pro Gly Val Pro Gly Glu Tyr Val Thr Ala Phe Thr Asn His
    1100                1105                1110

Glu Ser Ala Gly Ala Glu Asn Val Gly Ile Ala Leu Gln Gly Leu
    1115                1120                1125

Pro Glu Gly Trp Lys Ala Glu Val Lys Glu Lys Asp Gly Asn Leu
    1130                1135                1140

Phe Glu Arg Val Gln Pro Gly Ala Thr Val Arg Thr Thr Trp Leu
    1145                1150                1155

Leu Thr Pro Pro Ala Gly Thr Ala Gly Thr Ser Ala Thr Trp Gln
    1160                1165                1170

Val Thr Ala Ala Tyr Ala His Glu Gly Ala Thr Arg Thr Val Ser
    1175                1180                1185

Thr Gly Ala Arg Ala Ala Val Thr Asp Glu Pro Val Leu Ala Pro
    1190                1195                1200

Ala Ser Thr Thr Ala Thr Ala Asp Ser Glu Asn Thr Ser Ser Gly
    1205                1210                1215

Ala Ser Glu Gly Pro Val Ser Asn Val Leu Asp Gly Asp Ala Gly
    1220                1225                1230

Thr Ile Trp His Thr Asp Tyr Thr Thr Ser Gln Ala Pro Tyr Pro
    1235                1240                1245

His Trp Val Thr Leu Lys Leu Gly Gly Ala Ala Asp Val Asp Gly
    1250                1255                1260

Phe Gly Tyr Leu Gly Arg Gln Ser Gly Gly Pro Asn Gly Arg Val
    1265                1270                1275

```
Ala Asp Tyr Glu Val Ala Val Ser Asp Asp Gly Glu Ala Trp Thr
    1280                1285                1290

Thr Val Ala Thr Gly Thr Leu Lys Asp Val Pro Arg Thr Gln Arg
    1295                1300                1305

Val Ser Phe Asp Arg Val Arg Ala Ser Tyr Val Arg Phe Thr Ala
    1310                1315                1320

Leu Asp Ala Leu Asn Gly Gln Pro Tyr Ala Ala Ala Ala Glu Met
    1325                1330                1335

Arg Val Tyr Gly Val Pro Val Asp Leu Pro Thr Gly Tyr Pro Pro
    1340                1345                1350

Gly Glu Arg Pro Ala Asp Ala Arg
    1355                1360

<210> SEQ ID NO 11
<211> LENGTH: 3975
<212> TYPE: DNA
<213> ORGANISM: Enterococcus faecalis V583
<220> FEATURE:
<221> NAME/KEY: CDS
<222> LOCATION: (1)..(3975)

<400> SEQUENCE: 11
```

| | | | | | | | | | | | | | | | |
|---|---|---|---|---|---|---|---|---|---|---|---|---|---|---|---|
| atg | aaa | cat | gga | aaa | ata | aaa | cga | ttt | agt | aca | ttg | aca | cta | ttg | gca | 48 |
| Met | Lys | His | Gly | Lys | Ile | Lys | Arg | Phe | Ser | Thr | Leu | Thr | Leu | Leu | Ala | |
| 1 | | | | 5 | | | | | 10 | | | | | 15 | | |
| agc | gca | acg | att | tta | gta | cca | tta | agt | acg | tct | gca | gaa | gaa | aca | aca | 96 |
| Ser | Ala | Thr | Ile | Leu | Val | Pro | Leu | Ser | Thr | Ser | Ala | Glu | Glu | Thr | Thr | |
| | | | 20 | | | | | 25 | | | | | 30 | | | |
| aac | agc | agc | act | gaa | aca | agc | tca | tca | atg | gtg | gaa | cct | acc | gca | aca | 144 |
| Asn | Ser | Ser | Thr | Glu | Thr | Ser | Ser | Ser | Met | Val | Glu | Pro | Thr | Ala | Thr | |
| | | 35 | | | | | 40 | | | | | 45 | | | | |
| gaa | gaa | aaa | ttg | tgg | caa | tct | gat | ttt | cca | gga | ggg | aaa | act | ggt | gag | 192 |
| Glu | Glu | Lys | Leu | Trp | Gln | Ser | Asp | Phe | Pro | Gly | Gly | Lys | Thr | Gly | Glu | |
| 50 | | | | | 55 | | | | | 60 | | | | | | |
| tgg | caa | gat | gtg | att | ggt | aaa | aca | aat | cga | gaa | tta | gca | gga | gag | tca | 240 |
| Trp | Gln | Asp | Val | Ile | Gly | Lys | Thr | Asn | Arg | Glu | Leu | Ala | Gly | Glu | Ser | |
| 65 | | | | 70 | | | | | 75 | | | | | 80 | | |
| ttg | gcg | att | tca | cga | gat | gca | gca | gca | ggt | aat | aat | gcc | gta | tct | tta | 288 |
| Leu | Ala | Ile | Ser | Arg | Asp | Ala | Ala | Ala | Gly | Asn | Asn | Ala | Val | Ser | Leu | |
| | | | 85 | | | | | 90 | | | | | 95 | | | |
| aat | tta | gat | tcc | cct | aaa | tta | gct | gat | ggt | gaa | gta | gaa | aca | aag | ttt | 336 |
| Asn | Leu | Asp | Ser | Pro | Lys | Leu | Ala | Asp | Gly | Glu | Val | Glu | Thr | Lys | Phe | |
| | | | 100 | | | | | 105 | | | | | 110 | | | |
| aaa | tac | act | gct | gga | agc | ggt | cga | acg | ggt | gtg | att | ata | cgt | ggt | aat | 384 |
| Lys | Tyr | Thr | Ala | Gly | Ser | Gly | Arg | Thr | Gly | Val | Ile | Ile | Arg | Gly | Asn | |
| | | 115 | | | | | 120 | | | | | 125 | | | | |
| acc | aaa | gat | agc | tgg | gtt | ttt | gta | ggc | tat | aac | gcg | aat | ggc | aaa | tgg | 432 |
| Thr | Lys | Asp | Ser | Trp | Val | Phe | Val | Gly | Tyr | Asn | Ala | Asn | Gly | Lys | Trp | |
| | 130 | | | | | 135 | | | | | 140 | | | | | |
| tta | gtt | gaa | agc | cct | aat | tcg | tgg | aat | gat | tca | att | tct | ggg | cca | acg | 480 |
| Leu | Val | Glu | Ser | Pro | Asn | Ser | Trp | Asn | Asp | Ser | Ile | Ser | Gly | Pro | Thr | |
| 145 | | | | | 150 | | | | | 155 | | | | | 160 | |
| tta | aat | gaa | gat | acg | aat | tat | ttg | ttg | aaa | gta | cgt | tat | gtt | ggt | gaa | 528 |
| Leu | Asn | Glu | Asp | Thr | Asn | Tyr | Leu | Leu | Lys | Val | Arg | Tyr | Val | Gly | Glu | |
| | | | | 165 | | | | | 170 | | | | | 175 | | |
| aaa | att | act | atc | tgg | ctt | aac | acc | acg | ttg | att | tac | gaa | gga | gaa | cct | 576 |
| Lys | Ile | Thr | Ile | Trp | Leu | Asn | Thr | Thr | Leu | Ile | Tyr | Glu | Gly | Glu | Pro | |
| | | | 180 | | | | | 185 | | | | | 190 | | | |
| gtt | ttg | gcc | aat | gga | gac | aaa | att | cca | aca | gaa | gcc | gga | cat | gtg | ggt | 624 |
| Val | Leu | Ala | Asn | Gly | Asp | Lys | Ile | Pro | Thr | Glu | Ala | Gly | His | Val | Gly | |

-continued

```
                195                 200                 205
gtc cgt ttg tgg tac gac aaa aaa att gtc aat tat gac tat ttt aaa        672
Val Arg Leu Trp Tyr Asp Lys Lys Ile Val Asn Tyr Asp Tyr Phe Lys
        210                 215                 220 aat ggc ccc gta gat agc att cca gaa att gtg cca gaa gtg aca caa        720
Asn Gly Pro Val Asp Ser Ile Pro Glu Ile Val Pro Glu Val Thr Gln
225                 230                 235                 240 att gcg cca gtc aaa gtt ttt aca aaa att ggt gtc gca cca aaa tta        768
Ile Ala Pro Val Lys Val Phe Thr Lys Ile Gly Val Ala Pro Lys Leu
                245                 250                 255 ccg aaa caa gta aaa gtg acc tat aat act ggt aaa gaa gcc aat gaa        816
Pro Lys Gln Val Lys Val Thr Tyr Asn Thr Gly Lys Glu Ala Asn Glu
            260                 265                 270 gca gtc cgt tgg aat gaa atc gat cct gat gca tat aaa gaa cca gga        864
Ala Val Arg Trp Asn Glu Ile Asp Pro Asp Ala Tyr Lys Glu Pro Gly
        275                 280                 285 act ttt gaa gtc gac ggt act ttg gaa aat aca aac atc aaa gca aaa        912
Thr Phe Glu Val Asp Gly Thr Leu Glu Asn Thr Asn Ile Lys Ala Lys
    290                 295                 300 gcc agc att gtt gtt gct aaa gac aat gaa gct gaa aaa ggc gac aaa        960
Ala Ser Ile Val Val Ala Lys Asp Asn Glu Ala Glu Lys Gly Asp Lys
305                 310                 315                 320 atc tct tcc gca gat tta aca gcc gtg gtt gat cca caa ttt cca cga       1008
Ile Ser Ser Ala Asp Leu Thr Ala Val Val Asp Pro Gln Phe Pro Arg
                325                 330                 335 att att cgc tac gaa gac cct cag agt aat caa gtg att ttt aat ggc       1056
Ile Ile Arg Tyr Glu Asp Pro Gln Ser Asn Gln Val Ile Phe Asn Gly
            340                 345                 350 caa cac gag aaa att gac caa gta atg att gat ggc aaa gca tat aaa       1104
Gln His Glu Lys Ile Asp Gln Val Met Ile Asp Gly Lys Ala Tyr Lys
        355                 360                 365 gca act gct gaa aaa cag aag agt gaa gca aat caa gcc gtt tat aac       1152
Ala Thr Ala Glu Lys Gln Lys Ser Glu Ala Asn Gln Ala Val Tyr Asn
    370                 375                 380 gta gct gtc cca gaa att ggt ttg cgt ttc aca acg aca ttg act gtt       1200
Val Ala Val Pro Glu Ile Gly Leu Arg Phe Thr Thr Thr Leu Thr Val
385                 390                 395                 400 tcc gaa ggc caa gaa tta gct atg aaa ctc tca gat att cgt gaa gaa       1248
Ser Glu Gly Gln Glu Leu Ala Met Lys Leu Ser Asp Ile Arg Glu Glu
                405                 410                 415 gga acc aaa ata cac aca att tca att cca aat caa ggc ttg att tct       1296
Gly Thr Lys Ile His Thr Ile Ser Ile Pro Asn Gln Gly Leu Ile Ser
            420                 425                 430 gtc aat agt aca gat gaa ggg gcg act ttt gct ggc gtt gtg atg aat       1344
Val Asn Ser Thr Asp Glu Gly Ala Thr Phe Ala Gly Val Val Met Asn
        435                 440                 445 act ggg aca aat gca aat aac gga aat aaa aat ggt gat act atc caa       1392
Thr Gly Thr Asn Ala Asn Asn Gly Asn Lys Asn Gly Asp Thr Ile Gln
    450                 455                 460 gat tta act aca aca agc caa gaa gaa acg aaa aaa tat atg tat ggt       1440
Asp Leu Thr Thr Thr Ser Gln Glu Glu Thr Lys Lys Tyr Met Tyr Gly
465                 470                 475                 480 ttc tta aat acg gcg aat tat gct gca agt ttt tgg acg aac gcc tat       1488
Phe Leu Asn Thr Ala Asn Tyr Ala Ala Ser Phe Trp Thr Asn Ala Tyr
                485                 490                 495 gga gac ggc tct gtc gat ggt agt gac aac aat cga atc cat aaa caa       1536
Gly Asp Gly Ser Val Asp Gly Ser Asp Asn Asn Arg Ile His Lys Gln
            500                 505                 510 aca aaa gaa gcg gcg act ggt ttt gta aca acc ttg tca agt ggg gca       1584
```

-continued

```
                        Thr Lys Glu Ala Ala Thr Gly Phe Val Thr Thr Leu Ser Ser Gly Ala
                                515                 520                 525 tgg acc tat cga cca ttt gat gca ccg gaa gat tac aca act gga gaa       1632
Trp Thr Tyr Arg Pro Phe Asp Ala Pro Glu Asp Tyr Thr Thr Gly Glu
        530                 535                 540 acg cca gaa gtg aaa gtt aaa ttc tca aaa gat agc aac gac gac aat       1680
Thr Pro Glu Val Lys Val Lys Phe Ser Lys Asp Ser Asn Asp Asp Asn
545                 550                 555                 560 cgg gtg gat tgg caa gat gcg gca att ggg ttc cgt tca att atg aat       1728
Arg Val Asp Trp Gln Asp Ala Ala Ile Gly Phe Arg Ser Ile Met Asn
                565                 570                 575 aac cca atg ggt gcg gaa aaa gtc cct gaa tta gtc aac caa cgg att       1776
Asn Pro Met Gly Ala Glu Lys Val Pro Glu Leu Val Asn Gln Arg Ile
        580                 585                 590 cct ttt aac ttt gct agt cag gcg aca aac cca ttc tta gtg acg tta       1824
Pro Phe Asn Phe Ala Ser Gln Ala Thr Asn Pro Phe Leu Val Thr Leu
            595                 600                 605 gac gaa tca aaa cgt att tac aat tta aca gat gga tta gga caa atg       1872
Asp Glu Ser Lys Arg Ile Tyr Asn Leu Thr Asp Gly Leu Gly Gln Met
        610                 615                 620 aat tta cta aaa ggg tat caa aat gaa gga cat gat tct gcg cat cca       1920
Asn Leu Leu Lys Gly Tyr Gln Asn Glu Gly His Asp Ser Ala His Pro
625                 630                 635                 640 gat tac ggt gct att ggt cag cga cct ggt ggg gaa caa gcg ttg aat       1968
Asp Tyr Gly Ala Ile Gly Gln Arg Pro Gly Gly Glu Gln Ala Leu Asn
                645                 650                 655 caa tta att gat gaa gga cat aaa tta aat gcc gtt ttc ggt gtg cat       2016
Gln Leu Ile Asp Glu Gly His Lys Leu Asn Ala Val Phe Gly Val His
        660                 665                 670 att aat gac acc gag tct tac cca gaa gca aaa gga ttt aat gag gaa       2064
Ile Asn Asp Thr Glu Ser Tyr Pro Glu Ala Lys Gly Phe Asn Glu Glu
            675                 680                 685 tta gtt gat cca acg aag cgt ggc tgg gat tgg tta gat ccg tct tat       2112
Leu Val Asp Pro Thr Lys Arg Gly Trp Asp Trp Leu Asp Pro Ser Tyr
        690                 695                 700 ttt att aaa caa aga ccc gat aca ttg agt ggt cgt cgc tat gag cgc       2160
Phe Ile Lys Gln Arg Pro Asp Thr Leu Ser Gly Arg Arg Tyr Glu Arg
705                 710                 715                 720 ttt aaa gaa tta aaa caa aaa gca ccg aat cta gat tat att tat gtt       2208
Phe Lys Glu Leu Lys Gln Lys Ala Pro Asn Leu Asp Tyr Ile Tyr Val
                725                 730                 735 gat gtt tgg ggc aac caa ggc gaa tca ggt tgg gca agt cgt caa cta       2256
Asp Val Trp Gly Asn Gln Gly Glu Ser Gly Trp Ala Ser Arg Gln Leu
        740                 745                 750 agt aaa gaa att aat tca ctc ggt tgg ttt aca acc aat gaa ttt ccg       2304
Ser Lys Glu Ile Asn Ser Leu Gly Trp Phe Thr Thr Asn Glu Phe Pro
            755                 760                 765 aat gct tta gag tat gac tcg gtt tgg aac cat tgg tct gca gaa aaa       2352
Asn Ala Leu Glu Tyr Asp Ser Val Trp Asn His Trp Ser Ala Glu Lys
        770                 775                 780 gat tac ggc ggt aca aca acg aaa ggc ttt aac agt aca atc gtt cgt       2400
Asp Tyr Gly Gly Thr Thr Thr Lys Gly Phe Asn Ser Thr Ile Val Arg
785                 790                 795                 800 ttt att cgg aat cat caa aaa gac act tgg att att tcc gac aac cct       2448
Phe Ile Arg Asn His Gln Lys Asp Thr Trp Ile Ile Ser Asp Asn Pro
                805                 810                 815 ttg tta ggt gga gct gaa ttt gaa gcc tat gaa ggt tgg gtg ggt aaa       2496
Leu Leu Gly Gly Ala Glu Phe Glu Ala Tyr Glu Gly Trp Val Gly Lys
        820                 825                 830
```

```
acc aat ttt aat acc tat cgc caa aaa act ttt gcc att aat gtc cca      2544
Thr Asn Phe Asn Thr Tyr Arg Gln Lys Thr Phe Ala Ile Asn Val Pro
        835                 840                 845 act aag ttc tta caa cat tac caa att aca aac tgg gaa act aca aca      2592
Thr Lys Phe Leu Gln His Tyr Gln Ile Thr Asn Trp Glu Thr Thr Thr
850                 855                 860 gca gca gat ggt caa atc tat ggc aca att aaa tta gcg aac ggt gct      2640
Ala Ala Asp Gly Gln Ile Tyr Gly Thr Ile Lys Leu Ala Asn Gly Ala
865                 870                 875                 880 gaa aaa gtg acc gtt act caa gca gat gct aat tcg cca aga agc att      2688
Glu Lys Val Thr Val Thr Gln Ala Asp Ala Asn Ser Pro Arg Ser Ile
            885                 890                 895 acg tta aat gag aca gaa gtt cta aaa ggt gat gcg tat cta ctg cct      2736
Thr Leu Asn Glu Thr Glu Val Leu Lys Gly Asp Ala Tyr Leu Leu Pro
        900                 905                 910 tgg aat gtc aat ggt caa gac aaa cta tat cac tgg aat cca aaa ggc      2784
Trp Asn Val Asn Gly Gln Asp Lys Leu Tyr His Trp Asn Pro Lys Gly
        915                 920                 925 ggt acc agc act tgg tca ttg gat aag aaa atg caa gga aaa acg aat      2832
Gly Thr Ser Thr Trp Ser Leu Asp Lys Lys Met Gln Gly Lys Thr Asn
930                 935                 940 tta cat tta tat gaa tta aca gat caa ggg cgt att gac aaa ggc gca      2880
Leu His Leu Tyr Glu Leu Thr Asp Gln Gly Arg Ile Asp Lys Gly Ala
945                 950                 955                 960 att gcc act aca aat aac caa gtg acc atc caa gcc gag gct aat aca      2928
Ile Ala Thr Thr Asn Asn Gln Val Thr Ile Gln Ala Glu Ala Asn Thr
            965                 970                 975 ccg tat gtc att gct gaa cct gac agt att gaa ccg atg aca ttt gga      2976
Pro Tyr Val Ile Ala Glu Pro Asp Ser Ile Glu Pro Met Thr Phe Gly
        980                 985                 990 aca gga aca cca ttt aaa gat cct gga ttt aat gaa gcc aat acc tta      3024
Thr Gly Thr Pro Phe Lys Asp Pro Gly Phe Asn Glu Ala Asn Thr Leu
        995                 1000                1005 aaa aat aac tgg aaa gtt ttc cga ggt gat gga gag gtt aaa aaa         3069
Lys Asn Asn Trp Lys Val Phe Arg Gly Asp Gly Glu Val Lys Lys
    1010                1015                1020 gat gcc aat ggt gat tat gtc ttt agt tca gaa aaa gaa aga acc         3114
Asp Ala Asn Gly Asp Tyr Val Phe Ser Ser Glu Lys Glu Arg Thr
1025                1030                1035 gaa atc aaa caa gat atc aat ctt cct aaa cca gga aaa tat agt         3159
Glu Ile Lys Gln Asp Ile Asn Leu Pro Lys Pro Gly Lys Tyr Ser
1040                1045                1050 ttg tat cta aac aca gaa aca cat gat cgt aaa gcc aca gta act         3204
Leu Tyr Leu Asn Thr Glu Thr His Asp Arg Lys Ala Thr Val Thr
1055                1060                1065 gtt aaa att ggt ggt aag aaa tat acg cgg aca gtg aat aat tcg         3249
Val Lys Ile Gly Gly Lys Lys Tyr Thr Arg Thr Val Asn Asn Ser
    1070                1075                1080 gtt gcc caa aac tac att cag gca gat att aac cat aca agc agg         3294
Val Ala Gln Asn Tyr Ile Gln Ala Asp Ile Asn His Thr Ser Arg
    1085                1090                1095 aaa aat ccg cag tat atg caa aat atg cga att gat ttt gaa atc         3339
Lys Asn Pro Gln Tyr Met Gln Asn Met Arg Ile Asp Phe Glu Ile
1100                1105                1110 cca gat aat gcc aaa aaa ggc tcg gtg aca tta gcg gtt gat aaa         3384
Pro Asp Asn Ala Lys Lys Gly Ser Val Thr Leu Ala Val Asp Lys
1115                1120                1125 ggc aat tcc gtt aca aaa ttt gat gat tta cga att gtt gag cgt         3429
Gly Asn Ser Val Thr Lys Phe Asp Asp Leu Arg Ile Val Glu Arg
1130                1135                1140
```

```
caa acg gat atc atg aac cca gac aaa caa aca gtt att aag caa      3474
Gln Thr Asp Ile Met Asn Pro Asp Lys Gln Thr Val Ile Lys Gln
    1145            1150                1155 gat ttt gaa gac aca caa gca gtt ggg tta tat ccg ttt gtt aaa      3519
Asp Phe Glu Asp Thr Gln Ala Val Gly Leu Tyr Pro Phe Val Lys
1160                1165                1170 ggc tca gct ggt ggt gta gaa gat cca cgg att cat tta tca gaa      3564
Gly Ser Ala Gly Gly Val Glu Asp Pro Arg Ile His Leu Ser Glu
    1175                1180                1185 aga aat gaa cct tac aca caa tat ggt tgg aat gga aac ctt gtt      3609
Arg Asn Glu Pro Tyr Thr Gln Tyr Gly Trp Asn Gly Asn Leu Val
        1190                1195                1200 tca gat gta tta gaa ggc aac tgg tcc ttg aaa gcc cat aaa caa      3654
Ser Asp Val Leu Glu Gly Asn Trp Ser Leu Lys Ala His Lys Gln
1205                1210                1215 gga gca gga ttg atg ctt caa aca att ccg caa aat att aaa ttt      3699
Gly Ala Gly Leu Met Leu Gln Thr Ile Pro Gln Asn Ile Lys Phe
    1220                1225                1230 gaa ccg aac aag aaa tat acg gtc caa ttt gat tat caa act gat      3744
Glu Pro Asn Lys Lys Tyr Thr Val Gln Phe Asp Tyr Gln Thr Asp
        1235                1240                1245 ggt gaa aat gtc ttt act gct ggg acc att aat ggg gag ttg aaa      3789
Gly Glu Asn Val Phe Thr Ala Gly Thr Ile Asn Gly Glu Leu Lys
1250                1255                1260 aat aac aat gac ttt aag cca gtc ggt gag tta act tcg aca gca      3834
Asn Asn Asn Asp Phe Lys Pro Val Gly Glu Leu Thr Ser Thr Ala
    1265                1270                1275 gca gat ggt caa acc aag cat tat gaa gca gaa ata att ggg gat      3879
Ala Asp Gly Gln Thr Lys His Tyr Glu Ala Glu Ile Ile Gly Asp
        1280                1285                1290 gct tca gga aac act acg ttt ggt att ttt aca aca ggt gcc gat      3924
Ala Ser Gly Asn Thr Thr Phe Gly Ile Phe Thr Thr Gly Ala Asp
1295                1300                1305 aaa gat ttc att atg gat aac ttt acg gtc aca gtg gaa tca aaa      3969
Lys Asp Phe Ile Met Asp Asn Phe Thr Val Thr Val Glu Ser Lys
    1310                1315                1320 aaa taa                                                          3975
Lys

<210> SEQ ID NO 12
<211> LENGTH: 1324
<212> TYPE: PRT
<213> ORGANISM: Enterococcus faecalis V583

<400> SEQUENCE: 12

Met Lys His Gly Lys Ile Lys Arg Phe Ser Thr Leu Thr Leu Leu Ala
1               5                   10                  15

Ser Ala Thr Ile Leu Val Pro Leu Ser Thr Ser Ala Glu Glu Thr Thr
            20                  25                  30

Asn Ser Ser Thr Glu Thr Ser Ser Met Val Glu Pro Thr Ala Thr
        35                  40                  45

Glu Glu Lys Leu Trp Gln Ser Asp Phe Pro Gly Gly Lys Thr Gly Glu
    50                  55                  60

Trp Gln Asp Val Ile Gly Lys Thr Asn Arg Glu Leu Ala Gly Glu Ser
65                  70                  75                  80

Leu Ala Ile Ser Arg Asp Ala Ala Ala Gly Asn Asn Ala Val Ser Leu
                85                  90                  95

Asn Leu Asp Ser Pro Lys Leu Ala Asp Gly Glu Val Glu Thr Lys Phe
```

```
            100                 105                 110
Lys Tyr Thr Ala Gly Ser Gly Arg Thr Gly Val Ile Ile Arg Gly Asn
            115                 120                 125

Thr Lys Asp Ser Trp Val Phe Val Gly Tyr Asn Ala Asn Gly Lys Trp
130                 135                 140

Leu Val Glu Ser Pro Asn Ser Trp Asn Asp Ser Ile Ser Gly Pro Thr
145                 150                 155                 160

Leu Asn Glu Asp Thr Asn Tyr Leu Leu Lys Val Arg Tyr Val Gly Glu
            165                 170                 175

Lys Ile Thr Ile Trp Leu Asn Thr Thr Leu Ile Tyr Glu Gly Glu Pro
            180                 185                 190

Val Leu Ala Asn Gly Asp Lys Ile Pro Thr Glu Ala Gly His Val Gly
            195                 200                 205

Val Arg Leu Trp Tyr Asp Lys Lys Ile Val Asn Tyr Asp Tyr Phe Lys
            210                 215                 220

Asn Gly Pro Val Asp Ser Ile Pro Glu Ile Val Pro Glu Val Thr Gln
225                 230                 235                 240

Ile Ala Pro Val Lys Val Phe Thr Lys Ile Gly Val Ala Pro Lys Leu
            245                 250                 255

Pro Lys Gln Val Lys Val Thr Tyr Asn Thr Gly Lys Glu Ala Asn Glu
            260                 265                 270

Ala Val Arg Trp Asn Glu Ile Asp Pro Asp Ala Tyr Lys Glu Pro Gly
            275                 280                 285

Thr Phe Glu Val Asp Gly Thr Leu Glu Asn Thr Asn Ile Lys Ala Lys
            290                 295                 300

Ala Ser Ile Val Val Ala Lys Asp Asn Glu Ala Glu Lys Gly Asp Lys
305                 310                 315                 320

Ile Ser Ser Ala Asp Leu Thr Ala Val Val Asp Pro Gln Phe Pro Arg
            325                 330                 335

Ile Ile Arg Tyr Glu Asp Pro Gln Ser Asn Gln Val Ile Phe Asn Gly
            340                 345                 350

Gln His Glu Lys Ile Asp Gln Val Met Ile Asp Gly Lys Ala Tyr Lys
            355                 360                 365

Ala Thr Ala Glu Lys Gln Lys Ser Glu Ala Asn Gln Ala Val Tyr Asn
            370                 375                 380

Val Ala Val Pro Glu Ile Gly Leu Arg Phe Thr Thr Thr Leu Thr Val
385                 390                 395                 400

Ser Glu Gly Gln Glu Leu Ala Met Lys Leu Ser Asp Ile Arg Glu Glu
            405                 410                 415

Gly Thr Lys Ile His Thr Ile Ser Ile Pro Asn Gln Gly Leu Ile Ser
            420                 425                 430

Val Asn Ser Thr Asp Glu Gly Ala Thr Phe Ala Gly Val Val Met Asn
            435                 440                 445

Thr Gly Thr Asn Ala Asn Asn Gly Asn Lys Asn Gly Asp Thr Ile Gln
            450                 455                 460

Asp Leu Thr Thr Thr Ser Gln Glu Glu Thr Lys Lys Tyr Met Tyr Gly
465                 470                 475                 480

Phe Leu Asn Thr Ala Asn Tyr Ala Ala Ser Phe Trp Thr Asn Ala Tyr
            485                 490                 495

Gly Asp Gly Ser Val Asp Gly Ser Asp Asn Asn Arg Ile His Lys Gln
            500                 505                 510

Thr Lys Glu Ala Ala Thr Gly Phe Val Thr Thr Leu Ser Ser Gly Ala
            515                 520                 525
```

-continued

```
Trp Thr Tyr Arg Pro Phe Asp Ala Pro Glu Asp Tyr Thr Thr Gly Glu
    530                 535                 540

Thr Pro Glu Val Lys Val Lys Phe Ser Lys Asp Ser Asn Asp Asp Asn
545                 550                 555                 560

Arg Val Asp Trp Gln Asp Ala Ala Ile Gly Phe Arg Ser Ile Met Asn
                565                 570                 575

Asn Pro Met Gly Ala Glu Lys Val Pro Glu Leu Val Asn Gln Arg Ile
            580                 585                 590

Pro Phe Asn Phe Ala Ser Gln Ala Thr Asn Pro Phe Leu Val Thr Leu
        595                 600                 605

Asp Glu Ser Lys Arg Ile Tyr Asn Leu Thr Asp Gly Leu Gly Gln Met
    610                 615                 620

Asn Leu Leu Lys Gly Tyr Gln Asn Glu Gly His Asp Ser Ala His Pro
625                 630                 635                 640

Asp Tyr Gly Ala Ile Gly Gln Arg Pro Gly Gly Glu Gln Ala Leu Asn
                645                 650                 655

Gln Leu Ile Asp Glu Gly His Lys Leu Asn Ala Val Phe Gly Val His
            660                 665                 670

Ile Asn Asp Thr Glu Ser Tyr Pro Glu Ala Lys Gly Phe Asn Glu Glu
        675                 680                 685

Leu Val Asp Pro Thr Lys Arg Gly Trp Asp Trp Leu Asp Pro Ser Tyr
    690                 695                 700

Phe Ile Lys Gln Arg Pro Asp Thr Leu Ser Gly Arg Arg Tyr Glu Arg
705                 710                 715                 720

Phe Lys Glu Leu Lys Gln Lys Ala Pro Asn Leu Asp Tyr Ile Tyr Val
                725                 730                 735

Asp Val Trp Gly Asn Gln Gly Glu Ser Gly Trp Ala Ser Arg Gln Leu
            740                 745                 750

Ser Lys Glu Ile Asn Ser Leu Gly Trp Phe Thr Thr Asn Glu Phe Pro
        755                 760                 765

Asn Ala Leu Glu Tyr Asp Ser Val Trp Asn His Trp Ser Ala Glu Lys
    770                 775                 780

Asp Tyr Gly Gly Thr Thr Lys Gly Phe Asn Ser Thr Ile Val Arg
785                 790                 795                 800

Phe Ile Arg Asn His Gln Lys Asp Thr Trp Ile Ile Ser Asp Asn Pro
                805                 810                 815

Leu Leu Gly Gly Ala Glu Phe Glu Ala Tyr Glu Gly Trp Val Gly Lys
            820                 825                 830

Thr Asn Phe Asn Thr Tyr Arg Gln Lys Thr Phe Ala Ile Asn Val Pro
        835                 840                 845

Thr Lys Phe Leu Gln His Tyr Gln Ile Thr Asn Trp Glu Thr Thr Thr
    850                 855                 860

Ala Ala Asp Gly Gln Ile Tyr Gly Thr Ile Lys Leu Ala Asn Gly Ala
865                 870                 875                 880

Glu Lys Val Thr Val Thr Gln Ala Asp Ala Asn Ser Pro Arg Ser Ile
                885                 890                 895

Thr Leu Asn Glu Thr Glu Val Leu Lys Gly Asp Ala Tyr Leu Leu Pro
            900                 905                 910

Trp Asn Val Asn Gly Gln Asp Lys Leu Tyr His Trp Asn Pro Lys Gly
        915                 920                 925

Gly Thr Ser Thr Trp Ser Leu Asp Lys Lys Met Gln Gly Lys Thr Asn
    930                 935                 940
```

```
Leu His Leu Tyr Glu Leu Thr Asp Gln Gly Arg Ile Asp Lys Gly Ala
945                 950                 955                 960

Ile Ala Thr Thr Asn Asn Gln Val Thr Ile Gln Ala Glu Ala Asn Thr
                965                 970                 975

Pro Tyr Val Ile Ala Glu Pro Asp Ser Ile Glu Pro Met Thr Phe Gly
            980                 985                 990

Thr Gly Thr Pro Phe Lys Asp Pro Gly Phe Asn Glu Ala Asn Thr Leu
        995                 1000                1005

Lys Asn Asn Trp Lys Val Phe Arg Gly Asp Gly Glu Val Lys Lys
   1010                1015                1020

Asp Ala Asn Gly Asp Tyr Val Phe Ser Ser Glu Lys Glu Arg Thr
   1025                1030                1035

Glu Ile Lys Gln Asp Ile Asn Leu Pro Lys Pro Gly Lys Tyr Ser
   1040                1045                1050

Leu Tyr Leu Asn Thr Glu Thr His Asp Arg Lys Ala Thr Val Thr
   1055                1060                1065

Val Lys Ile Gly Gly Lys Lys Tyr Thr Arg Thr Val Asn Asn Ser
   1070                1075                1080

Val Ala Gln Asn Tyr Ile Gln Ala Asp Ile Asn His Thr Ser Arg
   1085                1090                1095

Lys Asn Pro Gln Tyr Met Gln Asn Met Arg Ile Asp Phe Glu Ile
   1100                1105                1110

Pro Asp Asn Ala Lys Lys Gly Ser Val Thr Leu Ala Val Asp Lys
   1115                1120                1125

Gly Asn Ser Val Thr Lys Phe Asp Asp Leu Arg Ile Val Glu Arg
   1130                1135                1140

Gln Thr Asp Ile Met Asn Pro Asp Lys Gln Thr Val Ile Lys Gln
   1145                1150                1155

Asp Phe Glu Asp Thr Gln Ala Val Gly Leu Tyr Pro Phe Val Lys
   1160                1165                1170

Gly Ser Ala Gly Gly Val Glu Asp Pro Arg Ile His Leu Ser Glu
   1175                1180                1185

Arg Asn Glu Pro Tyr Thr Gln Tyr Gly Trp Asn Gly Asn Leu Val
   1190                1195                1200

Ser Asp Val Leu Glu Gly Asn Trp Ser Leu Lys Ala His Lys Gln
   1205                1210                1215

Gly Ala Gly Leu Met Leu Gln Thr Ile Pro Gln Asn Ile Lys Phe
   1220                1225                1230

Glu Pro Asn Lys Lys Tyr Thr Val Gln Phe Asp Tyr Gln Thr Asp
   1235                1240                1245

Gly Glu Asn Val Phe Thr Ala Gly Thr Ile Asn Gly Glu Leu Lys
   1250                1255                1260

Asn Asn Asn Asp Phe Lys Pro Val Gly Glu Leu Thr Ser Thr Ala
   1265                1270                1275

Ala Asp Gly Gln Thr Lys His Tyr Glu Ala Glu Ile Ile Gly Asp
   1280                1285                1290

Ala Ser Gly Asn Thr Thr Phe Gly Ile Phe Thr Thr Gly Ala Asp
   1295                1300                1305

Lys Asp Phe Ile Met Asp Asn Phe Thr Val Thr Val Glu Ser Lys
   1310                1315                1320

Lys

<210> SEQ ID NO 13
```

```
<211> LENGTH: 26
<212> TYPE: DNA
<213> ORGANISM: Artificial
<220> FEATURE:
<223> OTHER INFORMATION: Synthetic DNA

<400> SEQUENCE: 13
ttaacctcca tgggcagcgg gggagg                                          26

<210> SEQ ID NO 14
<211> LENGTH: 30
<212> TYPE: DNA
<213> ORGANISM: Artificial
<220> FEATURE:
<223> OTHER INFORMATION: Synthetic DNA

<400> SEQUENCE: 14
aacctgcggc cgccagttgc tcgcgattgc                                      30

<210> SEQ ID NO 15
<211> LENGTH: 20
<212> TYPE: DNA
<213> ORGANISM: Artificial
<220> FEATURE:
<223> OTHER INFORMATION: Synthetic DNA

<400> SEQUENCE: 15
tgcgattcat cgcctagcag                                                 20

<210> SEQ ID NO 16
<211> LENGTH: 8
<212> TYPE: PRT
<213> ORGANISM: Homo sapiens

<400> SEQUENCE: 16

Ala Ser Thr Thr Thr Asn Tyr Thr
1               5

<210> SEQ ID NO 17
<211> LENGTH: 12
<212> TYPE: PRT
<213> ORGANISM: Homo sapiens

<400> SEQUENCE: 17

Phe Arg Lys Lys Trp Asn Lys Trp Ala Leu Ser Arg
1               5                   10

<210> SEQ ID NO 18
<211> LENGTH: 9
<212> TYPE: PRT
<213> ORGANISM: Digitalis purpurea

<400> SEQUENCE: 18

Arg Pro Pro Gly Phe Ser Pro Phe Arg
1               5
```